(12) United States Patent
Stevens et al.

(10) Patent No.: US 7,115,619 B2
(45) Date of Patent: Oct. 3, 2006

(54) $N^8$, $N^{13}$-DISUBSTITUTED QUINO[4,3,2-KL]ACRIDINIUM SALTS AS THERAPEUTIC AGENTS

(75) Inventors: Malcolm F. G. Stevens, Nottingham (GB); Lloyd R Kelland, Reigate (GB); Robert A Heald, Kettering (GB)

(73) Assignee: Cancer Research Technology Limited, London (GB)

( * ) Notice: Subject to any disclaimer, the term of this patent is extended or adjusted under 35 U.S.C. 154(b) by 119 days.

(21) Appl. No.: 10/398,767

(22) PCT Filed: Oct. 12, 2001

(86) PCT No.: PCT/GB01/04557

§ 371 (c)(1),
(2), (4) Date: Oct. 7, 2003

(87) PCT Pub. No.: WO02/30932

PCT Pub. Date: Apr. 18, 2002

(65) Prior Publication Data

US 2004/0063739 A1    Apr. 1, 2004

Related U.S. Application Data

(60) Provisional application No. 60/239,267, filed on Oct. 12, 2000.

(51) Int. Cl.
*A61K 31/4745* (2006.01)
*C07D 471/02* (2006.01)

(52) U.S. Cl. .................. 514/280; 546/49; 544/125; 435/184; 514/232.8

(58) Field of Classification Search ................ 514/280, 514/232.8; 546/49; 544/125; 435/184
See application file for complete search history.

(56) References Cited

OTHER PUBLICATIONS

Stanslas et al; "Antitumor Polycyclic Acridines. 7. Synthesis and Biological Properties of DNA Affinic Tetra- and Pentacyclic Acridines"; Journal of Medicinal Chemistry, 2000, 43(8), 1563-1573, XP002201185.

Neidle, S., et al., 1999, "Telomerase as an Anti-Cancer Target: Current Status and Future Prospects," Anti-Cancer Drug Design, vol. 14, pp. 341-347.

Oszczapowicz, J.; Jaroszewska-Manaj, J.; Ciszak E.; Gdaniec, M., 1988, "Formation of Qunioacridinium System. A Novel Reaction of Quinaldinium Salts," Tetrahedron, vol. 44, No. 21, pp. 6645-6650.

Perry, P.J., et al., 1998, "1,4- and 2,6-Disubstituted Amidoanthracene-9, 10-dione Derivatives as Inhibitors of Human Telomerase," J. Med. Chem., vol. 41, pp. 3253-3260.

Perry et al., 1998, "Telomeres and Telomerase: Targets for Cancer Chemotherapy!," Exp. Opin. Ther. Patents, vol. 8, No. 12, pp. 1567-1586.

Reisch, J., et al., 1991, "Convenient Synthesis of Isoacronycine and Some Other New Acridone Derivatives," Liebigs Ann. Chem., pp. 695-689.

Sharma, S., et al., 1997, "Preclinical and Clinical Strategies for Development of Telomerase and Telomere Inhibitors," Annals of Oncology, vol. 8, pp. 1063-1074.

Song, Z., et al., 1993, "Improved Synthesis of Quinaldines by the Skraup Reaction," J. Heterocyclic Chem., vol. 30, pp. 17-21.

Stanslas, J., et al., 2000, "Antitumor Polycyclic Acridines. 7. Synthesis and Biological Properties of DNA Affinic Tetra- and Pentacyclic Acridines," J. Med. Chem., vol. 43, pp. 1563-1572.

Timari, G., et al., 1996, "Synthesis of Novel Ellipticine Analogues and Their Inhibition of Molony Leukemia Reverse Transcriptase," Bioorganic & Medicinal Chemistry Letters, vol. 6, No. 23, p. 2831-2836.

Urquidi, V., et al., 1998, "Telomerase in Cancer: Clinical Applications," Ann. Med., vol. 30, pp. 419-430.

Wolfe, J.P., et al., 2000, "Simple, efficient catalyst system for the palladium-catalyzed amination or aryl chlorides, bromides, and triflates," J. Org. Chem., vol. 65, pp. 1158-1174.

Albert, A., 1966, The Acridines: Their Preparation, Physical, Chemical, and Biological Properties and Uses, $2^{nd}$ Edition, Edward Arnold (Publishers) Ltd., London (table of contents).

Autexier, 1999, "Telomerase as a Possible Target for Anticancer Therapy," Chemistry & Biology, Nov. 1999, vol. 6, pp. R299-R303.

Bostock-Smith, C.E., et al., 1999, "Molecular Recognition between a New Pentacyclic Acridinium Salt and DNA Sequences Investigated by Optical Spectroscopic Techniques, Proton Nuclear Magnetic Resonance Spectroscopy, and Molecular Modeling," Biochemistry, vol. 38, No. 21, pp. 6723-6731.

Coulson, D.R., 1990, "Tetrakis(triphenylphoshine) palladium(0)", Inorganic Synthesis, Chapter 28, pp. 107-109.

Gimenez-Arnau et al., 1998, "Antitumour Polycyclic Acridines. Part 4. Physico-chemical studies on the interactions between DNA and novel tetracyclic acridine derivatives," Anti-Cancer Drug Design, vol. 13, pp. 431-451.

Gimenez-Arnau et al., 1998, "Antitumour Polycyclic Acridines. Part 2. Physicochemical Studies on the Interactions between DNA and Novel Polycyclic Acridine Derivatives," Anti-Cancer Drug Design, vol. 13, pp. 125-143.

(Continued)

*Primary Examiner*—Charanjit S. Aulakh
(74) *Attorney, Agent, or Firm*—Nixon & Vanderhye P.C.

(57) ABSTRACT

The present invention pertains to certain $N^8,N^{13}$-disubstituted quino[4,3,2-kl]acridinium salts of formula (Q⁻) which inhibit telomerase wherein: p is an integer from 0 to 4; q is an integer from 0 to 3; r is an integer from 0 to 4; each $R^A$ is —H or a ring substituent; each $R^B$ is —H or a ring substituent; each $R^C$ is —H or a ring substituent; $R^{N8}$ is a nitrogen substituent; $R^{N13}$ is a nitrogen substituent; and, Q is an anion. The present invention also pertains to pharmaceutical compositions comprising such compounds, and the use of such compounds and compositions, both in vitro and in vivo, to inhibit telomerase, to regulate cell proliferation, and in the treatment of proliferative conditions, such as cancer.

58 Claims, No Drawings

OTHER PUBLICATIONS

Gullier, F., et al., 1995, "Combined Metalation-Palladium-Catalyzed Cross Coupling Strategies. A Formal Synthesis of the Marine Alkaloid Amphimedine," J. Org. Chem., vol. 60, pp. 292-296.

Hagan, D.J., et al., 1997, "Antitumour polycyclic acridines. Part 1. Synthesis of 7H-pyrido and 8H-quino-[4,3,2-kl]acridines by Graebe-Ullmann thermolysis of 9-(1,2,3-triazol-1-yl)acridines: application of differential scanning calorimetry to predict optimum cyclisation conditions," J. Chem. Soc., Perkin Trans. I, pp. 2739-2746.

Hagan, D.J., et al., 1998, "Antitumour polycyclic acridines. Part 3. A two-step conversion of 9-azidoacridine to 7h-pyrido[4,3,2-kl]acridines by Graebe-Ullmann thermolysis of substituted 9-(1,2,3-triazol-1-yl) acridines," J. Chem. Soc., Perkin Trans. I, pp. 915-923.

Hodgeman, D.K.C. and Prager, R.H., 1972, "Acridone Studies. VIII. Preparation and Properties of the Monobromo-, Nitro-, Amino-, and Piperadino-10-Methylacridones," Aus.J. Chem., vol. 25, pp. 191-199.

Jaroszewaka-Manaj, J., et al., 2000, "1H, 13C and 15N NMR and GIAO CPHF Calculations on Two Quinoacridinium Salts," Magnetic Resonance in Chemistry, vol. 38, No. 6, pp. 482-485.

Julino, M., et al., 1998, "Antitumour Polycyclic Acridines. Part 5. Synthesis of 7H-Pyrido[4,3,2-kl]acridines with exploitable functionality in the pyridine ring," J. Chem. Soc., Perkin Trans. I, pp. 1677-1684.

Katritzky, A.R., et al., 1999, "Polycyclic Fused Phenanthridines: An Alternative Approach from Benzotriazoles," J. Heterocyclic Chem., vol. 36, pp. 927-932.

Littke, A.F., et al., 1999, "Heck Reactions in the Presence of P(t-Bu)3: Expanded Scope and Milder Reaction Conditions for the Coupling of Aryl Chlorides," J. Org. Chem., vol. 64, pp. 10-11.

Missailidis, S., et al., 1997, "Spectroscopic Studies of the Interactions Between DNA and Novel Polycyclic Acridine Derivatives," in Spectroscopy of Biological Molecules: Modern Trends, (Euro. Conf.), 7[th] (editors: Carmona, P., et al.), pp. 391-392.

Mitchell, G., et al., 1987, Cyclo-octa[def]carbazole, a New Heterocyclic Paratropic Ring System, J. Chem. Soc., Perkin Trans. 1, vol. 2, pp. 403-412.

$N^8, N^{13}$-DISUBSTITUTED QUINO[4,3,2-KL]ACRIDINIUM SALTS AS THERAPEUTIC AGENTS

RELATED APPLICATION

This application claims priority to U.S. Provisional Application No. 60/239,267 filed 12 Oct. 2000, the contents of which are incorporated herein by reference in their entirety.

TECHNICAL FIELD

This invention pertains generally to the field of telomerase inhibitors, and more specifically to certain $N^8, N^{13}$-disubstituted quino[4,3,2-kl]acridinium salts which inhibit telomerase. The present invention also pertains to pharmaceutical compositions comprising such compounds, and the use of such compounds and compositions, both in vitro and in vivo, to inhibit telomerase, to regulate cell proliferation, and in the treatment of proliferative conditions, such as cancer.

BACKGROUND

Mammalian cells are normally subject to tight controls regulating replication in order to maintain organ structure and function. Conversely, the disease of cancer is characterized by uncontrolled proliferation. Compromise of any of the steps involved in cell cycle regulation could be involved in escape from regulatory mechanisms and therefore lead to neoplasia. However, even if a cell escapes proliferation suppression, there are limitations to the number of replicative cycles it can progress through before safety mechanisms cause cell cycle shutdown, and this restriction is thought to be a component of the process of organismal ageing. Although ageing is a complex process, a major candidate for the molecular signal for replicative senescence is that of telomere shortening.

Telomeres are nucleoprotein structures at the ends of linear chromosomes consisting of DNA sequences arranged in tandemly repeated units which extend from less than 100 to several thousands of bases. In contrast to chromosome ends created by random breakage, telomeres are stable structures not prone to degradation or fusion with other chromosome ends and are not subject to DNA repair mechanisms.

During each round of cellular replication, both strands of DNA separate and daughter strands are synthesized in a slightly different manner on the leading and lagging strand. While the lead strand replicates in a continuous fashion using conventional DNA polymerase, the lagging strand replicates in a discontinuous fashion using Okazaki fragments. The gaps between individual Okazaki fragments are filled by the regular DNA polymerase. However, this sets the stage for a potential "end replication problem." This arises because Okazaki fragment priming will not necessarily start at the very end of the DNA and because the RNA primer, once removed, would result in a portion of unreplicated 3'-DNA (an unrepaired 3'-overhang). This can lead to a loss of 50–200 base pairs with every round of somatic cell division, with eventual shortening of telomeres to a length that coincides with the activation of an antiproliferative mechanism termed "mortality stage 1" (M1), and at this stage, senescence in somatic cells occurs. Thus, telomere shortening functions as a "mitotic clock" and limits division in somatic cells to about 50–70 times, thereby contributing to cell aging.

In some cells, due to various mechanisms, the M1 stage is bypassed and cells can continue to divide until telomeres become critically shortened ("mortality stage 2," M2). At this M2 stage, in many immortalized cells, a specialized DNA polymerase called "telomerase" appears and utilizes its internal RNA template to synthesize the telomeric sequence and compensate for the loss of telomeric DNA due to incomplete replication. This prevents further shortening of telomeres, and the resulting stabilization of their length contributes to immortalization.

Telomerase is not expressed, or if it is, its activity is repressed, in most normal mammalian somatic cells. Exceptions to this rule include male germ line cells and some epithelial stem cells (e.g., as in the intestinal crypts, the basal layer of the epidermis, and within human hair follicles). Nonetheless, both telomerase activity and shortened but stabilized telomeres have been detected in the majority of tumours examined (and in over 90% of all human cancers examined), and consequently, telomeres and telomerase are recognized targets for anti-neoplastic (e.g., cancer) chemotherapy.

The absence of telomerase in most normal cells makes this enzyme a particularly attractive target, considering that its inhibition would probably cause minimal damage to the whole patient. The fact that tumour cells have shorter telomeres and higher proliferation rates than normal replicative cell populations suggests that a therapeutic telomerase inhibitor may cause tumour cell death well before damage to regenerative tissues occurs, thereby minimizing undesirable side-effects.

For a more detailed discussion of telomeres and telomerase, and their role as anti-proliferative targets, see, for example, Sharma et al., 1997; Urquidi et al., 1998; Perry et al., 1998b; Autexier, 1999; and Neidle et al., 1999, and references therein.

Since the early days of the 20th century, acridine derivatives have attracted the attention of medicinal chemists because of their broad-ranging biological properties (see, for example, Albert, 1966). A number of polycyclic systems which incorporate the acridine structure have been prepared and/or isolated and their biological properties investigated. Several pyrido[2,3,4-kl]acridines have been isolated from marine organisms in two phyla, the tunicates and sponges, where they are presumably employed as chemical warfare agents to deter marine predators.

Mitchell et al., 1987, report the synthesis of unsubstituted quino[4,3,2-kl]acridine, shown below (see, for example, compound 46 at page 408).

8H-quino[4,3,2-kl]acridine Registry No. 111180-99-5

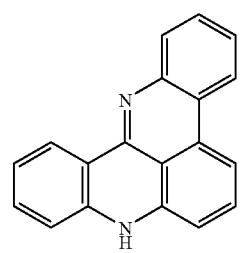

Recently, a number of substituted quino[4,3,2-kl]acridines have been described in the literature. See, for example, Hagan et al., 1997 (Part 1); Gimenez-Arnau et al., 1998a (Part 2); Hagan et al., 1998 (Part 3); Gimenez-Arnau et al., 1998b (Part 4); Julino et al., 1998 (Part 5); Bostock-Smith et al., 1999 (Part 6); and Stanslas et al., 2000 (Part 7). These include the following compounds:

3-chloro-8H-quino[4,3,2-kl]acridine Registry No. 198025-90-0

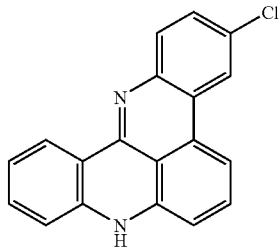

2-nitro-8H-quino[4,3,2-kl]acridine Registry No. 198025-91-1

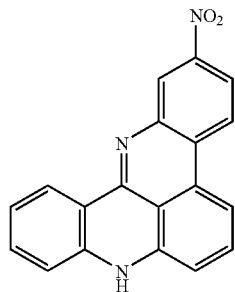

3-methyl-8H-quino[4,3,2-kl]acridine Registry No. 198025-92-2

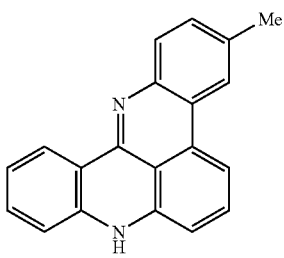

12-methyl-8H-quino[4,3,2-kl]acridine Registry No. 198025-93-3

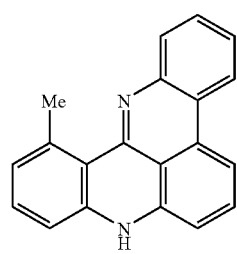

2-amino-8H-quino[4,3,2-kl]acridine Registry No. 198025-95-5

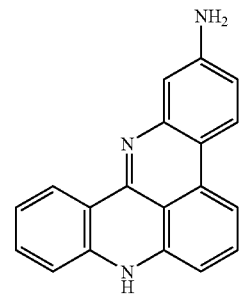

Protonated forms of some of the above compounds have also been reported. See, for example, Gimenez-Arnau et al., 1998a (Part 2):

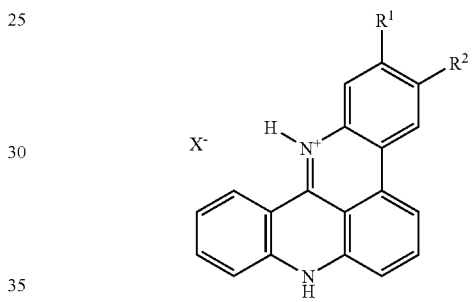

2-amino-8H-quino[4,3,2-kl]acridine was reportedly converted to methanesulfonic, ethanesulfonic, and tetrafluoroborate acid salts (Registry Nos. 266326-59-4, 266326-60-7, and 266326-61-8, respectively), to improve water solubility in subsequent biological studies. See, Stanslas, J., et al., 2000 (Part 7) at page 1565, right hand column. Apparently, mono-protonation occurred at the N-13 position, and the salt had the following structure:

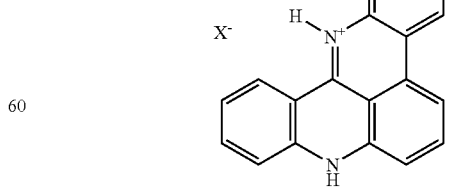

Katritzky et al., 1999, report the synthesis of a few N[8]-methyl-quino[4,3,2-kl]acridines, shown below. However, the publication is silent as to possible applications of these compounds.

8-methyl-8H-quino[4,3,2-kl]acridine Registry No. 252882-87-4

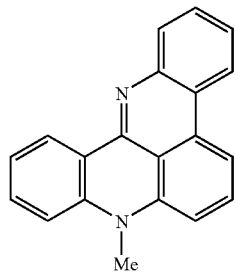

2-chloro-8-methyl-8H-quino[4,3,2-kl]acridine Registry No. 252882-91-0

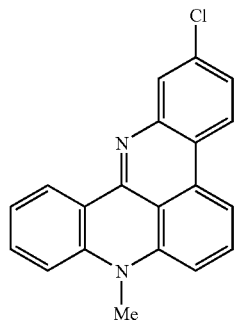

2,3,8-trimethyl-8H-quino[4,3,2-kl]acridine Registry No. 252882-89-6

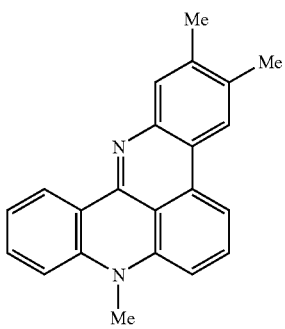

Oszczapowicz et al., 1988, described the synthesis of the N,N-dialkylated salt shown below. However, the publication is silent as to possible applications of this salt. Nonetheless, this compound has apparently been submitted to the National Institute of Cancer Institute (NCI) in the USA for anticancer screening. See, for example, the NCI website (http:\\dtp.nci.nih.gov).

8,13-diethyl-6-methyl-8H-quino[4,3,2-kl]acridinium iodide Registry No. 120132-51-6

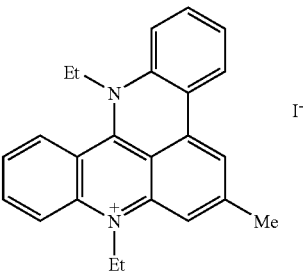

Jaroszewska-Manaj et al., 2000, report the synthesis of another N,N-dialkylated salt, shown below. Again, the publication is silent as to possible applications of this salt.

8,13-diethyl-3,6,11-trimethyl-8H-quino[4,3,2-kl] acridinium iodide Registry No. 287733-21-5

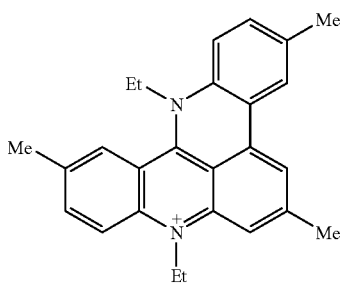

Salts of other polycyclic acridines with quaternary amino groups have also been reported. However, none of these have the quino[4,3,2-kl]acridinium structure. For example, Julino et al., 1998 (Part 5), Bostock-Smith et al., 1999 (Part 6), and Stanslas et al., 2000 (Part 7) describe two salts, quinolizino[2,3,4-kl]acridinium chloride and 1H-2,3-dihydroindolizino[7,6,5-kl]acridinium chloride, the latter of which is reported to have antitumour activity:

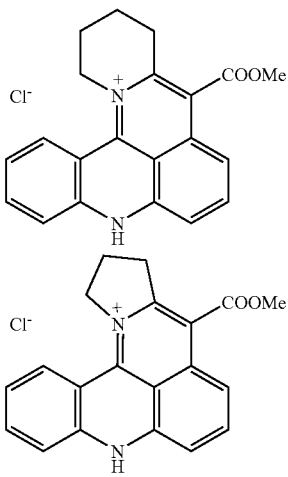

Gimenez-Arnau et al., 1998a (Part 2) and Missailidis et al., 1997 describe physico-chemical studies on the interactions between DNA and a number of the above quino[4,3,2-kl]acridines in their neutral and cationic (salt) forms. Stanslas et al., 2000 (Part 7) report the inhibitory activity of several of the above quino[4,3,2-kl]acridines against a number of cell lines, including several human breast carcinoma cell lines. However, none of these documents teach or suggest $N^8,N^{13}$-disubstituted-quino[4,3,2-kl]acridinium salts, or their potential in biological applications.

The present invention pertains to $N^8,N^{13}$-disubstituted-quino[4,3,2-kl]acridinium salts, and the discovery of their surprising and unexpected activity as telomerase inhibitors.

Although many are known, there remains a great need for potent telomerase inhibitors and antitumour agents, particularly for such compounds which offer additional pharmacological advantages. For example, particularly preferred telomerase inhibitors are ones which are characterized by one or more of the following properties:

(a) no inhibition of Taq polymerase at 10–50 μM (in order to provide specificity and eliminate broad-spectrum polymerase inhibitors);
(b) cell free telomerase inhibition (at <1 μM) at concentrations more than 5 to 10-fold less than for concentrations for acute cytotoxicity;
(c) shortening of telomere length in tumour cells at concentrations 5 to 10-fold less than concentrations for acute cytotoxicity;
(d) telomere shortening in human tumour xenografts; and,
(e) oral bioavailability.

Additionally, there is a great need for antiproliferative agents which offer one or more of the following advantages:

(f) improved activity.
(g) improved selectivity (e.g., against tumour cells versus normal cells).
(h) complement the activity of other treatments (e.g., chemotherapeutic agents);
(i) reduced intensity of undesired side-effects;
(j) fewer undesired side-effects;
(k) simpler methods of administration;
(l) reduction in required dosage amounts;
(m) reduction in required frequency of administration;
(n) increased ease of synthesis, purification, handling, storage, etc.;
(o) reduced cost of synthesis, purification, handling, storage, etc.

Thus, one aim of the present invention is the provision of compounds which are potent telomerase inhibitors, antiproliferative agents, anti-cancer agents, etc. which offer one or more of the above properties and advantages.

The inventors have discovered that certain classes of $N^8,N^{13}$-disubstituted quino[4,3,2-kl]acridinium salts, described herein, offer one or more of the above properties and advantages, and additionally are surprisingly and unexpectedly more active than corresponding known analogues.

SUMMARY OF THE INVENTION

One aspect of the present invention pertains to compounds, specifically, $N^8,N^{13}$-disubstituted quino[4,3,2-kl] acridinium salts, as described herein (with the proviso).

Another aspect of the present invention pertains to a composition comprising a compound as described herein (with or without the proviso) and a pharmaceutically acceptable carrier.

Another aspect of the present invention pertains to a method of inhibiting telomerase in vitro or in vivo, comprising contacting a cell with an effective amount of a compound as described herein (without the proviso).

Another aspect of the present invention pertains to methods of regulating (e.g., inhibiting) cell proliferation, comprising contacting a cell with an effective amount of an active compound, as described herein, whether in vitro or in vivo.

Another aspect of the present invention pertains to methods of treating a proliferative condition in a subject comprising administering to said subject a therapeutically-effective amount of an active compound, as described herein (without the proviso). In one preferred embodiment, the proliferative condition is cancer.

Another aspect of the present invention pertains to an active compound, as described herein (without the proviso), for use in a method of treatment of the human or animal body.

Another aspect of the present invention pertains to an active compound, as described herein (without the proviso), for use in a method of treatment of cancer of the human or animal body.

Another aspect of the present invention pertains to use of an active compound, as described herein (without the proviso), for the manufacture of a medicament for use in the treatment of a proliferative condition. In one preferred embodiment, the proliferative condition is cancer.

Another aspect of the present invention pertains to a kit comprising (a) an active compound, preferably provided as a pharmaceutical composition and in a suitable container and/or with suitable packaging; and (b) instructions for use, for example, written instructions on how to administer the active compound.

Another aspect of the present invention pertains to compounds obtainable by a method of synthesis as described herein, or a method comprising a method of synthesis as described herein.

Another aspect of the present invention pertains to compounds obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspects of the invention.

DETAILED DESCRIPTION OF THE INVENTION

Compounds

The present invention pertains generally to a class of compounds referred to herein as "quino[4,3,2-kl]acridinium salts" (or more particularly, "$N^8,N^{13}$-disubstituted quino[4,3,2-kl]acridinium salts"), which have the following general formula:

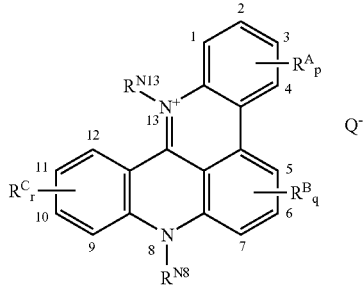

(1)

wherein:
p is independently an integer from 0 to 4;
q is independently an integer from 0 to 3;
r is independently an integer from 0 to 4;
each $R^A$ is independently —H or a ring substituent;
each $R^B$ is independently —H or a ring substituent;
each $R^C$ is independently —H or a ring substituent;
$R^{N8}$ is independently a nitrogen substituent;
$R^{N13}$ is independently a nitrogen substituent; and,
Q is independently an anion;

and pharmaceutically acceptable salts, solvates, amides, esters, ethers, chemically protected forms, and prodrugs thereof.

As will be appreciated by the skilled artisan, the above structure is one of many possible resonance structures which may be drawn to depict the same compound.

As used herein, a reference to one such structure is to be considered a reference to all possible corresponding resonance structures.

For example, another resonance structure of the above compound has the positive charge on the nitrogen atom at the 8-position, instead of at the 13-position:

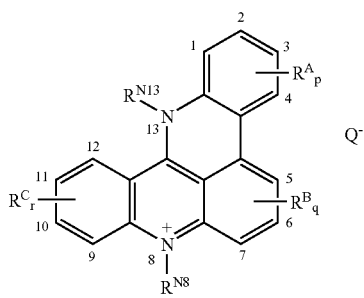

(2)

Note that it is not intended that pairs of substituents, (i.e., $R^A$, $R^B$, $R^C$, $R^{N8}$, and $R^{N13}$) together with the ring atoms to which they are attached, form a cyclic structure. For example, it is not intended that the substituents $R^{A2}$ and $R^{A3}$, together with the carbon atoms they are attached, form a ring which is fused to the parent phenyl ring (i.e., the A-ring).

Proviso

Insofar as the present invention pertains to compounds, per se, these compounds are as defined herein, with the proviso that the compound is not:
8,13-diethyl-6-methyl-8H-quino[4,3,2-kl]acridinium iodide ($R^{A1}$ is —H; $R^{A2}$ is —H; $R^{A3}$ is —H; $R^{A4}$ is —H; $R^{B5}$ is —H; $R^{B6}$ is -Me; $R^{B7}$ is —H; $R^{N8}$ is -Et; $R^{C9}$ is —H; $R^{C10}$ is —H; $R^{C11}$ is —H; $R^{C12}$ is —H; $R^{N13}$ is -Et; and Q⁻ is I⁻);
or:
8,13-diethyl-3,6,11-trimethyl-8H-quino[4,3,2-kl]acridinium iodide ($R^{A1}$ is —H; $R^{A2}$ is —H; $R^{A3}$ is -Me; $R^{A4}$ is —H; $R^{B5}$ is —H; $R^{B6}$ is -Me; $R^{B7}$ is —H; $R^{N8}$ is -Et; $R^{C9}$ is —H; $R^{C10}$ is -Me; $R^{C11}$ is —H; $R^{C12}$ is —H; $R^{N13}$ is -Et; and Q⁻ is I⁻).

In one embodiment, insofar as the present invention pertains to compounds, per se, these compounds are as defined herein, with the proviso that $R^{N8}$ and $R^{N13}$ are not both -Et.

In one embodiment, insofar as the present invention pertains to compounds, per se, these compounds are as defined herein, with the proviso that at least one of the ring substituents, $R^A$, $R^B$, $R^C$, $R^{A1}$, $R^{A2}$, $R^{A3}$, $R^{A4}$, $R^{B5}$, $R^{B6}$, $R^{B7}$, $R^{C9}$, $R^{C10}$, $R^{C11}$, and $R^{C12}$, is not -Me.

These proviso may apply, but do not necessarily apply, to the present invention in its other aspects, for example, as it pertains to pharmaceutical compositions comprising the compounds, methods of inhibition, regulation, treatment, etc. employing the compounds, the compounds for medical use, use of the compounds in the preparation of medicaments, and the like.

Ring Substitution

In one embodiment, p is an integer from 0 to 4.
In one embodiment, p is an integer from 0 to 3.
In one embodiment, p is an integer from 0 to 2.
In one embodiment, p is 0 or 1.
In one embodiment, p is an integer from 1 to 4.
In one embodiment, p is an integer from 1 to 3.
In one embodiment, p is 1 or 2.
In one embodiment, p is 1.
In one embodiment, p is 2.
In one embodiment, p is 3.
In one embodiment, p is 4.
In one embodiment, q is an integer from 0 to 3.
In one embodiment, q is an integer from 0 to 2.
In one embodiment, q is 0 or 1.
In one embodiment, q is an integer from 1 to 3.
In one embodiment, q is 1 or 2.
In one embodiment, q is 1.
In one embodiment, q is 2.
In one embodiment, q is 3.
In one embodiment, r is an integer from 0 to 4.
In one embodiment, r is an integer from 0 to 3.
In one embodiment, r is an integer from 0 to 2.
In one embodiment, r is 0 or 1.
In one embodiment, r is an integer from 1 to 4.
In one embodiment, r is an integer from 1 to 3.
In one embodiment, r is 1 or 2.
In one embodiment, r is 1.
In one embodiment, r is 2.
In one embodiment, r is 3.
In one embodiment, r is 4.
In one embodiment, p is 0, 1, or 2; q is 0 or 1; and r is 0, 1, or 2.
In one embodiment, p is 0, q is 0 and r is 0.
In one embodiment, p is 0, q is 0 and r is 1.
In one embodiment, p is 0, q is 0 and r is 2.
In one embodiment, p is 1, q is 0 and r is 0.
In one embodiment, p is 1, q is 0 and r is 1.
In one embodiment, p is 1, q is 0 and r is 2.
In one embodiment, p is 2, q is 0 and r is 0.
In one embodiment, p is 2, q is 0 and r is 1.

In one embodiment, p is 2, q is 0 and r is 2.
In one embodiment, p is 0, q is 1 and r is 0.
In one embodiment, p is 0, q is 1 and r is 1.
In one embodiment, p is 0, q is 1 and r is 2.
In one embodiment, p is 1, q is 1 and r is 0.
In one embodiment, p is 1, q is 1 and r is 1.
In one embodiment, p is 1, q is 1 and r is 2.
In one embodiment, p is 2, q is 1 and r is 0.
In one embodiment, p is 2, q is 1 and r is 1.
In one embodiment, p is 2, q is 1 and r is 2.

In one embodiment, the compounds have the following formula:

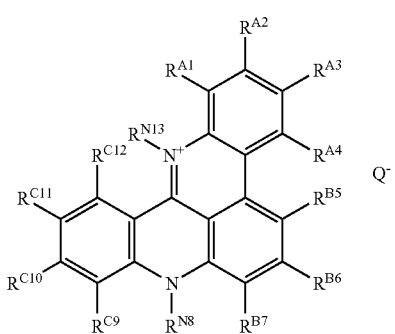

(3)

wherein:
each one of $R^{A1}$, $R^{A2}$, $R^{A3}$, and $R^{A4}$ is independently —H or a ring substituent;
each one of $R^{B5}$, $R^{B6}$, and $R^{B7}$ is independently —H or a ring substituent;
each one of $R^{C9}$, $R^{C10}$, $R^{C11}$, and $R^{C12}$ is independently —H or a ring substituent;
$R^{N8}$ is independently a nitrogen substituent;
$R^{N13}$ is independently a nitrogen substituent; and,
Q is independently an anion;

and pharmaceutically acceptable salts, solvates, amides, esters, ethers, chemically protected forms, and prodrugs thereof.

Substituent Positions
In one embodiment, $R^{A1}$ and $R^{A4}$ are both —H.
In one embodiment, $R^{A1}$, $RA^2$, and $R^{A4}$ are all —H.
In one embodiment, $R^{A1}$, $R^{A3}$, and $R^{A4}$ are all —H.
In one embodiment, $R^{A1}$, $RA^2$, $RA^3$, and $R^{A4}$ are all —H.
In one embodiment, $R^{A1}$, $R^{A2}$, and $R^{A4}$ are all —H, and $R^{A3}$ is not —H.
In one embodiment, $R^{A1}$, $R^{A3}$, and $R^{A4}$ are all —H, and $R^{A2}$ is not —H.
In one embodiment, $R^{B5}$ and $R^{B7}$ are both —H.
In one embodiment, $R^{B5}$, $R^{B6}$, and $R^{B7}$ are all —H.
In one embodiment, $R^{B5}$ and $R^{B7}$ are both —H, and $R^{B6}$ is not —H.
In one embodiment, $R^{C9}$ and $R^{C12}$ are both —H.
In one embodiment, $R^{C9}$, $R^{C10}$, and $R^{C12}$ are all —H.
In one embodiment, $R^{C9}$, $R^{C10}$, and $R^{C12}$ are all —H.
In one embodiment, $R^{C9}$, $R^{C10}$, $R^{C11}$, and $R^{C12}$ are all —H.
In one embodiment, $R^{C9}$, $R^{C10}$, and $R^{C12}$ are all —H, and $R^{C11}$ is not —H.
In one embodiment, $R^{C9}$, $R^{C11}$, and $R^{C12}$ are all —H, and $R^{C10}$ is not —H.

In one embodiment, $R^{A1}$ and $R^{A4}$ are both —H; $R^{B5}$ and $R^{B7}$ are both —H; $R^{C9}$ and $R^{C12}$ are both —H, and the compounds have the following formula:

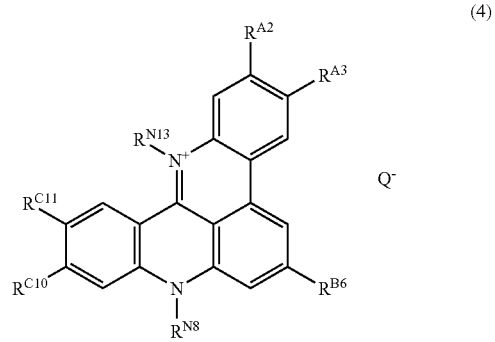

(4)

wherein:
each of $R^{A2}$ and $R^{A3}$ is independently —H or a ring substituent;
$R^{B6}$ is —H or a ring substituent;
each of $R^{C10}$ and $R^{C11}$ is independently —H or a ring substituent;
$R^{N8}$ is a nitrogen substituent;
$R^{N13}$ is a nitrogen substituent; and,
Q is an anion.

In one embodiment, $R^{A1}$, $R^{A2}$, $R^{A3}$, and $R^{A4}$ are all —H; $R^{B5}$, $R^{B6}$, and $R^{B7}$ are all —H; and $R^{C9}$, $R^{C10}$, $R^{C11}$, and $R^{C12}$ are all —H (i.e., 8,13-disubstituted).

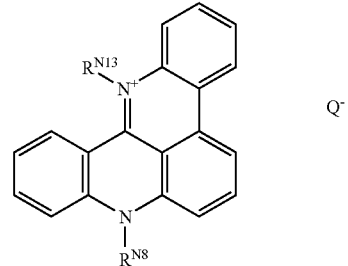

(5)

In one embodiment, $R^{A1}$, $R^{A3}$, and $R^{A4}$ are all —H; $R^{B5}$, $R^{B6}$, and $R^{B7}$ are all —H; $R^{C9}$, $R^{C10}$, $R^{C11}$, and $R^{C12}$ are all —H; and $R^{A2}$ is not —H (i.e., 2,8,13-trisubstituted).

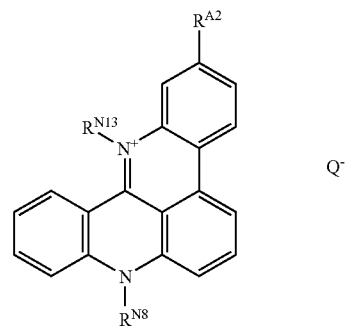

(6)

In one embodiment, $R^{A1}$, $R^{A2}$, and $R^{A4}$ are all —H; $R^{B5}$, $R^{B6}$, and $R^{B7}$ are all —H; $R^{C9}$, $R^{C10}$, $R^{C11}$, and $R^{C12}$ are all —H; and $R^{A3}$ is not —H (i.e., 3,8,13-trisubstituted).

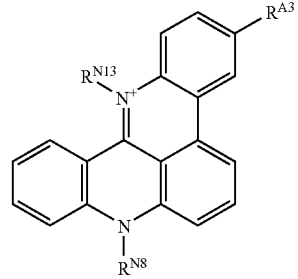

(7)

In one embodiment, $R^{A1}$, $R^{A2}$, $R^{A3}$, and $R^{A4}$ are all —H; $R^{B5}$ and $R^{B7}$ are both —H; $R^{C9}$, $R^{C10}$, $R^{C11}$, and $R^{C12}$ are all —H; and $R^{B6}$ is not —H (i.e., 6,8,13-trisubstituted).

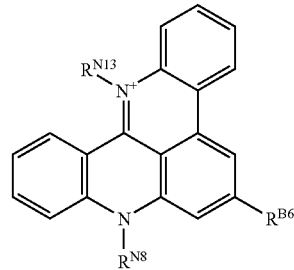

(8)

In one embodiment, $R^{A1}$, $R^{A2}$, $R^{A3}$, and $R^{A4}$ are all —H; $R^{B5}$, $R^{B6}$, and $R^{B7}$ are all —H; $R^{C9}$, $R^{C11}$, and $R^{C12}$ are all —H; and $RC^{10}$ is not —H (i.e., 8,10,13-trisubstituted).

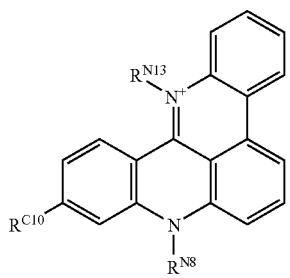

(9)

In one embodiment, $R^{A1}$, $R^{A2}$, $R^{A3}$, and $R^{A4}$ are all —H; $R^{B5}$, $R^{B6}$, and $R^{B7}$ are all —H; $R^{C9}$, $R^{C10}$, and $R^{C12}$ are all —H; and $R^{C11}$ is not —H (i.e., 8,11,13-trisubstituted).

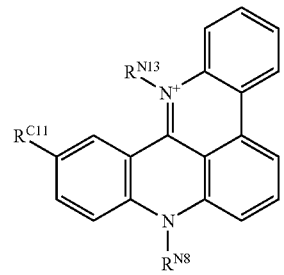

(10)

In one embodiment, $R^{A1}$, $R^{A3}$, and $R^{A4}$ are all —H; $R^{B5}$ and $R^{B7}$ are both —H; $R^{C9}$, $R^{C10}$, $R^{C11}$, and $R^{C12}$ are all —H; and $R^{A2}$ and $R^{B6}$ are both not —H (i.e., 2,6,8,13-tetrasubstituted).

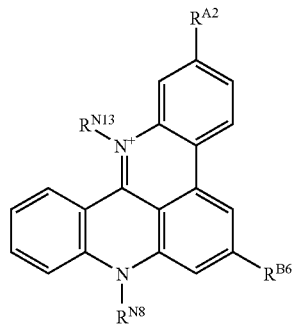

(11)

In one embodiment, $R^{A1}$, $R^{A3}$, and $R^{A4}$ are all —H; $R^{B5}$, $R^{B6}$, and $R^{B7}$ are all —H; $R^{C9}$, $R^{C11}$, and $R^{C12}$ are all —H; and $R^{A2}$ and $R^{C10}$ are both not —H (i.e., 2,8,10,13-tetrasubstituted).

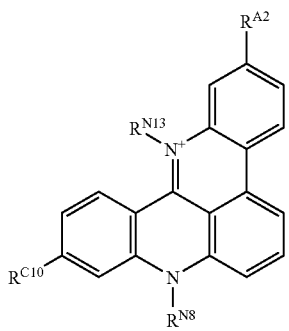

(12)

In one embodiment, $R^{A1}$, $R^{A3}$, and $R^{A4}$ are all —H; $R^{B5}$, $R^{B6}$, and $R^{B7}$ are all —H; $R^{C9}$, $R^{C10}$, and $R^{C12}$ are all —H; and $R^{A2}$ and $R^{C11}$ are both not —H (i.e., 2,8,11,13-tetrasubstituted).

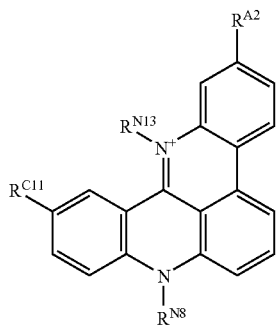
(13)

In one embodiment, $R^{A1}$, $R^{A2}$, and $R^{A4}$ are all —H; $R^{B5}$ and $R^{B7}$ are both —H; $R^{C9}$, $R^{C10}$, $R^{C11}$, and $R^{C12}$ are all —H; and $R^{A3}$ and $R^{B6}$ are both not —H (i.e., 3,6,8,13-tetrasubstituted).

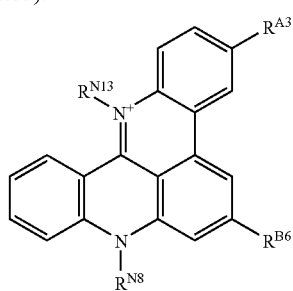
(14)

In one embodiment, $R^{A1}$, $R^{A2}$, and $R^{A4}$ are all —H; $R^{B5}$, $R^{B6}$, and $R^{B7}$ are all —H; $R^{C9}$, $R^{C11}$, and $R^{C12}$ are all —H; and $R^{A3}$ and $R^{C10}$ are both not —H (i.e., 3,8,10,13-tetrasubstituted).

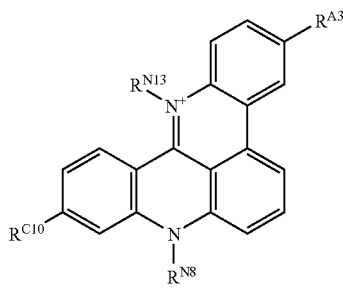
(15)

In one embodiment, $R^{A1}$, $R^{A2}$, and $R^{A4}$ are all —H; $R^{B5}$, $R^{B6}$, and $R^{B7}$ are all —H; $R^{C9}$, $R^{C10}$, and $R^{C12}$ are all —H; and $R^{A3}$ and $R^{C11}$ are both not —H (i.e., 3,8,11,13-tetrasubstituted).

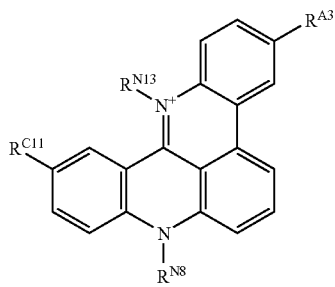
(16)

In one embodiment, $R^{A1}$, $R^{A2}$, $R^{A3}$, and $R^{A4}$ are all —H; $R^{B5}$ and $R^{B7}$ are both —H; $R^{C9}$, $R^{C11}$, and $R^{C12}$ are all —H; and $R^{B6}$ and $R^{C10}$ are both not —H (i.e., 6,8,10,13-tetrasubstituted).

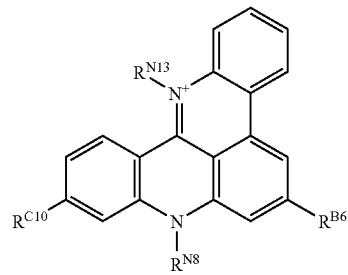
(17)

In one embodiment, $R^{A1}$, $R^{A2}$, $R^{A3}$ and $R^{A4}$ are all —H; $R^{B5}$ and $R^{B7}$ are both —H; $R^{C9}$, $R^{C10}$, and $R^{C12}$ are all —H; and $R^{B6}$ and $R^{C11}$ are both not —H (i.e., 6,8,11,13-tetrasubstituted).

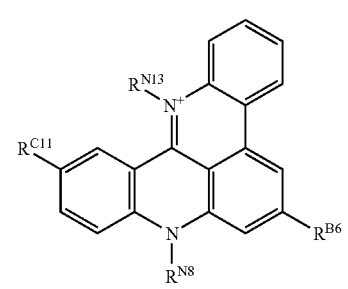
(18)

In one embodiment, $R^{A1}$, $R^{A3}$, and $R^{A4}$ are all —H; $R^{B5}$ and $R^{B7}$ are both —H; $R^{C9}$, $R^{C11}$, and $R^{C12}$ are all —H; and $R^{A2}$, $R^{B6}$, and $R^{C10}$ are all not —H (i.e., 2,6,8,10,13-pentasubstituted).

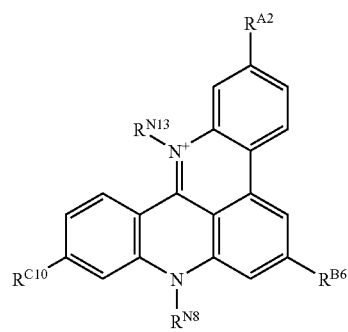
(19)

In one embodiment, $R^{A1}$, $R^{A3}$, and $R^{A4}$ are all —H; $R^{B5}$ and $R^{B7}$ are both —H; $R^{C9}$, $R^{C10}$, and $R^{C12}$ are all —H; and $R^{A2}$, $R^{B6}$, and $R^{C11}$ are all not —H (i.e., 2,6,8,11,13-pentasubstituted).

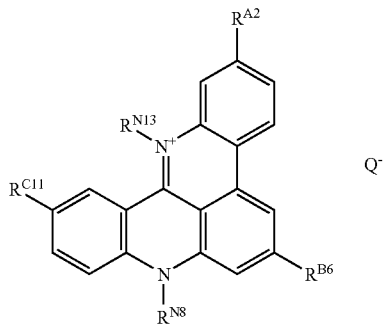

(20)

In one embodiment, $R^{A1}$, $R^{A2}$, and $R^{A4}$ are all —H; $R^{B5}$ and $R^{B7}$ are both —H; $R^{C9}$, $R^{C11}$, and $R^{C12}$ are all —H; and $R^{A3}$, $R^{B6}$, and $R^{C10}$ are all not —H (i.e., 3,6,8,10,13-pentasubstituted).

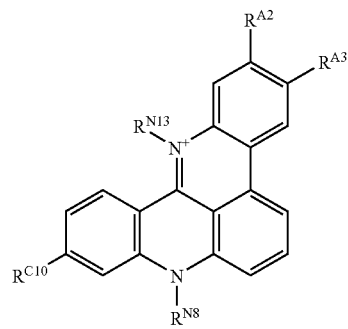

(23)

In one embodiment, $R^{A1}$ and $R^{A4}$ are both —H; $R^{B5}$, $R^{B6}$, and $R^{B7}$ are all —H; $R^{C9}$, $R^{C10}$, and $R^{C12}$ are all —H; and $R^{A2}$, $R^{A3}$, and $R^{C11}$ are all not —H (i.e., 2,3,8,11,13-pentasubstituted).

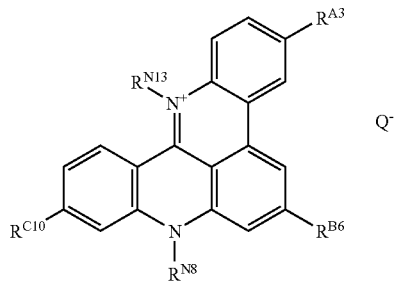

(21)

In one embodiment, $R^{A1}$, $R^{A2}$, and $R^{A4}$ are all —H; $R^{B5}$ and $R^{B7}$ are both —H; $R^{C9}$, $R^{C10}$, and $R^{C12}$ are all —H; and $R^{A3}$, $R^{B6}$, and $R^{C11}$ are all not —H (i.e., 3,6,8,11,13-pentasubstituted).

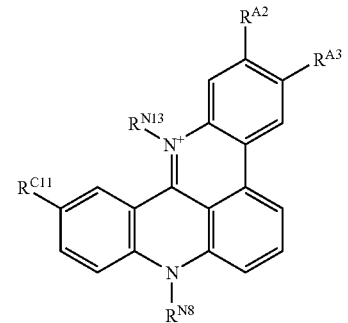

(24)

In one embodiment, $R^{A1}$ and $R^{A4}$ are both —H; $R^{B5}$, $R^{B6}$, and $R^{B7}$ are all —H; $R^{C9}$ and $R^{C12}$ are both —H; and $R^{A2}$, $R^{A3}$, $R^{C10}$, and $R^{C11}$ are all not —H (i.e., 2,3,8,10,11,13-hexasubstituted).

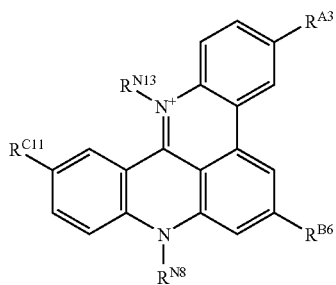

(22)

In one embodiment, $R^{A1}$ and $R^{A4}$ are both —H; $R^{B5}$, $R^{B6}$, and $R^{B7}$ are all —H; $R^{C9}$, $R^{C11}$, and $R^{C12}$ are all —H; and $R^{A2}$, $R^{A3}$, and $R^{C10}$ are all not —H (i.e., 2,3,8,10,13-pentasubstituted).

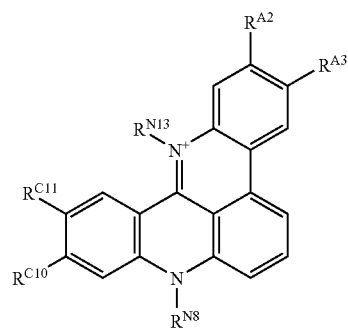

(25)

In one embodiment, $R^{A1}$ and $R^{A4}$ are both —H; $R^{B5}$ and $R^{B7}$ are both —H; $R^{C9}$, $R^{C11}$, and $R^{C12}$ are all —H; and $R^{A2}$, $R^{A3}$, $R^{A6}$, and $R^{C10}$ are all not —H (i.e., 2,3,6,8,10,13-hexasubstituted).

(26)

In one embodiment, $R^{A1}$ and $R^{A4}$ are both —H; $R^{B5}$ and $R^{B7}$ are both —H; $R^{C9}$, $R^{C10}$, and $R^{C12}$ are all —H; and $R^{A2}$, $R^{A3}$, $R^{A6}$, and $R^{C11}$ are all not —H (i.e., 2,3,6,8,1 1,13-hexasubstituted).

(27)

In one embodiment, $R^{A1}$ and $R^{A4}$ are both —H; $R^{B5}$ and $R^{B7}$ are both —H; $R^{C9}$ and $R^{C12}$ are both —H; and $R^{A2}$, $R^{A3}$, $R^{A6}$, $R^{C10}$, and $R^{C11}$ are all not —H (i.e., 2,3,6,8,10,11,13-heptasubstituted).

(28)

In one embodiment, the compound is, with reference to the above formulae:
3-substituted;
6-substituted;
10-substituted;
3,6-disubstituted;
3,10-disubstituted;
6,10-disubstituted;
3,6,10-trisubstituted; or
3,6,11-trisubstituted.

Nitrogen Substituents

Compounds of the present invention are $N^8,N^{13}$-disubstituted quino[4,3,2-kl]acridinium salts, and $R^{N8}$ and $R^{N13}$ are each independently a nitrogen substituent.

Without wishing to be bound to any particular theory or mechanism for activity, it is believed that, in one preferred embodiment, the compounds have nitrogen substituents which (a) are electron withdrawing groups; (b) which do not adversely affect the planarity or near-planarity of the quino [4,3,2-kl]acridinium ion; or (c) both (a) and (b).

In one embodiment, $R^{N8}$ and $R^{N13}$ are each independently $C_{1-7}$alkyl (including, e.g., unsubstituted $C_{1-7}$alkyl, $C_{1-7}$haloalkyl, $C_{1-7}$hydroxyalkyl, $C_{1-7}$alkoxyalkyl, $C_{1-7}$carboxyalkyl, $C_{1-7}$aminoalkyl, $C_{5-20}$aryl-$C_{1-7}$alkyl); $C_{3-20}$heterocyclyl; or $C_{5-20}$aryl (including, e.g., $C_{5-20}$carboaryl, $C_{5-20}$heteroaryl, $C_{1-7}$alkyl-$C_{5-20}$aryl and $C_{5-20}$haloaryl)).

In one embodiment, $R^{N8}$ and $R^{N13}$ are each independently $C_{1-7}$alkyl (including, e.g., unsubstituted $C_{1-7}$alkyl, $C_{1-7}$haloalkyl, $C_{1-7}$hydroxyalkyl, $C_{1-7}$alkoxyalkyl, $C_{1-7}$carboxyalkyl, $C_{1-7}$aminoalkyl, $C_{5-20}$aryl-$C_{1-7}$alkyl).

In one embodiment, $R^{N8}$ and $R^{N13}$ are each independently $C_{1-4}$alkyl (including, e.g., unsubstituted $C_{1-4}$alkyl, $C_{1-4}$haloalkyl, $C_{1-4}$hydroxyalkyl, $C_{1-4}$alkoxyalkyl, $C_{1-4}$carboxyalkyl, $C_{1-4}$aminoalkyl, $C_{5-20}$aryl-$C_{1-7}$alkyl).

In one embodiment, $R^{N8}$ and $R^{N13}$ are each independently unsubstituted $C_{1-4}$alkyl, $C_{1-4}$haloalkyl, $C_{1-4}$hydroxyalkyl, $C_{1-4}$alkoxyalkyl, $C_{1-4}$carboxyalkyl, or $C_{1-4}$aminoalkyl.

In one embodiment, $R^{N8}$ and $R^{N13}$ are each independently:
-Me, -Et, -nPr, -iPr, -nBu, -tBu;
—$CF_3$, —$CHF_2$, —$CH_2F$, —$CCl_3$, —$CBr_3$, —$CH_2CH_2F$, —$CH_2CHF_2$, —$CH_2CF_3$;
—$CH_2OMe$, —$CH_2CH_2OMe$, —$CH(OH)CH_2OMe$;
—$CH_2OEt$, —$CH_2CH_2OEt$, —$CH(OH)CH_2OEt$;
—$CH_2OH$, —$CH_2CH_2OH$, —$CH(OH)CH_2OH$;
—$CH_2COOH$—$CH_2CH_2COOH$;
—$CH_2NH_2$, —$CH_2CH_2NH_2$, or —$CH_2CH_2NMe_2$.

In one embodiment, $R^{N8}$ and $R^{N13}$ are each independently: -Me, -Et, -nPr, -iPr, -nBu, or -tBu.

In one embodiment, $R^{N8}$ and $R^{N13}$ are each independently: -Me or -Et.

In one embodiment, $R^{N8}$ and $R^{N13}$ are each $C_1$alkyl (including, e.g., unsubstituted $C_1$alkyl and substituted $C_1$alkyl), for example, -Me, —$CF_3$, —$CHF_2$, —$CH_2F$, —$CH_2OH$, or —$CH_2NH_2$.

In one embodiment, $R^{N8}$ and $R^{N13}$ are each -Me.

In one embodiment, $R^{N8}$ and $R^{N13}$ are as defined in any of the above embodiments, with the proviso that $R^{N8}$ and $R^{N13}$ are not both -Et.

Ring Substituents

When not —H, each one of $R^A$, $R^B$, $R^C$, $R^{A1}$, $R^{A2}$, $R^{A3}$, $R^{A4}$, $R^{B5}$, $R^{B6}$, $R^{B7}$, $R^{C9}$, $R^{C10}$, $R^{C11}$, and $R^{C12}$ is independently a ring substituent.

Without wishing to be bound to any particular theory or mechanism for activity, it is believed that, in one preferred embodiment, any ring substituents are (a) are electron withdrawing groups; (b) do not adversely affect the planarity or near-planarity of the quino[4,3,2-kl]acridinium ion; or (c) both (a) and (b).

In one embodiment, when not —H, each one of $R^A$, $R^B$, $R^C$, $R^{A1}$, $R^{A2}$, $R^{A3}$, $R^{A4}$, $R^{B5}$, $R^{B6}$, $R^{B7}$, $R^{C9}$, $R^{C10}$, $R^{C11}$, and $R^{C12}$ is independently:
halo;
hydroxy;
ether (e.g., $C_{1-7}$alkoxy);
formyl;

acyl (e.g., $C_{1-7}$alkylacyl, $C_{5-20}$arylacyl);
carboxy;
ester;
acyloxy;
oxycarbonyloxy;
amido;
acylamido;
tetrazolyl;
amino (including, e.g., $C_{1-7}$aminoalkylamino);
nitro;
cyano;
azido;
sulfhydryl;
thioether (e.g., $C_{1-7}$alkylthio);
sulfonamido; or
$C_{1-7}$alkyl (including, e.g., unsubstituted $C_{1-7}$alkyl, $C_{1-7}$haloalkyl, $C_{1-7}$hydroxyalkyl, $C_{1-7}$carboxyalkyl, $C_{1-7}$acyloxyalkyl, $C_{1-7}$oxycarbonylalkyl, $C_{1-7}$oxycarbonyloxyalkyl, $C_{1-7}$aminoalkyl, $C_{1-7}$amidoalkyl, $C_{1-7}$acylamidoalkyl, $C_{1-7}$cyanoalkyl, $C_{5-20}$aryl-$C_{1-7}$alkyl, etc.).

In one embodiment, when not —H, each one of $R^A$, $R^B$, $R^C$, $R^{A1}$, $R^{A2}$, $R^{A3}$, $R^{A4}$, $R^{B5}$, $R^{B6}$, $R^{B7}$, $R^{C9}$, $R^{C10}$, $R^{C11}$, and $R^{C12}$ is independently selected from:
—F, —Cl, —Br, —I;
—OH;
—OMe, —OEt, —O(nPr), —O(iPr), —O(nBu), —O(tBu), —OCH$_2$Ph;
—OCF$_3$, —OCHF$_2$, —OCH$_2$F, —OCCl$_3$, —OCBr$_3$, —OCH$_2$CH$_2$F, —OCH$_2$CHF$_2$, —OCH$_2$CF$_3$;
C(=O)H;
—C(=O)Me, —C(=O)Et, —C(=O)(nPr), —C(=O)(iPr), —C(=O)(nBu), —C(=O)(tBu), —C(=O)Ph;
—C(=O)OH;
—C(=O)OMe, —C(=O)OEt, —C(=O)O(nPr), —C(=O)O(iPr), —C(=O)O(nBu), —C(=O)O(tBu);
—OC(=O)Me, —OC(=O)Et, —OC(=O)(nPr), —OC(=O)(iPr), —OC(=O)(nBu), —OC(=O)(tBu);
—OC(=O)OMe, —OC(=O)OEt, —OC(=O)O(nPr), —OC(=O)O(iPr), —OC(=O)O(nBu), —OC(=O)O(tBu);
—C(=O)NH$_2$, —C(=O)NHMe, —C(=O)NHEt, —C(=O)NH(nPr), —C(=O)NH(iPr), —C(=O)NH(nBu), —C(=O)NH(tBu), —C(=O)NMe$_2$, —C(=O)NEt$_2$, —C(=O)N(nPr)$_2$, —C(=O)N(iPr)$_2$, —C(=O)N(nBu)$_2$, —C(=O)N(tBu)$_2$;
—NHC(=O)Me, —NHC(=O)Et, —NHC(=O)(nPr), —NHC(=O)(iPr), —NHC(=O)(nBu), —NHC(=O)(tBu), —NHC(=O)Ph, succinimidyl, maleimidyl;
tetrazolyl;
—NH$_2$, —NHMe, —NHEt, —NH(nPr), —NH(iPr), —NH(nBu), —NH(tBu), —NMe$_2$, —NEt$_2$, —N(nPr)$_2$, —N(iPr)$_2$, —N(nBu)$_2$, —N(tBu)$_2$;
—NH(CH$_2$)$_2$NH$_2$, —NH(CH$_2$)$_3$NH$_2$, —NH(CH$_2$)$_4$NH$_2$, —NH(CH$_2$)$_5$NH$_2$, —NH(CH$_2$)$_6$NH$_2$, —NHCH$_2$NH(Me), —NH(CH$_2$)$_2$NH(Me), —NH(CH$_2$)$_3$NH(Me), —NH(CH$_2$)$_4$NH(Me), —NH(CH$_2$)$_5$NH(Me), —NH(CH$_2$)$_6$NH(Me), —NHCH$_2$NH(Et), —NH(CH$_2$)$_2$NH(Et), —NH(CH$_2$)$_3$NH(Et), —NH(CH$_2$)$_4$NH(Et), —NH(CH$_2$)$_5$NH(Et), —NH(CH$_2$)$_6$NH(Et);
—NO$_2$;
—CN;
—N$_3$;
—SH;
—SMe, —SEt, —S(nPr), —S(iPr), —S(nBu), —S(tBu), —SCH$_2$Ph;
—S(=O)$_2$NH$_2$, —S(=O)$_2$NHMe, —S(=O)$_2$NMe$_2$, —S(=O)$_2$NHEt, —S(=O)$_2$NEt$_2$, —S(=O)$_2$NH(nPr), —S(=O)$_2$N(nPr)$_2$, —S(=O)$_2$NH(iPr), —S(=O)$_2$N(iPr)$_2$, —S(=O)$_2$NH(nBu), —S(=O)$_2$N(nBu)$_2$, —S(=O)$_2$NH(tBu), —S(=O)$_2$N(tBu)$_2$, —S(=O)$_2$NHPh;
-Me, -Et, -nPr, -iPr, -nBu, -tBu;
—CF$_3$, —CHF$_2$, —CH$_2$F, —CCl$_3$, —CBr$_3$, —CH$_2$CH$_2$F, —CH$_2$CHF$_2$, —CH$_2$CF$_3$;
—CH$_2$OH, —CH$_2$CH$_2$OH, —CH(OH)CH$_2$OH;
—CH$_2$COOH, —CH$_2$CH$_2$COOH, —CH$_2$CH$_2$CH$_2$COOH;
—CH$_2$OC(=O)Me, —CH$_2$CH$_2$OC(=O)Me, —CH=CHOC(=O)Me;
—CH$_2$C(=O)OMe, —CH$_2$CH$_2$C(=O)OMe, —CH=CHC(=O)OMe;
—CH$_2$OC(=O)OMe, —CH$_2$CH$_2$OC(=O)OMe, —CH=CHOC(=O)OMe;
—CH$_2$NH$_2$, —CH$_2$CH$_2$NH$_2$, —CH=CHNH$_2$, —CH$_2$CH$_2$NMe$_2$;
—CH$_2$NHC(=O)Me, —CH$_2$CH$_2$NHC(=O)Me, —CH=CHNHC(=O)Me;
—CH$_2$C(=O)NH$_2$, —CH$_2$CH$_2$C(=O)NH$_2$, —CH=CHC(=O)NH$_2$;
—CH$_2$CN, —CH$_2$CH$_2$CN, —CH=CHCN.

In one embodiment, when not —H, each one of $R^A$, $R^B$, $R^C$, $R^{A1}$, $R^{A2}$, $R^{A3}$, $R^{A4}$, $R^{B5}$, $R^{B6}$, $R^{B7}$, $R^{C9}$, $R^{C10}$, $R^{C11}$, and $R^{C12}$ is independently:
halo;
ether (e.g., $C_{1-7}$alkoxy);
ester;
acyloxy;
oxycarbonyloxy;
amido;
acylamido;
amino (including, e.g., $C_{1-7}$aminoalkylamino);
nitro;
cyano;
azido; or,
$C_{1-7}$alkyl (including, e.g., unsubstituted $C_{1-7}$alkyl, $C_{1-7}$haloalkyl, $C_{1-7}$hydroxyalkyl, $C_{1-7}$carboxyalkyl, $C_{1-7}$acyloxyalkyl, $C_{1-7}$oxycarbonylalkyl, $C_{1-7}$oxycarbonyloxyalkyl, $C_{1-7}$aminoalkyl, $C_{1-7}$amidoalkyl, $C_{1-7}$acylamidoalkyl, $C_{1-7}$cyanoalkyl, $C_{5-20}$aryl-$C_{1-7}$alkyl, etc.).

In one embodiment, when not —H, each one of $R^A$, $R^B$, $R^C$, $R^{A1}$, $R^{A2}$, $R^{A3}$, $R^{A4}$, $R^{B5}$, $R^{B6}$, $R^{B7}$, $R^{C9}$, $R^{C10}$, $R^{C11}$, and $R^{C12}$ is independently:
—F, —Cl, —Br, —I;
—OMe, —OEt, —O(nPr), —O(iPr), —O(nBu), —O(tBu), —OCH$_2$Ph;
—OCF$_3$, —OCHF$_2$, —OCH$_2$F, —OCCl$_3$, —OCBr$_3$, —OCH$_2$CH$_2$F, —OCH$_2$CHF$_2$, —OCH$_2$CF$_3$;
—C(=O)Me, —C(=O)Et, —C(=O)(nPr), —C(=O)(iPr), —C(=O)(nBu), —C(=O)(tBu), —C(=O)Ph;
—C(=O)OMe, —C(=O)OEt, —C(=O)O(nPr), —C(=O)O(iPr), —C(=O)O(nBu), —C(=O)O(tBu);
—OC(=O)Me, —OC(=O)Et, —OC(=O)(nPr), —OC(=O)(iPr), —OC(=O)(nBu), —OC(=O)(tBu);
—OC(=O)OMe, —OC(=O)OEt, —OC(=O)O(nPr), —OC(=O)O(iPr), —OC(=O)O(nBu), —OC(=O)O(tBu);
—C(=O)NH$_2$, —C(=O)NHMe, —C(=O)NHEt, —C(=O)NH(nPr), —C(=O)NH(iPr), —C(=O)NH(nBu), —C(=O)NH(tBu), —C(=O)NMe$_2$, —C(=O)NEt$_2$, —C(=O)N(nPr)$_2$, —C(=O)N(iPr)$_2$, —C(=O)N(nBu)$_2$, —C(=O)N(tBu)$_2$;

—NHC(=O)Me, —NHC(=O)Et, —NHC(=O)(nPr), —NHC(=O)(iPr), —NHC(=O)(nBu), —NHC(=O)(tBu), —NHC(=O)Ph, succinimidyl, maleimidyl;

—NH$_2$, —NHMe, —NHEt, —NH(nPr), —NH(iPr), —NH(nBu), —NH(tBu), —NMe$_2$, —NEt$_2$, —N(nPr)$_2$, —N(iPr)$_2$, —N(nBu)$_2$, —N(tBu)$_2$;

—NH(CH$_2$)$_2$NH$_2$, —NH(CH$_2$)$_3$NH$_2$, —NH(CH$_2$)$_4$NH$_2$, —NH(CH$_2$)$_5$NH$_2$, —NH(CH$_2$)$_6$NH$_2$, —NHCH$_2$NH(Me), —NH(CH$_2$)$_2$NH(Me), —NH(CH$_2$)$_3$NH(Me), —NH(CH$_2$)$_4$NH(Me), —NH(CH$_2$)$_5$NH(Me), —NH(CH$_2$)$_6$NH(Me), —NHCH$_2$NH(Et), —NH(CH$_2$)$_2$NH(Et), —NH(CH$_2$)$_3$NH(Et), —NH(CH$_2$)$_4$NH(Et), —NH(CH$_2$)$_5$NH(Et), —NH(CH$_2$)$_6$NH(Et);

—NO$_2$;

—CN;

—N$_3$;

-Me, -Et, -nPr, -iPr, -nBu, -tBu;

—CF$_3$, —CHF$_2$, —CH$_2$F, —CCl$_3$, —CBr$_3$, —CH$_2$CH$_2$F, —CH$_2$CHF$_2$, —CH$_2$CF$_3$;

—CH$_2$OH, —CH$_2$CH$_2$OH, —CH(OH)CH$_2$OH;

—CH$_2$COOH, —CH$_2$CH$_2$COOH, —CH$_2$CH$_2$CH$_2$COOH;

—CH$_2$OC(=O)Me, —CH$_2$CH$_2$OC(=O)Me, —CH=CHOC(=O)Me;

—CH$_2$C(=O)OMe, —CH$_2$CH$_2$C(=O)OMe, —CH=CHC(=O)OMe;

—CH$_2$OC(=O)OMe, —CH$_2$CH$_2$OC(=O)OMe, —CH=CHOC(=O)OMe;

—CH$_2$NH$_2$, —CH$_2$CH$_2$NH$_2$, —CH=CHNH$_2$, —CH$_2$CH$_2$NMe$_2$;

—CH$_2$NHC(=O)Me, —CH$_2$CH$_2$NHC(=O)Me, —CH=CHNHC(=O)Me;

—CH$_2$C(=O)NH$_2$, —CH$_2$CH$_2$C(=O)NH$_2$, —CH=CHC(=O)NH$_2$;

—CH$_2$CN, —CH$_2$CH$_2$CN, —CH=CHCN.

In one embodiment, when not —H, each one of $R^A$, $R^B$, $R^C$, $R^{A1}$, $R^{A2}$, $R^{A3}$, $R^{A4}$, $R^{B5}$, $R^{B6}$, $R^{B7}$, $R^{C9}$, $R^{C10}$, $R^{C11}$, and $R^{C12}$ is independently:

halo;

C$_{1-7}$alkoxy;

ester;

acyloxy;

oxycarbonyloxy;

acylamido;

amino (including, e.g., C$_{1-7}$aminoalkylamino);

nitro;

cyano;

azido; or,

C$_{1-7}$alkyl (including, e.g., unsubstituted C$_{1-7}$alkyl, C$_{1-7}$haloalkyl, C$_{1-7}$hydroxyalkyl, C$_{1-7}$carboxyalkyl, C$_{1-7}$acyloxyalkyl, C$_{1-7}$oxycarbonylalkyl, C$_{1-7}$oxycarbonyloxyalkyl, C$_{1-7}$aminoalkyl, C$_{1-7}$amidoalkyl, C$_{1-7}$acylamidoalkyl, C$_{1-7}$cyanoalkyl, C$_{5-20}$aryl-C$_{1-7}$alkyl, etc.).

In one embodiment, when not —H, each one of $R^A$, $R^B$, $R^C$, $R^{A1}$, $R^{A2}$, $R^{A3}$, $R^{A4}$, $R^{B5}$, $R^{B6}$, $R^{B7}$, $R^{C9}$, $R^{C10}$, $R^{C11}$, and $R^{C12}$ is independently selected from:

—F, —Cl, —Br, —I;

—OMe, —OEt, —O(nPr), —O(iPr), —O(nBu), —O(tBu), —OCH$_2$Ph;

—OCF$_3$, —OCHF$_2$, —OCH$_2$F, —OCCl$_3$, —OCBr$_3$, —OCH$_2$CH$_2$F, —OCH$_2$CHF$_2$, —OCH$_2$CF$_3$;

—C(=O)OMe, —C(=O)OEt, —C(=O)O(nPr), —C(=O)O(iPr), —C(=O)O(nBu), —C(=O)O(tBu);

—OC(=O)Me, —OC(=O)Et, —OC(=O)(nPr), —OC(=O)(iPr), —OC(=O)(nBu), —OC(=O)(tBu);

—OC(=O)OMe, —OC(=O)OEt, —OC(=O)O(nPr), —OC(=O)O(iPr), —OC(=O)O(nBu), —OC(=O)O(tBu);

—NHC(=O)Me, —NHC(=O)Et, —NHC(=O)(nPr), —NHC(=O)(iPr), —NHC(=O)(nBu), —NHC(=O)(tBu), —NHC(=O)Ph, succinimidyl, maleimidyl;

—NH$_2$, —NHMe, —NHEt, —NH(nPr), —NH(iPr), —NH(nBu), —NH(tBu), —NMe$_2$, —NEt$_2$, —N(nPr)$_2$, —N(iPr)$_2$, —N(nBu)$_2$, —N(tBu)$_2$;

—NH(CH$_2$)$_2$NH$_2$, —NH(CH$_2$)$_3$NH$_2$, —NH(CH$_2$)$_4$NH$_2$, —NH(CH$_2$)$_5$NH$_2$, —NH(CH$_2$)$_6$NH$_2$, —NHCH$_2$NH(Me), —NH(CH$_2$)$_2$NH(Me), —NH(CH$_2$)$_3$NH(Me), —NH(CH$_2$)$_4$NH(Me), —NH(CH$_2$)$_5$NH(Me), —NH(CH$_2$)$_6$NH(Me), —NHCH$_2$NH(Et), —NH(CH$_2$)$_2$NH(Et), —NH(CH$_2$)$_3$NH(Et), —NH(CH$_2$)$_4$NH(Et), —NH(CH$_2$)$_5$NH(Et), —NH(CH$_2$)$_6$NH(Et);

—NO$_2$;

—CN;

—N$_3$;

-Me, -Et, -nPr, -iPr, -nBu, -tBu;

—CF$_3$, —CHF$_2$, —CH$_2$F, —CCl$_3$, —CBr$_3$, —CH$_2$CH$_2$F, —CH$_2$CHF$_2$, —CH$_2$CF$_3$;

—CH$_2$OH, —CH$_2$CH$_2$OH, —CH(OH)CH$_2$OH;

—CH$_2$COOH, —CH$_2$CH$_2$COOH, —CH$_2$CH$_2$CH$_2$COOH;

—CH$_2$OC(=O)Me, —CH$_2$CH$_2$OC(=O)Me, —CH=CHOC(=O)Me;

—CH$_2$C(=O)OMe, —CH$_2$CH$_2$C(=O)OMe, —CH=CHC(=O)OMe;

—CH$_2$OC(=O)OMe, —CH$_2$CH$_2$OC(=O)OMe, —CH=CHOC(=O)OMe;

—CH$_2$NH$_2$, —CH$_2$CH$_2$NH$_2$, —CH=CHNH$_2$, —CH$_2$CH$_2$NMe$_2$;

—CH$_2$NHC(=O)Me, —CH$_2$CH$_2$NHC(=O)Me, —CH=CHNHC(=O)Me;

—CH$_2$C(=O)NH$_2$, —CH$_2$CH$_2$C(=O)NH$_2$, —CH=CHC(=O)NH$_2$;

—CH$_2$CN, —CH$_2$CH$_2$CN, —CH=CHCN.

In one embodiment, when not —H, each one of $R^A$, $R^B$, $R^C$, $R^{A1}$, $R^{A2}$, $R^{A3}$, $R^{A4}$, $R^{B5}$, $R^{B6}$, $R^{B7}$, $R^{C9}$, $R^{C10}$, $R^{C11}$, and $R^{C12}$ is independently:

halo;

ether (e.g., C$_{1-7}$alkoxy);

ester;

acyloxy;

oxycarbonyloxy;

cyano; or,

C$_{1-7}$alkyl (including, e.g., unsubstituted C$_{1-7}$alkyl, C$_{1-7}$haloalkyl, C$_{1-7}$hydroxyalkyl, C$_{1-7}$carboxyalkyl, C$_{1-7}$acyloxyalkyl, C$_{1-7}$oxycarbonylalkyl, C$_{1-7}$oxycarbonyloxyalkyl, C$_{1-7}$aminoalkyl, C$_{1-7}$amidoalkyl, C$_{1-7}$acylamidoalkyl, C$_{1-7}$cyanoalkyl, C$_{5-20}$aryl-C$_{1-7}$alkyl, etc.).

In one embodiment, when not —H, each one of $R^A$, $R^B$, $R^C$, $R^{A1}$, $R^{A2}$, $R^{A3}$, $R^{A4}$, $R^{B5}$, $R^{B6}$, $R^{B7}$, $R^{C9}$, $R^{C10}$, $R^{C11}$, and $R^{C12}$ is independently:

—F, —Cl, -Me, —OMe, —CN,

—C(=O)OMe, —OC(=O)Me, —OC(=O)OMe,

—CH$_2$CH$_2$C(=O)OMe,

—CH$_2$CH$_2$OC(=O)Me,

—CH=CHC(=O)OMe,

—CH=CHOC(=O)Me,

—CH=CHC(=O)NH$_2$,

—CH=CHC(=O)(morpholin-4-yl),

—CH=CHCH$_2$NHC(=O)CF$_3$,

—CH=CHCN, or

—C≡CCH$_2$NHC(=O)CF$_3$.

In one embodiment, when not —H, each one of $R^A$, $R^B$, $R^C$, $R^{A1}$, $R^{A2}$, $R^{A3}$, $R^{A4}$, $R^{B5}$, $R^{B6}$, $R^{B7}$, $R^{C9}$, $R^{C10}$, $R^{C11}$, and $R^{C12}$ is independently: —F, —Cl, -Me, —OMe, —C(=O)OMe, —OC(=O)Me, or —OC(=O)OMe.

In one embodiment, when not —H, each one of $R^A$, $R^B$, $R^C$, $R^{A1}$, $R^{A2}$, $R^{A3}$, $R^{A4}$, $R^{B5}$, $R^{B6}$, $R^{B7}$, $R^{C9}$, $R^{C10}$, $R^{C11}$, and $R^{C12}$ is independently: —F, —Cl, -Me, —OMe, or —CH$_2$CH$_2$COOMe.

Anions

The quino[4,3,2-kl]acridinium salts of the present invention comprise (i) a quino[4,3,2-kl]acridinium cation, and (ii) one or more anions, collectively denoted herein as Q⁻.

The quino[4,3,2-kl]acridinium cation carries a+1 charge. The anion may carry a −1 charge, in which case the molar ratio of anion:cation is 1:1. Alternatively, the anion may carry a more negative charge (e.g., −2, −3), in which case the molar ratio of anion:cation is determined accordingly (e.g., 1:2, 1:3, respectively). The anions may be a mixture, for example, a mixture of anions carrying a −1 charge (e.g., Cl⁻ and I⁻), in which case the molar ratio of anion:cation is still 1:1; or a mixture of anions carrying different charges.

In one embodiment, the anion is independently derived from one or more of: the following inorganic acids: hydrochloric, hydrobromic, hydroiodic, sulfuric, sulfurous, nitric, nitrous, phosphoric, and phosphorous; the following organic acids: acetic, propionic, succinic, gycolic, stearic, lactic, malic, tartaric, citric, ascorbic, maleic, hydroxymaleic, phenylacetic, glutamic, benzoic, salicylic, sulfanilic, 2-acetyoxybenzoic, fumaric, toluenesulfonic, methanesulfonic, ethanesulfonic, ethane disulfonic, oxalic, isethionic, and valeric; and the following polymeric acids: tannic acid, carboxymethyl cellulose.

In one embodiment, the anion is independently derived from one or more of: the following inorganic acids: hydrochloric, hydrobromic, hydroiodic; and the following organic acids: methanesulfonic, ethanesulfonic, isethionic, fumaric, or gluconic.

In one embodiment, the anion independently is chloride, bromide, iodide, methylsulfate (i.e., MeOSO$_3$⁻), ethylsulfate (i.e., EtOSO$_3$⁻), isethionate, fumarate, or gluconate.

In one embodiment, the anion is independently iodide or methylsulfate (i.e., MeOSO$_3$⁻).

In one embodiment, the anion is methylsulfate.

In one embodiment, the anion is iodide.

Some Specific Embodiments

Some specific embodiments of the present invention are shown below.

1      9   RHPS01

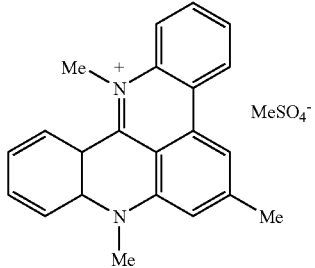

2      10   RHPS02

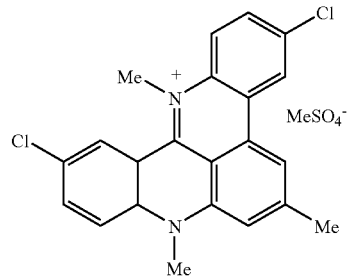

3      11   RHPS03

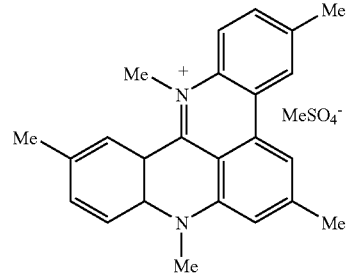

-continued
| | | | |
|---|---|---|---|
| 4 | 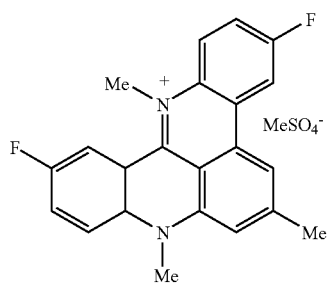 | 12 | RHPS04 |
| 5 | 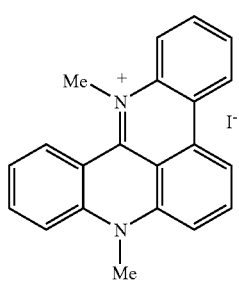 | 55 | RHPS05 |
| 6 | 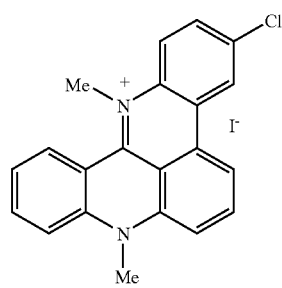 | 56 | RHPS06 |
| 7 | 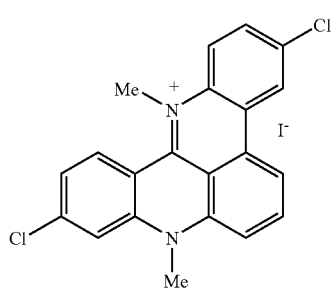 | 58 | RHPS07 |
| 8 | 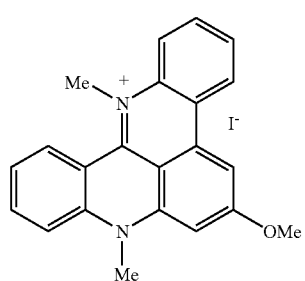 | 59 | RHPS08 |

-continued
| | | | |
|---|---|---|---|
| 16 | 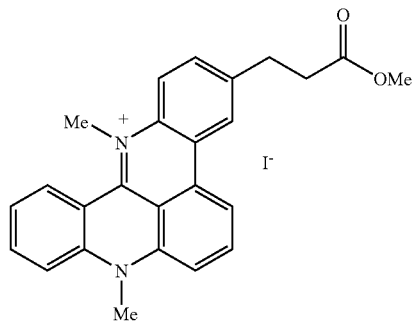 | 65 | RHPS09 |
| 9 | 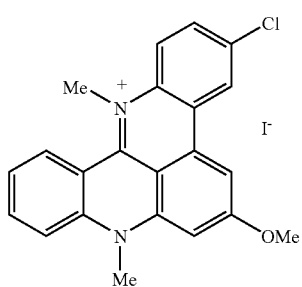 | 60 | RHPS10 |
| 10 | 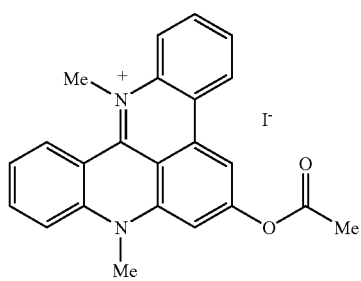 | 63 | RHPS11 |
| 11 | 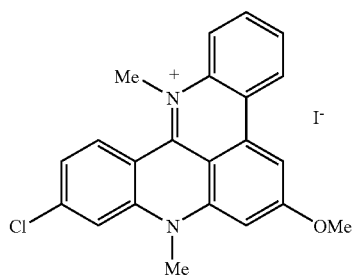 | 61 | RHPS12 |
| 12 | 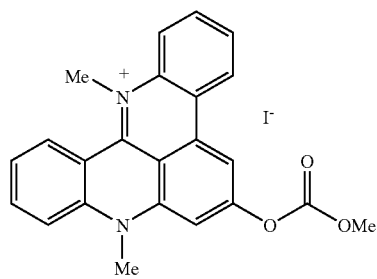 | 62 | RHPS13 |

-continued
| | | | |
|---|---|---|---|
| 13 | 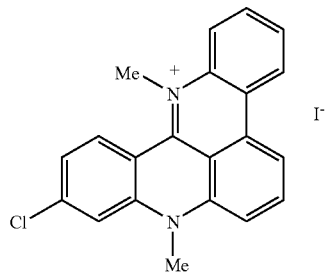 | 57 | RHPS14 |
| 14 | 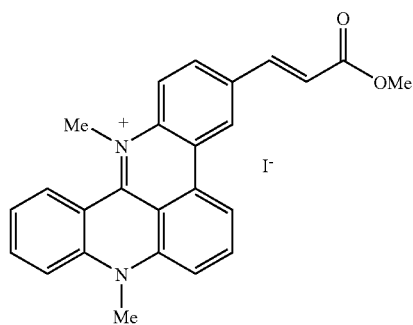 | 64 | RHPS15 |
| 15 | 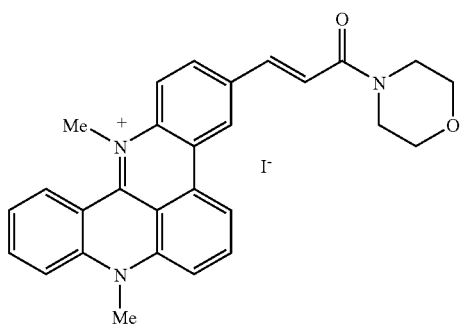 | 66 | RHPS16 |
| 17 | 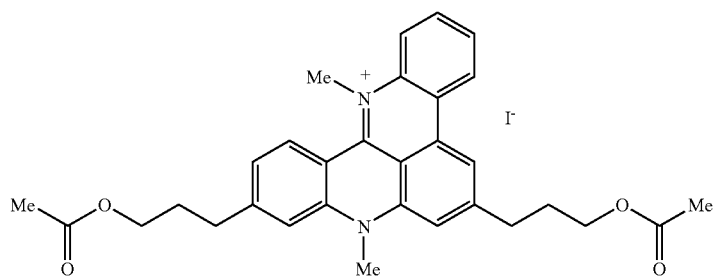 | 71 | RHPS17 |
| 18 | 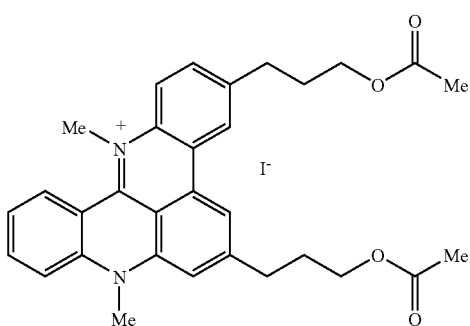 | 70 | RHPS18 |

-continued

| 19 | 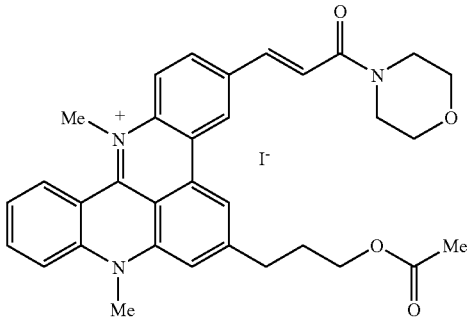 | 69 | RHPS19 |
| 20 | 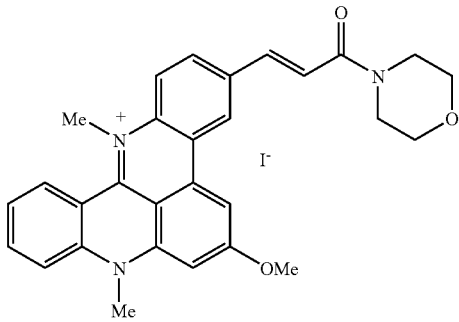 | | RHPS20 |
| 21 | 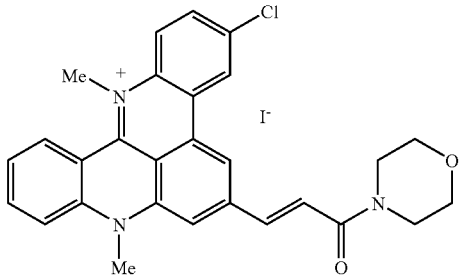 | 67 | RHPS21 |
| 22 | 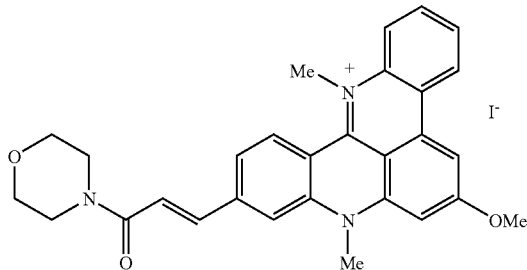 | 68 | RHPS22 |

Chemical Terms

The term "carbo," "carbyl," "hydrocarbon" and "hydrocarbyl," as used herein, pertain to compounds and/or groups which have only carbon and hydrogen atoms.

The term "hetero," as used herein, pertains to compounds and/or groups which have at least one heteroatom, for example, multivalent heteroatoms (which are also suitable as ring heteroatoms) such as boron, silicon, nitrogen, phosphorus, oxygen, and sulfur, and monovalent heteroatoms, such as fluorine, chlorine, bromine, and iodine.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

The term "cyclic," as used herein, pertains to compounds and/or groups which have one ring, or two or more rings (e.g., spiro, fused, bridged).

The term "ring," as used herein, pertains to a closed ring of from 3 to 10 covalently linked atoms, more preferably 3 to 8 covalently linked atoms.

The term "aromatic ring," as used herein, pertains to a closed ring of from 3 to 10 covalently linked atoms, more preferably 5 to 8 covalently linked atoms, more preferably 5 or 6 covalently linked atoms, which ring is aromatic.

The term "heterocyclic ring," as used herein, pertains to a closed ring of from 3 to 10 covalently linked atoms, more preferably 3 to 8 covalently linked atoms, wherein at least one of the ring atoms is a multivalent ring heteroatom, for example, nitrogen, phosphorus, silicon, oxygen, and sulfur, though more commonly nitrogen, oxygen, and sulfur.

The term "alicyclic," as used herein, pertains to compounds and/or groups which have one ring, or two or more rings (e.g., spiro, fused, bridged), wherein said ring(s) are not aromatic.

The term "aromatic," as used herein, pertains to compounds and/or groups which have one ring, or two or more rings (e.g., fused), wherein said ring(s) are aromatic.

The term "heterocyclic," as used herein, pertains to cyclic compounds and/or groups which have one heterocyclic ring, or two or more heterocyclic rings (e.g., spiro, fused, bridged), wherein said ring(s) may be alicyclic or aromatic.

The term "heteroaromatic," as used herein, pertains to cyclic compounds and/or groups which have one heterocyclic ring, or two or more heterocyclic rings (e.g., fused), wherein said ring(s) is aromatic.

Substituents

The phrase "optionally substituted," as used herein, pertains to a parent group which may be unsubstituted or which may be substituted.

Unless otherwise specified, the term "substituted," as used herein, pertains to a parent group which bears one or more substituents. The term "substituent" is used herein in the conventional sense and refers to a chemical moiety which is covalently attached to, appended to, or if appropriate, fused to, a parent group. A wide variety of substituents are well known, and methods for their formation and introduction into a variety of parent groups are also well known.

The substituents are described in more detail below.

$C_{1-7}$alkyl: The term "$C_{1-7}$alkyl," as used herein, pertains to a monovalent moiety obtained by removing a hydrogen atom from a $C_{1-7}$hydrocarbon compound having from 1 to 7 carbon atoms, which may be aliphatic or alicyclic, or a combination thereof, and which may be saturated, partially unsaturated, or fully unsaturated. The term "$C_{1-4}$alkyl" (and similar terms), as used herein, pertains to analogous moieties having from 1 to 4 carbon atoms.

Examples of (unsubstituted) saturated linear $C_{1-7}$alkyl groups include, but are not limited to, methyl, ethyl, n-propyl, n-butyl, and n-pentyl (amyl).

Examples of (unsubstituted) saturated branched $C_{1-7}$alkyl groups include, but are not limited to, iso-propyl, iso-butyl, sec-butyl, tert-butyl, and neo-pentyl.

Examples of saturated alicyclic (carbocyclic) $C_{1-7}$alkyl groups (also referred to as "$C_{3-7}$cycloalkyl" groups) include, but are not limited to, unsubstituted groups such as cyclopropyl, cyclobutyl, cyclopentyl, and cyclohexyl, as well as substituted groups (e.g., groups which comprise such groups), such as methylcyclopropyl, dimethylcyclopropyl, methylcyclobutyl, dimethylcyclobutyl, methylcyclopentyl, dimethylcyclopentyl, methylcyclohexyl, dimethylcyclohexyl, cyclopropylmethyl and cyclohexylmethyl.

Examples of (unsubstituted) unsaturated $C_{1-7}$alkyl groups which have one or more carbon-carbon double bonds (also referred to as "$C_{2-7}$alkenyl" groups) include, but are not limited to, ethenyl (vinyl, —CH=CH$_2$), 2-propenyl (allyl, —CH—CH=CH$_2$), isopropenyl (—C(CH$_3$)=CH$_2$), butenyl, pentenyl, and hexenyl.

Examples of (unsubstituted) unsaturated $C_{1-7}$alkyl groups which have one or more carbon-carbon triple bonds (also referred to as "$C_{2-7}$alkynyl" groups) include, but are not limited to, ethynyl (ethinyl) and 2-propynyl (propargyl).

Examples of unsaturated alicyclic (carbocyclic) $C_{1-7}$alkyl groups which have one or more carbon-carbon double bonds (also referred to as "$C_{3-7}$cycloalkenyl" groups) include, but are not limited to, unsubstituted groups such as cyclopropenyl, cyclobutenyl, cyclopentenyl, and cyclohexenyl, as well as substituted groups (e.g., groups which comprise such groups) such as cyclopropenylmethyl and cyclohexenylmethyl.

$C_{3-20}$heterocyclyl: The term "$C_{3-20}$heterocyclyl," as used herein, pertains to a monovalent moiety obtained by removing a hydrogen atom from a ring atom of a $C_{3-20}$heterocyclic compound, said compound having one ring, or two or more rings (e.g., spiro, fused, bridged), and having from 3 to 20 ring atoms, atoms, of which from 1 to 10 are ring heteroatoms, and wherein at least one of said ring(s) is a heterocyclic ring. Preferably, each ring has from 3 to 7 ring atoms, of which from 1 to 4 are ring heteroatoms. "$C_{3-20}$" denotes ring atoms, whether carbon atoms or heteroatoms.

Examples of (non-aromatic) monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted (non-aromatic) monocyclic heterocyclyl groups include saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

Examples of heterocyclyl groups which are also heteroaryl groups are described below with aryl groups.

$C_{5-20}$aryl: The term "$C_{5-20}$aryl," as used herein, pertains to a monovalent moiety obtained by removing a hydrogen atom from an aromatic ring atom of a $C_{5-20}$aromatic compound, said compound having one ring, or two or more rings (e.g., fused), and having from 5 to 20 ring atoms, and wherein at least one of said ring(s) is an aromatic ring. Preferably, each ring has from 5 to 7 ring atoms.

The ring atoms may be all carbon atoms, as in "carboaryl groups," in which case the group may conveniently be referred to as a "$C_{5-20}$carboaryl" group.

Examples of carboaryl groups include, but are not limited to, those derived from benzene (i.e., phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indene ($C_9$), isoindene ($C_9$), and fluorene ($C_{13}$).

Alternatively, the ring atoms may include one or more heteroatoms, including but not limited to oxygen, nitrogen, and sulfur, as in "heteroaryl groups." In this case, the group may conveniently be referred to as a "$C_{5-20}$heteroaryl" group, wherein "$C_{5-20}$" denotes ring atoms, whether carbon atoms or heteroatoms. Preferably, each ring has from 5 to 7 ring atoms, of which from 0 to 4 are ring heteroatoms.

Examples of monocyclic heteroaryl groups include, but are not limited to, those derived from:

$N_1$: pyrrole (azole) ($C_5$), pyridine (azine) ($C_6$);
$O_1$: furan (oxole) ($C_5$);
$S_1$: thiophene (thiole) ($C_5$);
$N_1O_1$: oxazole ($C_5$), isoxazole ($C_5$), isoxazine ($C_6$);
$N_2O_1$: oxadiazole (furazan) ($C_5$);
$N_3O_1$: oxatriazole ($C_5$);
$N_1S_1$: thiazole ($C_5$), isothiazole ($C_5$);
$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);
$N_3$: triazole ($C_5$), triazine ($C_6$); and,
$N_4$: tetrazole ($C_5$).

Examples of heterocyclic groups (some of which are also heteroaryl groups) which comprise fused rings, include, but are not limited to:

$C_9$heterocyclic groups (with 2 fused rings) derived from benzofuran ($O_1$), isobenzofuran ($O_1$), indole ($N_1$), isoindole ($N_1$), purine ($N_4$) (e.g., adenine, guanine), benzimidazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$heterocyclic groups (with 2 fused rings) derived from benzodioxan ($O_2$), quinoline ($N_1$), isoquinoline ($N_1$), benzoxazine ($N_1O_1$), benzodiazine ($N_2$), pyridopyridine ($N_2$), quinoxaline ($N_2$), quinazoline ($N_2$);

$C_{13}$heterocyclic groups (with 3 fused rings) derived from carbazole ($N_1$), dibenzofuran ($O_1$), dibenzothiophene ($S_1$); and, $C_{14}$heterocyclic groups (with 3 fused rings) derived from acridine ($N_1$), xanthene ($O_1$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

Heterocyclic groups (including heteroaryl groups) which have a nitrogen ring atom in the form of an —NH— group may be N-substituted, that is, as —NR—. For example, pyrrole may be N-methyl substituted, to give N-methypyrrole. Examples of N-substitutents include, but are not limited to $C_{1-7}$alkyl, $C_{3-20}$heterocyclyl, $C_{5-20}$aryl, and acyl groups.

Heterocyclic groups (including heteroaryl groups) which have a nitrogen ring atom in the form of an —N= group may be substituted in the form of an N-oxide, that is, as —N(→O)= (also denoted —N⁺(→O⁻)=). For example, quinoline may be substituted to give quinoline N-oxide; pyridine to give pyridine N-oxide; benzofurazan to give benzofurazan N-oxide (also known as benzofuroxan).

Cyclic groups may additionally bear one or more oxo (=O) groups on ring carbon atoms. Monocyclic examples of such groups include, but are not limited to, those derived from:

$C_5$: cyclopentanone, cyclopentenone, cyclopentadienone;
$C_6$: cyclohexanone, cyclohexenone, cyclohexadienone;
$O_1$: furanone ($C_5$), pyrone ($C_6$);
$N_1$: pyrrolidone (pyrrolidinone) ($C_5$), piperidinone (piperidone) ($C_6$), piperidinedione ($C_6$);
$N_2$: imidazolidone (imidazolidinone) ($C_5$), pyrazolone (pyrazolinone) ($C_5$), piperazinone ($C_6$), piperazinedione ($C_6$), pyridazinone ($C_6$), pyrimidinone ($C_6$) (e.g., cytosine), pyrimidinedione ($C_6$) (e.g., thymine, uracil), barbituric acid ($C_6$);
$N_1S_1$: thiazolone ($C_5$), isothiazolone ($C_5$);
$N_1O_1$: oxazolinone ($C_5$).

Polycyclic examples of such groups include, but are not limited to, those derived from:
$C_9$: indenedione;
$N_1$: oxindole ($C_9$);
$O_1$: benzopyrone (e.g., coumarin, isocoumarin, chromone) ($C_{10}$);
$N_1O_1$: benzoxazolinone ($C_9$), benzoxazolinone ($C_{10}$);
$N_2$: quinazolinedione ($C_{10}$);
$N_4$: purinone ($C_9$) (e.g., guanine).

Still more examples of cyclic groups which bear one or more oxo (=O) groups on ring carbon atoms include, but are not limited to, those derived from:

cyclic anhydrides (—C(=O)—O—C(=O)— in a ring), including but not limited to maleic anhydride ($C_5$), succinic anhydride ($C_5$), and glutaric anhydride ($C_6$);

cyclic carbonates (—O—C(=O)—O— in a ring), such as ethylene carbonate ($C_5$) and 1,2-propylene carbonate ($C_5$);

imides (—C(=O)—NR—C(=O)— in a ring), including but not limited to, succinimide ($C_5$), maleimide ($C_5$), phthalimide, and glutarimide ($C_6$);

lactones (cyclic esters, —O—C(=O)— in a ring), including, but not limited to, β-propiolactone, γ-butyrolactone, δ-valerolactone (2-piperidone), and ε-caprolactone;

lactams (cyclic amides, —NR—C(=O)— in a ring), including, but not limited to, β-propiolactam ($C_4$), γ-butyrolactam (2-pyrrolidone) ($C_5$), δ-valerolactam ($C_6$), and ε-caprolactam ($C_7$);

cyclic carbamates (—O—C(=O)—NR— in a ring), such as 2-oxazolidone ($C_5$);

cyclic ureas (—NR—C(=O)—NR— in a ring), such as 2-imidazolidone ($C_5$) and pyrimidine-2,4-dione (e.g., thymine, uracil) ($C_6$).

The above $C_{1-7}$alkyl, $C_{3-20}$heterocyclyl, and $C_{5-20}$aryl groups, whether alone or part of another substituent, may themselves optionally be substituted with one or more groups selected from themselves and the additional substituents listed below.

Hydrogen: —H. Note that if the substituent at a particular position is hydrogen, it may be convenient to refer to the compound as being "unsubstituted" at that position.

Halo: —F, —Cl, —Br, and —I.

Hydroxy: —OH.

Ether: —OR, wherein R is an ether substituent, for example, a $C_{1-7}$alkyl group (also referred to as a $C_{1-7}$alkoxy group, discussed below), a $C_{3-20}$heterocyclyl group (also referred to as a $C_{3-20}$heterocyclyloxy group), or a $C_{5-20}$aryl group (also referred to as a $C_{5-20}$aryloxy group), preferably a $C_{1-7}$alkyl group.

$C_{1-7}$alkoxy: —OR, wherein R is a $C_{1-7}$alkyl group. Examples of $C_{1-7}$alkoxy groups include, but are not limited to, —OCH$_3$ (methoxy), —OCH$_2$CH$_3$ (ethoxy) and —OC(CH$_3$)$_3$ (tert-butoxy).

Oxo (keto, -one): =O.

Formyl (carbaldehyde, carboxaldehyde): —C(=O)H.

Acyl (keto): —C(=O)R, wherein R is an acyl substituent, for example, a $C_{1-7}$alkyl group (also referred to as $C_{1-7}$alkylacyl or $C_{1-7}$alkanoyl), a $C_{3-20}$heterocyclyl group (also referred to as $C_{3-20}$heterocyclylacyl), or a $C_{5-20}$aryl group (also referred to as $C_{5-20}$arylacyl), preferably a $C_{1-7}$alkyl group. Examples of acyl groups include, but are not limited to, —C(=O)CH$_3$ (acetyl), —C(=O)CH$_2$CH$_3$ (propionyl), —C(=O)C(CH$_3$)$_3$ (butyryl), and —C(=O)Ph (benzoyl, phenone).

Carboxy (carboxylic acid): —COOH.

Ester (carboxylate, carboxylic acid ester, oxycarbonyl): —C(=O)OR, wherein R is an ester substituent, for example, a $C_{1-7}$alkyl group, a $C_{3-20}$heterocyclyl group, or a $C_{5-20}$aryl group, preferably a $C_{1-7}$alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$alkyl group, a $C_{3-20}$heterocyclyl group, or a $C_{5-20}$aryl group, preferably a $C_{1-7}$alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarbonyloxy: —OC(=O)OR, wherein R is an ester substituent, for example, a $C_{1-7}$alkyl group, a $C_{3-20}$heterocyclyl group, or a $C_{5-20}$aryl group, preferably a $C_{1-7}$alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —NR$^1$C(=O)R$^2$, wherein R$^1$ is an amide substituent, for example, a $C_{1-7}$alkyl group, a $C_{3-20}$heterocyclyl group, or a $C_{5-20}$aryl group, preferably a $C_{1-7}$alkyl group, and R$^2$ is an acyl substituent, for example, a $C_{1-7}$alkyl group, a $C_{3-20}$heterocyclyl group, or a $C_{5-20}$aryl group, preferably a $C_{1-7}$alkyl group. Examples of acylamido groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

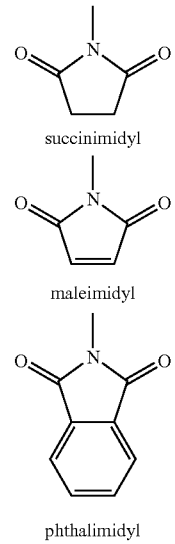

succinimidyl maleimidyl phthalimidyl

Tetrazolyl: a five membered aromatic ring having four nitrogen atoms and one carbon atom,

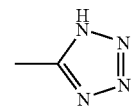

Amino: —NR$^1$R$^2$, wherein R$^1$ and R$^2$ are independently amino substituents, for example, hydrogen, a $C_{1-7}$alkyl group (also referred to as $C_{1-7}$alkylamino or di-$C_{1-7}$alkylamino), a $C_{3-20}$heterocyclyl group, or a $C_{5-20}$aryl group, preferably H or a $C_{1-7}$alkyl group, or, in the case of a "cyclic" amino group, R$^1$ and R$^2$, taken together with the nitrogen atom to which they are attached, form a heterocyclic ring having from 4 to 8 ring atoms. Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Nitro: —NO$_2$.

Cyano (nitrile, carbonitrile): —CN.

Azido: —N$_3$.

Sulfhydryl (thiol, mercapto): —SH.

Thioether (sulfide): —SR, wherein R is a thioether substituent, for example, a $C_{1-7}$alkyl group (also referred to as a $C_{1-7}$alkylthio group), a $C_{3-20}$heterocyclyl group, or a $C_{5-20}$aryl group, preferably a $C_{1-7}$alkyl group. Examples of $C_{1-7}$alkylthio groups include, but are not limited to, —SCH$_3$ and —SCH$_2$CH$_3$.

Sulfonamido: —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

As mentioned above, a $C_{1-7}$alkyl group may be substituted with, for example, hydroxy (also referred to as a $C_{1-7}$hydroxyalkyl group), $C_{1-7}$alkoxy (also referred to as a $C_{1-7}$alkoxyalkyl group), amino (also referred to as a $C_{1-7}$aminoalkyl group), halo (also referred to as a $C_{1-7}$haloalkyl group), carboxy (also referred to as a $C_{1-7}$carboxyalkyl group), and $C_{5-20}$aryl (also referred to as a $C_{5-20}$aryl-$C_{1-7}$alkyl group).

Similarly, a $C_{5-20}$aryl group may be substituted with, for example, hydroxy (also referred to as a $C_{5-20}$hydroxyaryl group), halo (also referred to as a $C_{5-20}$haloaryl group), amino (also referred to as a $C_{5-20}$aminoaryl group, e.g., as in aniline), $C_{1-7}$alkyl (also referred to as a $C_{1-7}$alkyl-$C_{5-20}$aryl group, e.g., as in toluene), and $C_{1-7}$alkoxy (also referred to as a $C_{1-7}$alkoxy-$C_{5-20}$aryl group, e.g., as in anisole).

These and other specific examples of such substituted groups are also discussed below.

$C_{1-7}$haloalkyl group: The term "$C_{1-7}$haloalkyl group," as used herein, pertains to a $C_{1-7}$alkyl group in which at least one hydrogen atom (e.g., 1, 2, 3) has been replaced with a halogen atom (e.g., F, Cl, Br, I). If more than one hydrogen atom has been replaced with a halogen atom, the halogen atoms may independently be the same or different. Every hydrogen atom may be replaced with a halogen atom, in which case the group may conveniently be referred to as a $C_{1-7}$perhaloalkyl group." Examples of $C_{1-7}$haloalkyl groups include, but are not limited to, —$CF_3$, —$CHF_2$, —$CH_2F$, —$CCl_3$, —$CBr_3$, —$CH_2CH_2F$, —$CH_2CHF_2$, —$CH_2CF_3$.

$C_{1-7}$hydroxyalkyl: The term "$C_{1-7}$hydroxyalkyl group," as used herein, pertains to a $C_{1-7}$alkyl group in which at least one hydrogen atom has been replaced with a hydroxy group. Examples of $C_{1-7}$hydroxyalkyl groups include, but are not limited to, —$CH_2OH$, —$CH_2CH_2OH$, and —$CH(OH)CH_2OH$.

$C_{1-7}$carboxyalkyl: The term "$C_{1-7}$carboxyalkyl group," as used herein, pertains to a $C_{1-7}$alkyl group in which at least one hydrogen atom has been replaced with a carboxy group. Examples of $C_{1-7}$carboxyalkyl groups include, but are not limited to, —$CH_2COOH$ and —$CH_2CH_2COOH$.

$C_{1-7}$acyloxyalkyl: The term "$C_{1-7}$acyloxyalkyl group," as used herein, pertains to a $C_{1-7}$alkyl group in which at least one hydrogen atom has been replaced with an acyloxy group. Examples of $C_{1-7}$acyloxyalkyl groups include, but are not limited to, —$CH_2OC(=O)R$, —$CH_2CH_2OC(=O)R$, and —$CH=CHOC(=O)R$.

$C_{1-7}$oxycarbonylalkyl: The term "$C_{1-7}$oxycarbonylalkyl group," as used herein, pertains to a $C_{1-7}$alkyl group in which at least one hydrogen atom has been replaced with an oxycarboxy group. Examples of $C_{1-7}$oxycarbonylalkyl groups include, but are not limited to, —$CH_2C(=O)OR$, —$CH_2CH_2C(=O)OR$, and —$CH=CHC(=O)OR$.

$C_{1-7}$oxycarbonyloxyalkyl: The term "$C_{1-7}$oxycarbonyloxyalkyl group," as used herein, pertains to a $C_{1-7}$alkyl group in which at least one hydrogen atom has been replaced with an oxycarboxyoxy group. Examples of $C_{1-7}$oxycarbonyloxyalkyl groups include, but are not limited to, —$CH_2OC(=O)OR$, —$CH_2CH_2OC(=O)OR$, and —$CH=CHOC(=O)OR$.

$C_{1-7}$aminoalkyl: The term "$C_{1-7}$aminoalkyl group," as used herein, pertains to a $C_{1-7}$alkyl group in which at least one hydrogen atom has been replaced with an amino group. Examples of $C_{1-7}$aminoalkyl groups include, but are not limited to, —$CH_2NH_2$, —$CH_2CH_2NH_2$, and —$CH_2CH_2N(CH_3)_2$.

$C_{1-7}$aminoalkylamino: The term "$C_{1-7}$aminoalkylamino," as used herein, pertains to an amino group, —$NR^1R^2$, in which one of the substituents, $R^1$ or $R^2$, is itself a $C_{1-7}$aminoalkyl group (—$C_{1-7}$alkyl-$NR^1R^2$). The $C_{1-7}$aminoalkylamino may be represented, for example, by the formula —$NR^1$—$C_{1-7}$alkyl-$NR^1R^2$. Examples of amino-$C_{1-7}$alkylamino groups include, but are not limited to, groups of the formula —$NR^1(CH_2)_nNR^1R^2$, where n is 1 to 6, for example, —$NHCH_2NH_2$, —$NH(CH_2)_2NH_2$, —$NH(CH_2)_3NH_2$, —$NH(CH_2)_4NH_2$, —$NH(CH_2)_5NH_2$, —$NH(CH_2)_6NH_2$, —$NHCH_2NH(Me)$, —$NH(CH_2)_2NH(Me)$, —$NH(CH_2)_3NH(Me)$, —$NH(CH_2)_4NH(Me)$, —$NH(CH_2)_5NH(Me)$, —$NH(CH_2)_6NH(Me)$, —$NHCH_2NH(Et)$, —$NH(CH_2)_2NH(Et)$, —$NH(CH_2)_3NH(Et)$, —$NH(CH_2)_4NH(Et)$, —$NH(CH_2)_5NH(Et)$, and —$NH(CH_2)_6NH(Et)$.

$C_{1-7}$amidoalkyl: The term "$C_{1-7}$amidoalkyl group," as used herein, pertains to a $C_{1-7}$alkyl group in which at least one hydrogen atom has been replaced with an amido group. Examples of $C_{1-7}$amidoalkyl groups include, but are not limited to, —$CH_2C(=O)NH_2$, —$CH_2CH_2C(=O)NH_2$, and —$CH=CHC(=O)NH_2$.

$C_{1-7}$acylamidoalkyl: The term "$C_{1-7}$acylamidoalkyl group," as used herein, pertains to a $C_{1-7}$alkyl group in which at least one hydrogen atom has been replaced with an acylamido group. Examples of $C_{1-7}$acylamidoalkyl groups include, but are not limited to, —$CH_2NHC(=O)R$, —$CH_2CH_2NHC(=O)R$, and —$CH=CHNHC(=O)R$.

$C_{1-7}$cyanoalkyl: The term "$C_{1-7}$cyanoalkyl group," as used herein, pertains to a $C_{1-7}$alkyl group in which at least one hydrogen atom has been replaced with a cyano group. Examples of $C_{1-7}$cyanoalkyl groups include, but are not limited to, —$CH_2CN$, —$CH_2CH_2CN$, and —$CH=CHCN$.

$C_{1-7}$alkyl-$C_{5-20}$aryl: The term "$C_{1-7}$alkyl-$C_{5-20}$aryl," as used herein, describes certain $C_{5-20}$aryl groups which have been substituted with a $C_{1-7}$alkyl group. Examples of such groups include, but are not limited to, tolyl (as in toluene), xylyl (as in xylene), mesityl (as in mesitylene), styryl (as in styrene), and cumenyl (as in cumene).

$C_{5-20}$aryl-$C_{1-7}$alkyl: The term "$C_{5-20}$aryl-$C_{1-7}$alkyl," as used herein, describers certain $C_{1-7}$alkyl groups which have been substituted with a $C_{5-20}$aryl group. Examples of such groups include, but are not limited to, benzyl (phenylmethyl), tolylmethyl, phenylethyl, and triphenylmethyl (trityl).

$C_{5-20}$haloaryl: The term "$C_{5-20}$haloaryl," as used herein, describes certain $C_{5-20}$aryl groups which have been substituted with one or more halo groups. Examples of such groups include, but are not limited to, halophenyl (e.g., fluorophenyl, chlorophenyl, bromophenyl, or iodophenyl, whether ortho-, meta-, or parasubstututed), dihalophenyl, trihalophenyl, tetrahalophenyl, and pentahalophenyl.

Includes Other Forms

Included in the above are the well known ionic, salt, solvate, and protected forms of these substituents. For example, a reference to carboxylic acid (—COOH) also includes the anionic (carboxylate) form (—$COO^-$), a salt or solvate thereof, as well as conventional protected forms. Similarly, a reference to an amino group includes the protonated form (—$N^+HR^1R^2$), a salt or solvate of the amino group, for example, a hydrochloride salt, as well as conventional protected forms of an amino group. Similarly, a reference to a hydroxyl group also includes the anionic form (—$O^-$), a salt or solvate thereof, as well as conventional protected forms of a hydroxyl group.

Isomers, Salts, Solvates, Protected Forms, and Prodrugs

A certain compound may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

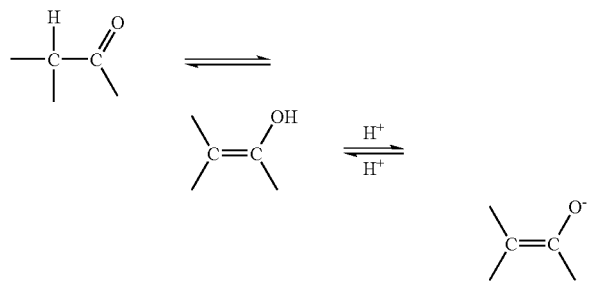

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein in a known manner.

Unless otherwise specified, a reference to a particular compound also includes ionic, salt, solvate (e.g., hydrate), protected forms, and prodrugs thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1–19.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as Na+ and K+, alkaline earth cations such as $Ca^{2+}$ and $Mg^{2+}$, and other cations such as $Al^{+3}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: acetic, propionic, succinic, gycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, toluenesulfonic, methanesulfonic, ethanesulfonic, ethane disulfonic, oxalic, isethionic, valeric, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form," as used herein, pertains to a compound in which one or more reactive functional groups are protected from undesirable chemical reactions, that is, are in the form of a protected or protecting group (also known as a masked or masking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts, Wiley, 1991), and *Protective Groups in Organic Synthesis* (T. Green and P. Wuts; 3rd Edition; John Wiley and Sons, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)$CH_3$, —OAc).

For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH-Psec); or, in suitable cases (e.g., cyclic amines), as a nitroxide radical (>N—O.).

For example, a carboxylic acid group may be protected as an ester for example, as: an C$_{1-7}$alkyl ester (e.g., a methyl ester; a t-butyl ester); a C$_{1-7}$haloalkyl ester (e.g., a C$_{1-7}$trihaloalkyl ester); a triC$_{1-7}$alkylsilyl-C$_{1-7}$alkyl ester; or a C$_{5-20}$aryl-C$_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

It may be convenient or desirable to prepare, purify, and/or handle the active compound in the form of a prodrug. The term "prodrug," as used herein, pertains to a compound which, when metabolised, yields the desired active compound. Typically, the prodrug is inactive, or less active than the active compound, but may provide advantageous handling, administration, or metabolic properties. For example, some prodrugs are esters of the active compound; during metabolysis, the ester group is cleaved to yield the active drug.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those wherein R is C$_{1-7}$alkyl (e.g., -Me, -Et); C$_{1-7}$aminoalkyl (e.g., aminoethyl; 2-(N,N-diethylamino)ethyl; 2-(4-morpholino)ethyl); and acyloxy-C$_{1-7}$alkyl (e.g., acyloxymethyl; acyloxyethyl; e.g., pivaloyloxymethyl; acetoxymethyl; 1-acetoxyethyl; 1-(1-methoxy-1-methyl)ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy)carbonyloxyethyl; (4-tetrahydropyranyl)carbonyloxymethyl; and 1-(4-tetrahydropyranyl)carbonyloxyethyl).

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Acronyms

For convenience, many chemical moieties are represented using well known abbreviations, including but not limited to, methyl (Me), ethyl (Et), n-propyl (nPr), iso-propyl (iPr), n-butyl (nBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether (Et$_2$O), acetic acid (AcOH), dichloromethane (methylene chloride, DCM), trifluoroacetic acid (TFA), dimethylformamide (DMF), tetrahydrofuran (THF), and dimethylsulfoxide (DMSO).

Synthesis

The quino[4,3,2-kl]acridinium salts of the present invention may be prepared, for example, by the methods described herein, or by adapting these or other well known methods in well known ways.

Many quino[4,3,2-kl]acridinium salts may be prepared via the corresponding quinolinium salt. In this approach, a haloaniline is reacted with crotonaldehyde to give the corresponding quinoline salt, for example, by reaction in the presence of acid and an oxidant (see, for example, Song et al., 1993):

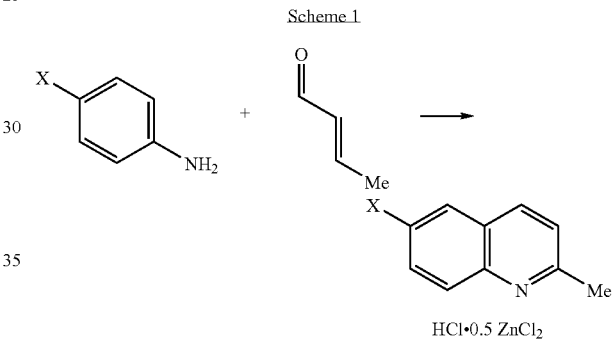

Scheme 1

The quinoline salt is then neutralised, for example, with potassium carbonate, to give the corresponding quinoline:

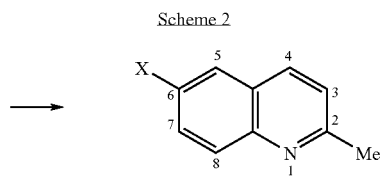

Scheme 2

The quinoline is then N-alkylated, for example, by reaction with an alkyl sulfate (e.g., dimethylsulfate), to give the corresponding N-alkylated quinolinium salt:

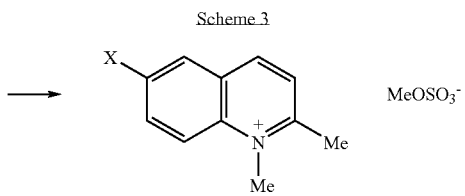

Scheme 3

Other N-alkylated quinolinium salts may be prepared from the corresponding quinolines (e.g., 2-methylquinoline, 2,6-dimethylquinoline), for example, by reaction with an alkyl sulfate (e.g., dimethylsulfate), to give the corresponding N-alkylated quinolinium salt:

Scheme 4

Scheme 5

The N-alkylated quinolinium salt is then converted to the corresponding $N^8,N^{13}$-dialkylated quino[4,3,2-kl]acridinium salt, for example, by reaction with a strongly basic secondary amine, such as piperidine or pyrrolidine (see, for example, Oszczapowicz et al., 1988), where X is hydrogen, halo (e.g., —F, —Cl), or methyl:

Scheme 6

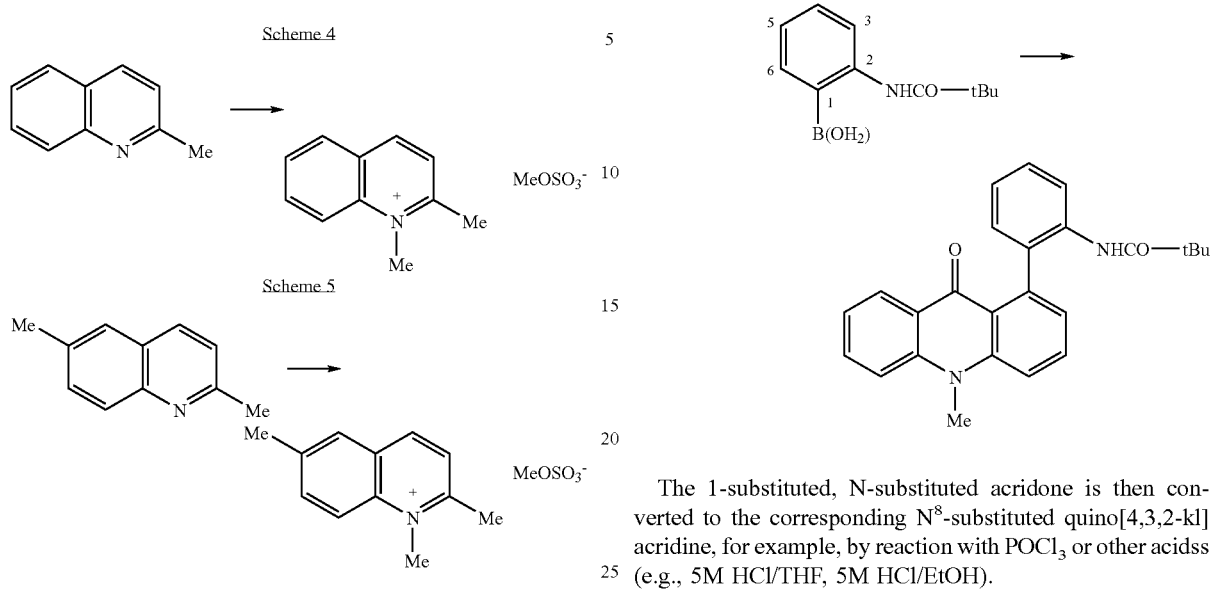

Suzuki cross-coupling may also be used to prepare many quino[4,3,2-kl]acridinium salts. In this approach, an acylaminobenzene boronic acid is coupled to an N-substituted acridone having a leaving group at the 1-position, for example, by reaction with triphenylphosphine palladium(0), to give the corresponding 1-substituted, N-substituted acridone:

Scheme 7

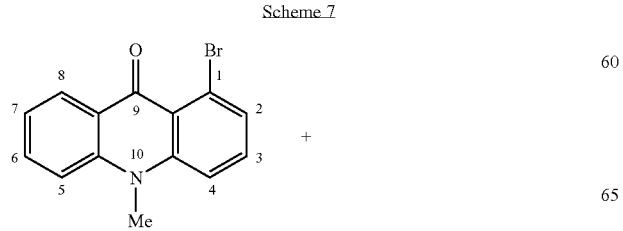

-continued

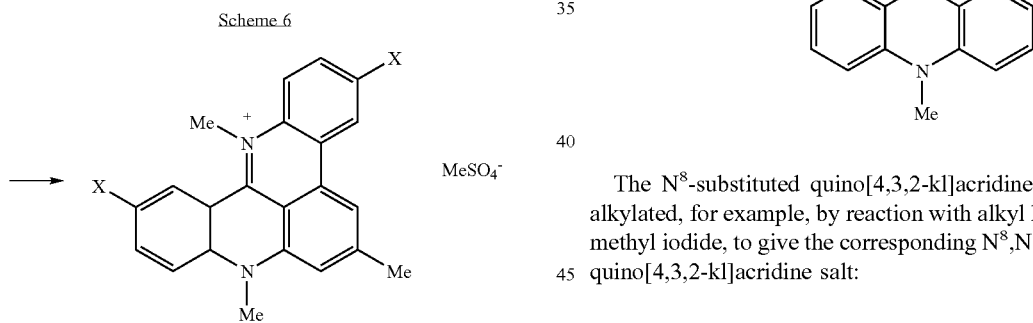

The 1-substituted, N-substituted acridone is then converted to the corresponding $N^8$-substituted quino[4,3,2-kl]acridine, for example, by reaction with $POCl_3$ or other acidss (e.g., 5M HCl/THF, 5M HCl/EtOH).

Scheme 8

The $N^8$-substituted quino[4,3,2-kl]acridine is then $N^{13}$-alkylated, for example, by reaction with alkyl halide such as methyl iodide, to give the corresponding $N^8,N^{13}$-dialkylated quino[4,3,2-kl]acridine salt:

Scheme 9

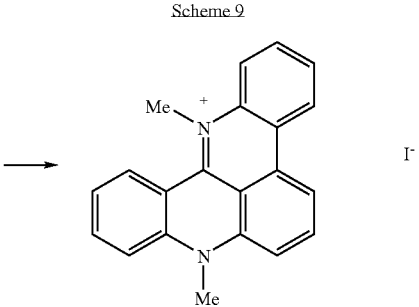

By employing combinations of substituted boronic acids and substituted acridones, a variety of different $N^8,N^{13}$-dialkylated quino[4,3,2-kl]acridine salts may be prepared.

Suitable acylaminobenzene boronic acids may also be prepared. See, for example, Gullier et al., 1995; Timari et al., 1996. In one approach, pivaloyl protected anilines (i.e., PhNH—COC(CH$_3$)$_3$) are prepared by reacting (optionally substituted) aniline with trimethylacetyl chloride and potassium carbonate:

Scheme 10

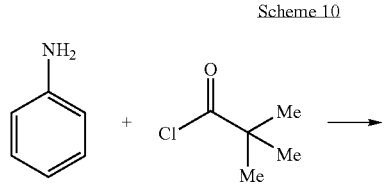

The pivaloyl protected aniline is then reacted with alkyl lithium (e.g., n-BuLi) to form the corresponding 2-lithium intermediate which is then reacted first with trimethylborate, and then with water, to give the corresponding 2-pivaloylaminobenzene boronic acid:

Scheme 11

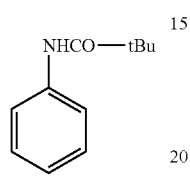

Substituted anilines give corresponding pivaloyl protected anilines. Examples of such substituted anilines include 2-halo, 3-halo, and 4-halo, which predominantly give rise to 3-halo, 6-halo, and 5-halo variants of 2-pivaloylamino-benzene boronic acid.

Scheme 12

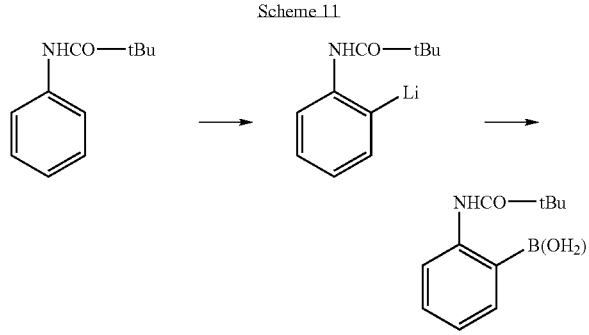

Scheme 13

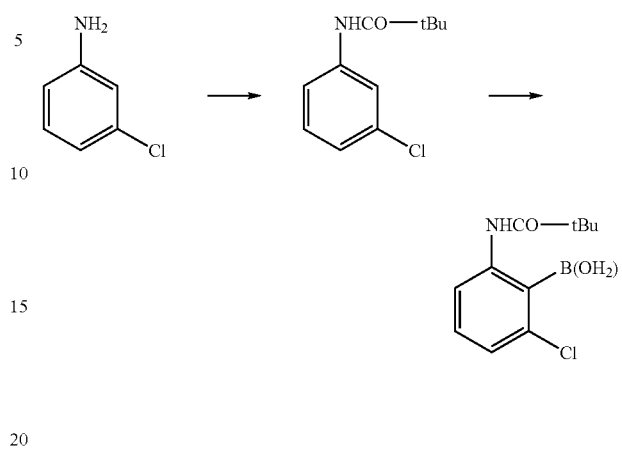

Scheme 14

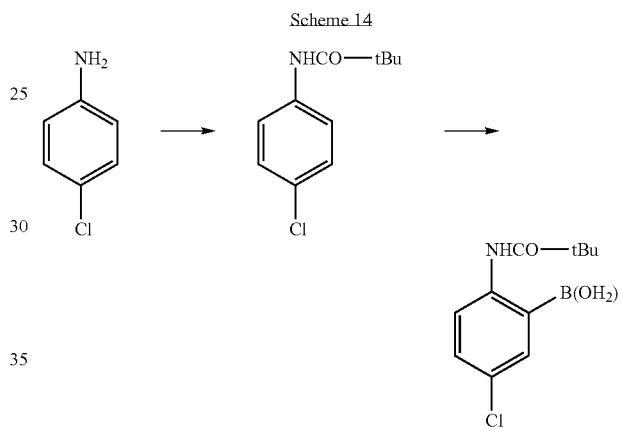

Suitable acridones having a leaving group at the 1-position may be prepared. For example, in one approach, a suitably substituted benzoic acid (e.g., 2-chlorobenzoic acid) is reacted with a suitably substituted aniline (e.g., 3-bromoaniline), for example, in the presence of potassium carbonate and catalytic copper, to give the secondary amine (see, for example, Prager et al., 1972):

Scheme 15

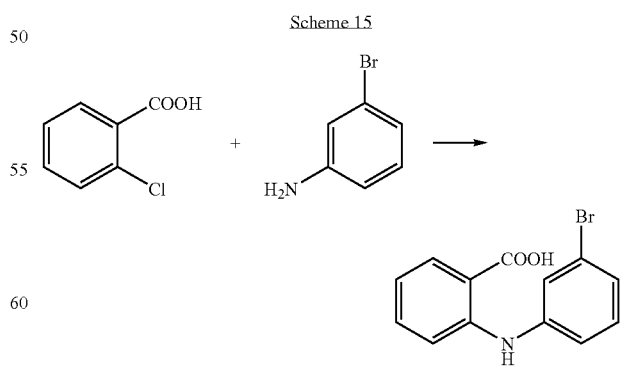

The secondary amine is then converted to the corresponding acridone, for example, by reaction with concentrated acid (e.g., H$_2$SO$_4$):

Scheme 16

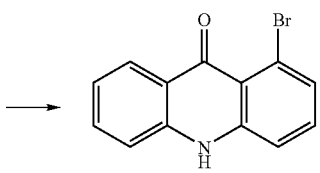

The acridone is then N-alkylated, for example, by reaction with alkyl sulfate (e.g., dimethylsulfate), to give the corresponding N-alkylated,1-substituted acridone:

Scheme 17

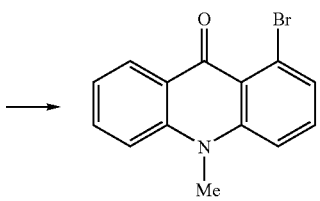

By employing different substituted benzoic acids, a variety of N-alkylated, 1-substituted acridones may be prepared. For example, by using 2,4-dichlorobenzoic acid, the corresponding 1-bromo-6-chloro product is obtained:

Scheme 18

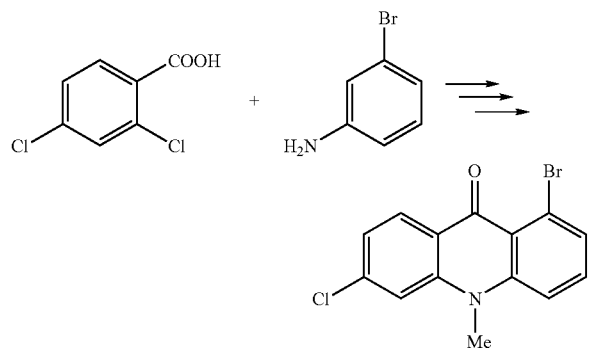

In another approach, suitable acridones having a leaving group at the 1-position may be prepared by reaction of a suitably substituted anthranilate and a suitably substituted phlorglucinol, for example, in the presence of catalytic para-toluenesulfonic acid, to give the corresponding substituted 1-hydroxy acridone (see, for example, Reisch et al., 1991):

Scheme 19

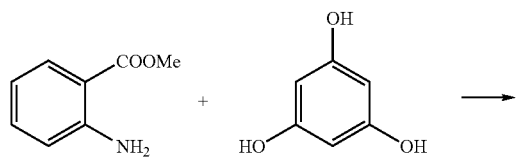

-continued

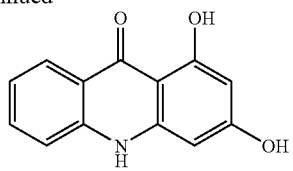

The substituted 1-hydroxy acridone is then N-alkylated, for example, with alkyl halide (e.g., methyl iodide), to give the corresponding substituted N-alkylated, 1-hydroxy acridone:

Scheme 20

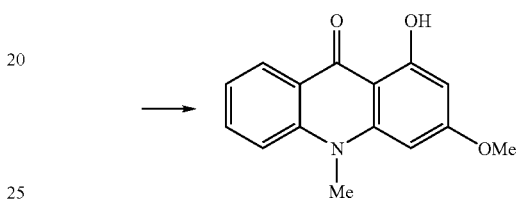

The substituted N-alkylated,1-hydroxy acridone is then converted to the corresponding substituted N-alkylated acridone with a leaving group at the 1-position, for example, by reaction with triflic anhydride:

Scheme 21

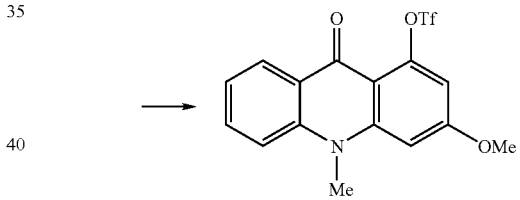

By employing different substituted acridones with different substituted boronic acids, a variety of substituted quino[4,3,2-kl]acridinium salts may be prepared, for example, according to the general reaction:

Scheme 22

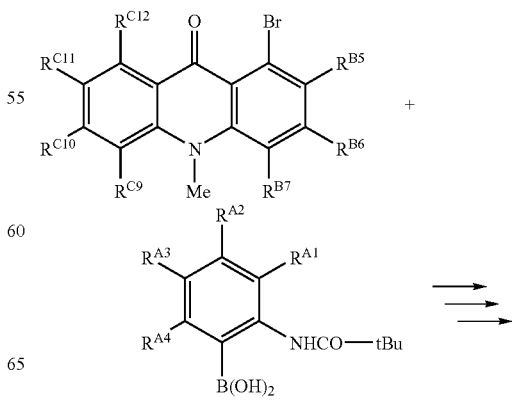

-continued

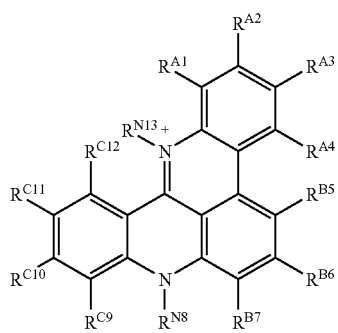

Alkylation of quino[4,3,2-kl]acridines may also be used to prepare many quino[4,3,2-kl]acridinium salts. In this approach, the quino[4,3,2-kl]acridine is first reacted with an alkylsulfate (e.g., dimethylsulfate) to give the corresponding $N^8$-alkylated quino[4,3,2-kl]acridine:

Scheme 23

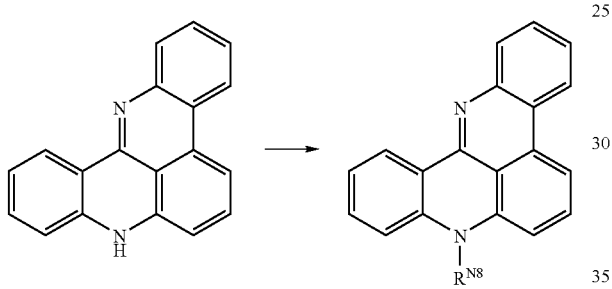

The $N^8$-alkylated quino[4,3,2-kl]acridine is then reacted with an alkyl halide (e.g., methyl iodide) to give the corresponding substituted $N^8,N^{13}$-dialkylated quino[4,3,2-kl]acridinium salt:

Scheme 24

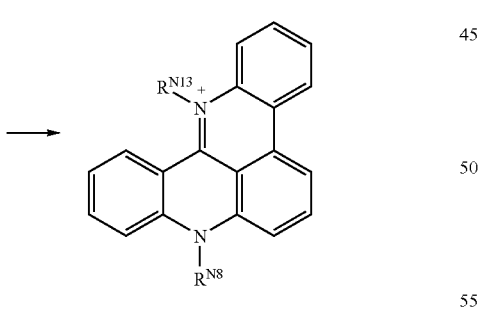

If appropriate, $N^8$-alkylated quino[4,3,2-kl]acridine may be derivatised before the final alkylation step. For example, halo groups, for example, at the 2-, 3-, 6-, 10-, or 11-position, may be replaced with, for example, alkyl or aryl groups.

For example, a 3-chloro-$N^8$-alkylated quino[4,3,2-kl]acridine may be reacted with methyl acrylate (i.e., $CH_2$=CHCOOCH$_3$) to form the 3-($CH_2$=CHCOOCH$_3$) product and then hydrogenated to form the 3-($CH_2CH_2COOCH_3$) product (see, for example, Littke et al., 1999):

Scheme 25

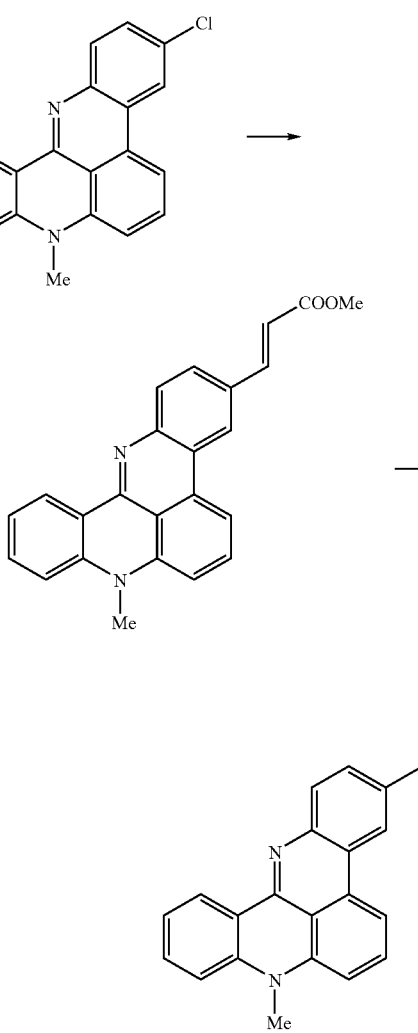

This product may then be $N^{13}$-alkylated, as above, to give the corresponding substituted $N^8,N^{13}$-dialkylated quino[4,3,2-kl]acridinium salt:

Scheme 26

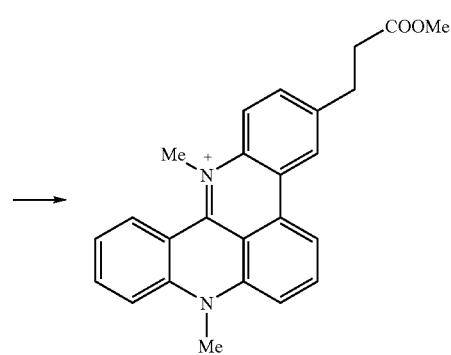

Similar products may be obtained by reaction with, for example, substituted acrylamides, e.g., acryloylmorpholine:

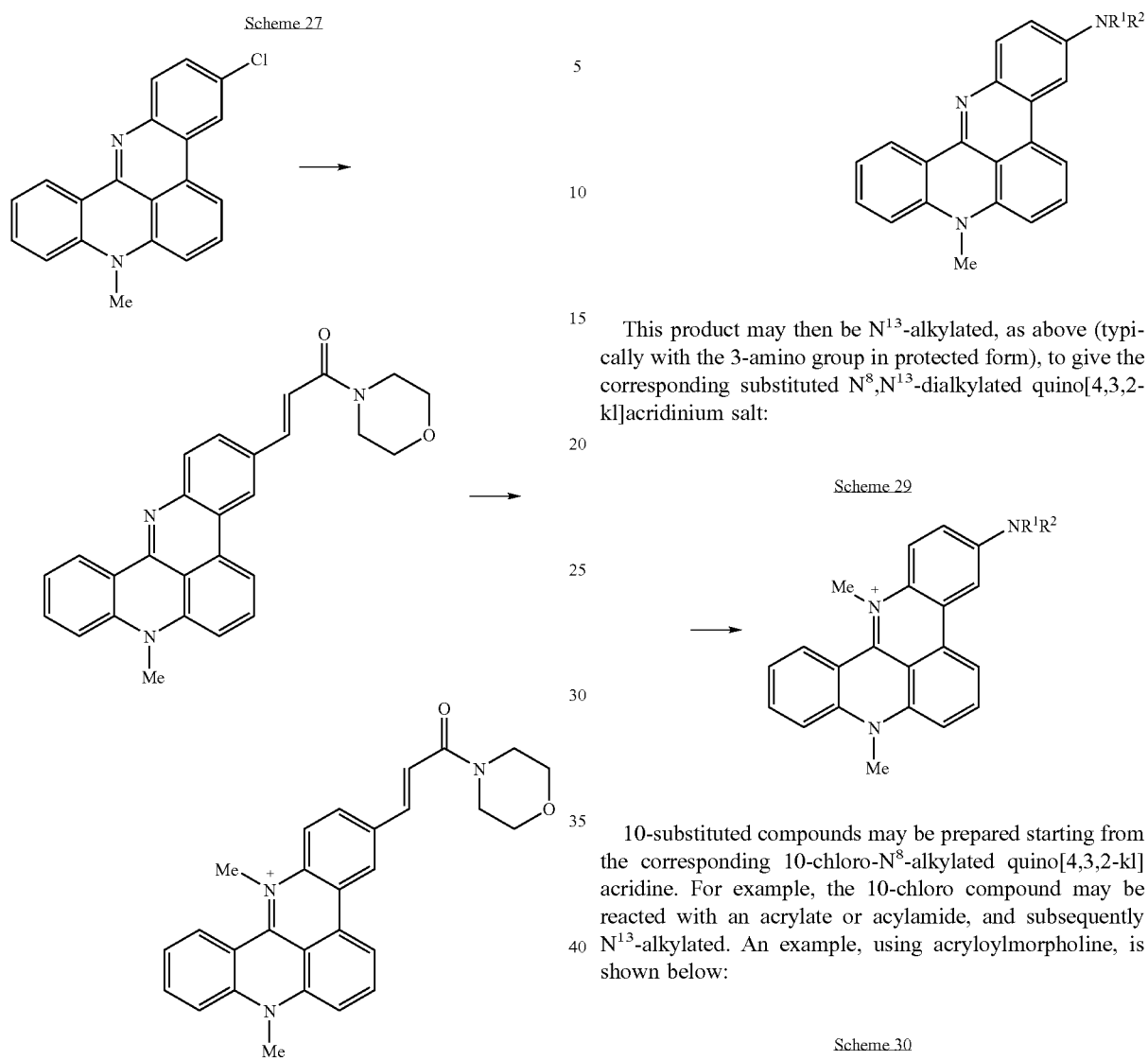

Similarly, a 3-chloro-N⁸-alkylated quino[4,3,2-kl]acridine may be reacted with an amine (i.e., HNR¹R²) to form the 3-amino (3-NR¹R²) product (see, for example, Wolfe et al., 2000):

This product may then be $N^{13}$-alkylated, as above (typically with the 3-amino group in protected form), to give the corresponding substituted $N^8,N^{13}$-dialkylated quino[4,3,2-kl]acridinium salt:

10-substituted compounds may be prepared starting from the corresponding 10-chloro-$N^8$-alkylated quino[4,3,2-kl]acridine. For example, the 10-chloro compound may be reacted with an acrylate or acylamide, and subsequently $N^{13}$-alkylated. An example, using acryloylmorpholine, is shown below:

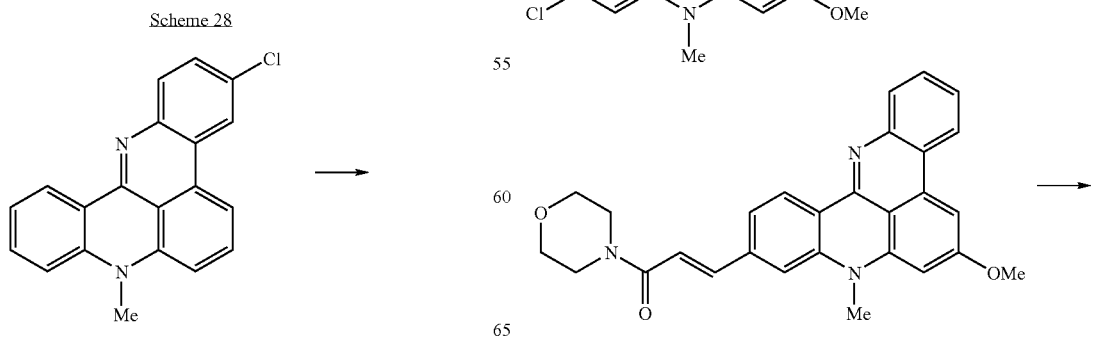

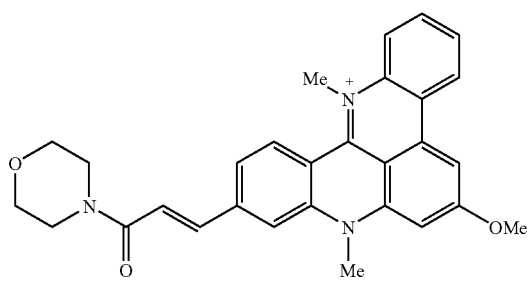

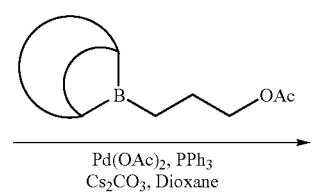

Scheme 32

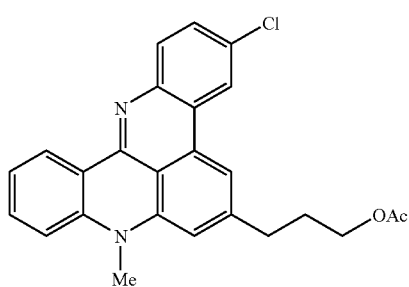

6-substituted compounds may be prepared starting from the corresponding 6-activated-$N^8$-alkylated quino[4,3,2-kl] acridine. For example, a suitable 6-triflate-$N^8$-alkylated quino[4,3,2-kl]acridine may be prepared from the 6-hydroxy compound, e.g., by reaction with triflic anhydride and a suitable base; the 6-hydroxy compound may be prepared from the 6-methoxy compound, e.g., by reaction with $AlCl_3$. An example is shown below.

Scheme 31

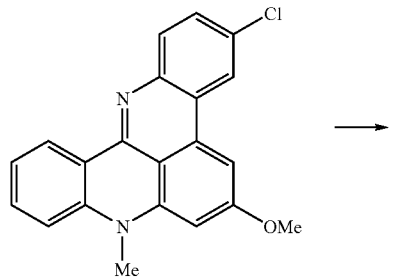

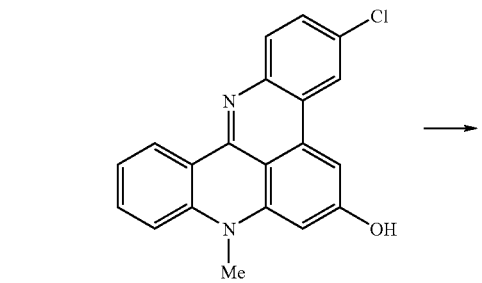

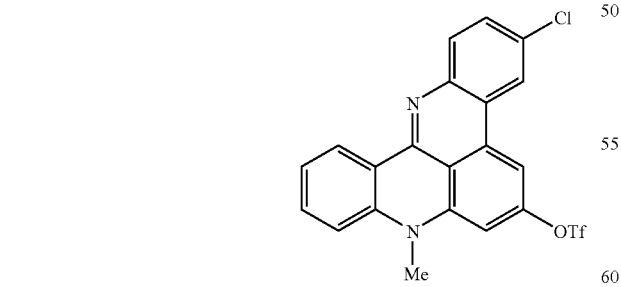

Many 6-subsituted-$N^8$-alkylated quino[4,3,2-kl]acridine may then be prepared from the 6-triflate comopund, for example, using a Suzuki, Heck, or Sonogashira reaction. Some examples of these methods are shown below. The products may be subsequently $N^{13}$-alkylated.

Scheme 33

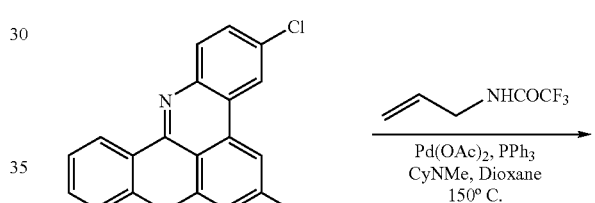

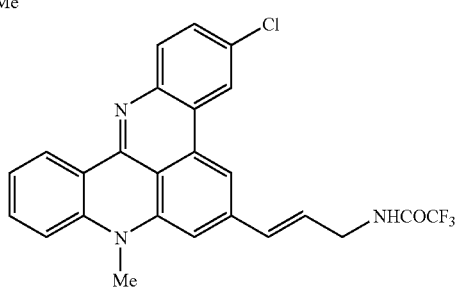

Scheme 34

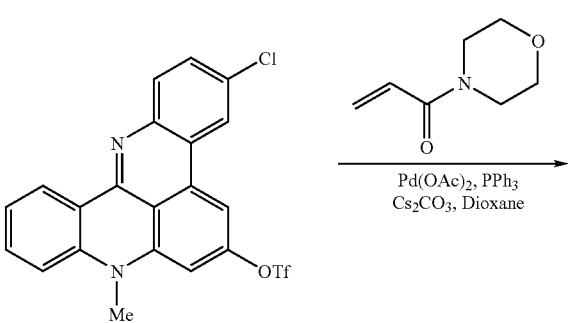

-continued

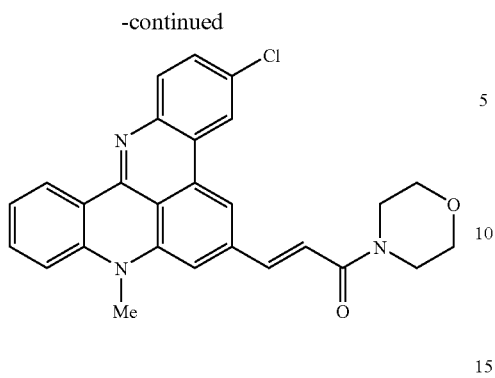

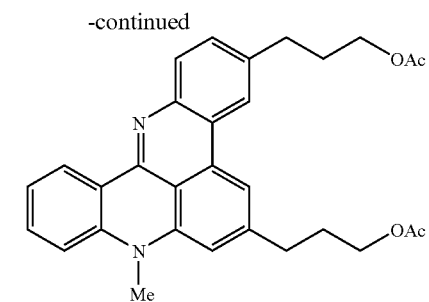

Scheme 35

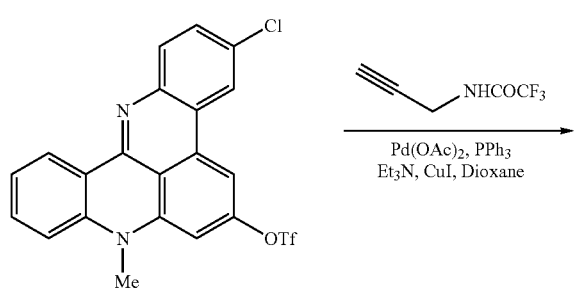

Scheme 37

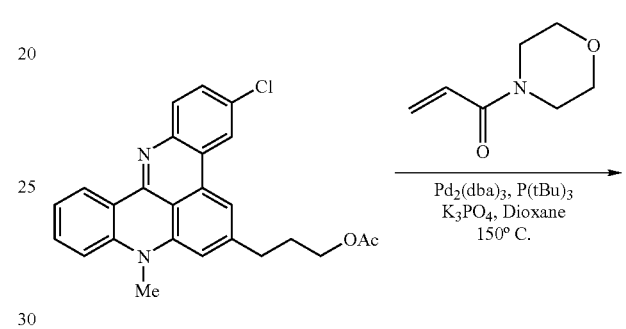

Many 3,6-disubsituted-$N^8$-alkylated quino[4,3,2-kl]acridine may be prepared from the corresponding 3-chloro-6-substituted compound using a more reactive catalyst system, e.g., $Pd_2(dba)_3/P(tBu)_3$. ($Pd_2(dba)_3$ is tris(dibenzylideneacetone) dipalladium (0)). Some examples of these methods are shown below. The products may be subsequently $N^{13}$-alkylated.

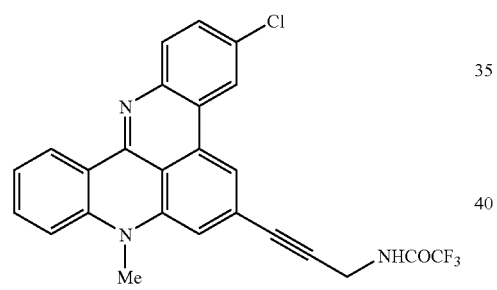

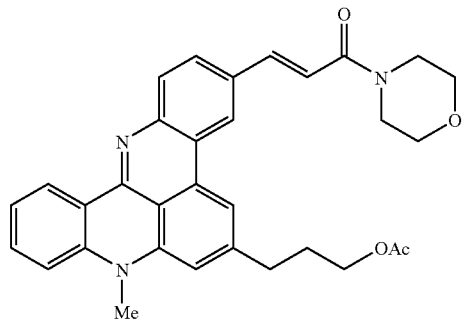

Scheme 36

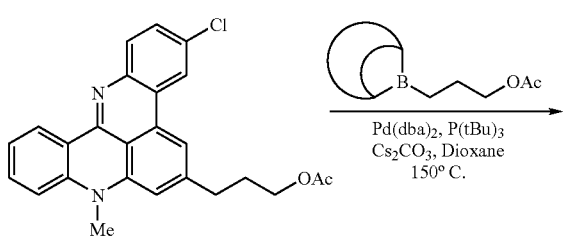

Uses

The present invention provides active compounds, specifically, active quino[4,3,2-kl]acridinium salts, as described herein, which are capable of inhibiting telomerase (for example, inhibiting telomerase activity, inhibiting formation of telomerase complexes, inhibiting activity of telomerase complexes, etc.).

The term "active," as used herein, pertains to compounds which are capable of inhibiting telomerase and/or of regulating cell proliferation, and specifically includes both compounds with intrinsic activity (drugs) as well as prodrugs of such compounds, which prodrugs may themselves exhibit little or no intrinsic activity.

One of ordinary skill in the art is readily able to determine whether or not a candidate compound inhibits telomerase activity. For example, one assay which may conveniently be used in order to assess the telomerase inhibition offered by a particular compound is described in the examples below.

The present invention also provides methods of inhibiting telomerase in a cell, comprising contacting said cell with an effective amount of an active compound, preferably in the form of a pharmaceutically acceptable composition. Such a method may be practised in vitro or in vivo.

The present invention also provides active compounds which regulate cell proliferation, as well as methods of regulating cell proliferation, comprising contacting a cell with an effective amount of an active compound, preferably in the form of a pharmaceutically acceptable composition. Such a method may be practised in vitro or in vivo.

One of ordinary skill in the art is readily able to determine whether or not a candidate compound regulates cell proliferation for any particular cell line. For example, one assay which may conveniently be used to assess the activity offered by a particular compound is described in the examples below.

For example, a sample of cells (e.g., from a tumour) may be grown in vitro and a candidate compound brought into contact with the cells, and the effect of the compound on those cells observed. As examples of "effect," the morphological status of the cells may be determined (e.g., alive or dead), or the expression levels of genes associated with cell cycle regulation determined. Where the candidate compound is found to exert an influence on the cells, this may be used as a prognostic or diagnostic marker of the efficacy of the compound in methods of treating a patient carrying cells of the same type (e.g., the tumour or a tumour of the same cellular type).

The present invention further provides active compounds which are antiproliferative agents. The term "antiproliferative agent" as used herein, pertain to a compound which treats a proliferative condition (i.e., a compound which is useful in the treatment of a proliferative condition).

One of ordinary skill in the art is readily able to determine whether or not a candidate compound treats a proliferative condition for any particular cell line. For example, one assay which may conveniently be used to assess the activity offered by a particular compound is described in the examples below.

The terms "cell proliferation," "proliferative condition," "proliferative disorder," and "proliferative disease," are used interchangeably herein and pertain to an unwanted or uncontrolled cellular proliferation of excessive or abnormal cells which is undesired, such as, neoplastic or hyperplastic growth, whether in vitro or in vivo. Examples of proliferative conditions include, but are not limited to, pre-malignant and malignant cellular proliferation, including but not limited to, malignant neoplasms and tumours, cancers, leukemias, psoriasis, bone diseases, fibroproliferative disorders (e.g., of connective tissues), and atherosclerosis. Any type of cell may be treated, including but not limited to, lung, colon, breast, ovarian, prostate, liver, pancreas, brain, and skin.

Antiproliferative compounds of the present invention have application in the treatment of cancer, and so the present invention further provides anticancer agents. The term "anticancer agent" as used herein, pertains to a compound which treats a cancer (i.e., a compound which is useful in the treatment of a cancer). The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

The invention further provides a method of treatment of the human or animal body, the method comprising administering to a subject in need of treatment a therapeutically-effective amount of an active compound, preferably in the form of a pharmaceutical composition.

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e., prophylaxis) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio.

The term "treatment" includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy.

The invention further provides active compounds for use in a method of treatment of the human or animal body, for example, in the treatment of a proliferative condition, for example cancer.

The invention further provides the use of an active compound for the manufacture of a medicament, for example, for the treatment of a proliferative condition, as discussed above.

Active compounds may also be used as cell culture additives to inhibit telomerase, for example, in order to regulate cell proliferation in vitro.

Active compounds may also be used, as described above, in combination therapies, that is, in conjunction with other agents, for example, cytotoxic agents.

Active compounds may also be used as part of an in vitro assay, for example, in order to determine whether a candidate host is likely to benefit from treatment with the compound in question.

Active compounds may also be used as a standard, for example, in an assay, in order to identify other active compounds, other telomerase inhibitors, other antiproliferative agents, etc.

Routes of Administration

The active compound or pharmaceutical composition comprising the active compound may be administered to a subject by any convenient route of administration, whether systemically/peripherally or topically (i.e., at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject

The subject may be a prokaryote (e.g., bacteria) or a eukaryote (e.g., protoctista, fungi, plants, animals).

The subject may be a protoctista, an alga, or a protozoan.

The subject may be a plant, an angiosperm, a dicotyledon, a monocotyledon, a gymnosperm, a conifer, a ginkgo, a cycad, a fern, a horsetail, a clubmoss, a liverwort, or a moss.

The subject may be an animal.

The subject may be a chordate, an invertebrate, an echinoderm (e.g., starfish, sea urchins, brittlestars), an arthropod, an annelid (segmented worms) (e.g., earthworms, lugworms, leeches), a mollusk (cephalopods (e.g., squids, octopi), pelecypods (e.g., oysters, mussels, clams), gastropods (e.g., snails, slugs)), a nematode (round worms), a platyhelminthes (flatworms) (e.g., planarians, flukes, tapeworms), a cnidaria (e.g., jelly fish, sea anemones, corals), or a porifera (e.g., sponges).

The subject may be an arthropod, an insect (e.g., beetles, butterflies, moths), a chilopoda (centipedes), a diplopoda (millipedes), a crustacean (e.g., shrimps, crabs, lobsters), or an arachnid (e.g., spiders, scorpions, mites).

The subject may be a chordate, a vertebrate, a mammal, a bird, a reptile (e.g., snakes, lizards, crocodiles), an amphibian (e.g., frogs, toads), a bony fish (e.g., salmon, plaice, eel, lungfish), a cartilaginous fish (e.g., sharks, rays), or a jawless fish (e.g., lampreys, hagfish).

The subject may be a mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject may be any of its forms of development, for example, a spore, a seed, an egg, a larva, a pupa, or a foetus.

In one preferred embodiment, the subject is a human.

Formulations

While it is possible for the active ingredient to be administered alone, it is preferable to present it as a pharmaceutical composition (e.g., formulation) comprising at least one active ingredient, as defined above, together with one or more pharmaceutically acceptable carriers, excipients, buffers, adjuvants, stabilisers, or other materials well known to those skilled in the art and optionally other therapeutic agents.

Thus, the present invention further provides pharmaceutical compositions, as defined above, and methods of making a pharmaceutical composition comprising admixing at least one active ingredient, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations may be in the form of liquids, solutions, suspensions, emulsions, tablets, losenges, granules, powders, capsules, cachets, pills, ampoules, suppositories, pessaries, ointments, gels, pastes, creams, sprays, foams, lotions, oils, boluses, electuaries, or aerosols.

Formulations suitable for oral administration (e.g., by ingestion) may be presented as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g., transdermal, intranasal, ocular, buccal, and sublingual) may be formulated as an ointment, cream, suspension, lotion, powder, solution, paste, gel, spray, aerosol, or oil. Alternatively, a formulation may comprise a patch or a dressing such as a bandage or adhesive plaster impregnated with active ingredients and optionally one or more excipients or diluents.

Formulations suitable for topical administration in the mouth include losenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations suitable for topical administration to the eye also include eye drops wherein the active ingredient is dissolved or suspended in a suitable carrier, especially an aqueous solvent for the active ingredient.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active ingredient.

Formulations suitable for topical administration via the skin include ointments, creams, and emulsions. When formulated in an ointment, the active ingredient may optionally be employed with either a paraffinic or a water-miscible ointment base. Alternatively, the active ingredients may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active ingredient through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient, such carriers as are known in the art to be appropriate.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active ingredient in the solution is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freese-dried (lyophilised) condition requiring only the addition of the sterile liquid carrier, for example water for injections, immediately prior to use.

Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect.

Administration in vivo can be effected in one dose, continuously or intermittently throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 0.1 to about 250 mg per kilogram body weight of the subject per day. Where the active ingredient is a salt, an ester, prodrug, or the like, the amount administered is calculated on the basis the parent compound and so the actual weight to be used is increased proportionately.

Kits

One aspect of the invention pertains to a kit comprising (a) the active ingredient, preferably provided in a suitable container and/or with suitable packaging; and (b) instructions for use, for example, written instructions on how to administer the active compound, etc.

The written instructions may also include a list of indications for which the active ingredient is a suitable treatment.

EXAMPLES

The following are examples are provided solely to illustrate the present invention and are not intended to limit the scope of the invention, as described herein.

Analytical Methods $^1$H and $^{13}$C NMR spectra were recorded on a Bruker ARX 250 instrument at 250.130 MHz and 62.895 MHz respectively. Melting points were measured on a Galenkamp apparatus and are uncorrected. IR spectra were measured on a Mattson 2020 Galaxy series FT-IR spectrometer. UV spectra were measured on a Pharmacia Biotech Ultraspec 2000 UV/visible spectrophotometer. Mass spectra were recorded on a Micromass Platform spectrometer, or an AEI MS-902 (nominal mass) and a VG Micromass 7070E or Finigan MAT900XLT spectrometer. Merck silica gel 60 (40–60 μM) was used for column chromatography. Dry solvents were used as supplied by Aldrich chem. co. (Gillingham, UK) except THF which was distilled from sodium wire and benzophenone. Tri-t-butyl phosphine and caesium carbonate were supplied from Strem chem co. (Royston, UK); tetrakistriphenylphosphine palladium (0) was prepared according to literature procedure (see, e.g., Coulson, 1990); dry phlorglucinol was supplied by Lancaster Synthesis (Morcambe, UK); all commercially available starting materials were used without further purification. Reactions were carried out under uncontrolled atmosphere unless otherwise stated.

Example 1

6-Chloro-2-methylquinoline hydrochloride/zinc chloride salt (1)

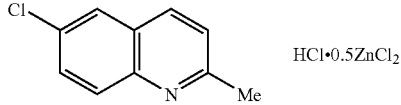

(Method A) 4-Chloroaniline (2.55 g, 20 mmol), concentrated hydrochloric acid (5 cm$^3$), tetrachloro-1-4-benzoquinone (5.9 g, 20 mmol), and n-butanol (5 cm$^3$) were mixed and heated to reflux giving a yellow suspension. Crotonaldehyde (1.68 g, 24 mmol) in butanol (2 cm$^3$) was added over 1 hr giving a dark brown solution. After a further 30 mins reflux, zinc chloride (0.5M in THF, 40 cm$^3$, 20 mmol) was added in three portions and reflux continued for 20 mins before cooling slowly to 0° C. and standing for 1 hr. The dark solid was filtered off, washed with ether, IPA and THF before drying in vacuo to give 6-chloro-2-methylquinoline hydrochloride/zinc chloride salt (3 g, 10.6 mmol, 62%). See, for example, Song et al., 1993.

$^1$H NMR δ (d$_6$ DMSO): 8.9 (1H, d, J=8 Hz), 8.45 (1H, d, J=2.5 Hz), 8.31 (1H, d, J=8 Hz), 8.1 (1H, dd, J=2.5, 8 Hz), 7.98 (1H, d, J=5 Hz), 2.95 (3H, s), mp 237–240° C.

Example 2

6-Fluoro-2-methyl quinoline hydrochloride/zinc chloride salt (2)

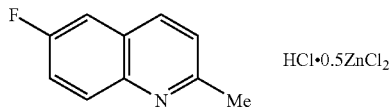

Using a method analogous to Method A, the title compound was prepared (3.36 g, 13.3 mmol, 63%).

$^1$H NMR δ (d$_6$ DMSO): 8.96 (1H, d, J=10 Hz), 8.38 (1H, dd, J=5, 10 Hz), 8.15 (1H, dd, J=2.5, 8.5 Hz), 8.05 (2H, m), 2.96 (3H, s), mp 236–238° C.

Example 3

6-Chloro-2-methyl quinoline (3)

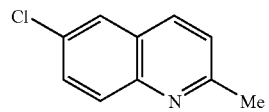

(Method B) (Neutralisation) The title compound, a quinoline free base, was obtained by slurrying the salt, 1, in 2M potassium carbonate at room temperature for 10 min, filtering and extracting the organics into ethyl acetate from the residue. The combined organic washings were dried (MgSO$_4$), filtered and the residue evaporated to give the title compound with quantitative recovery.

$^1$H NMR δ (d$_6$ DMSO): 8.24 (1H, d, J=8 Hz), 8.06 (1H, d, J=2.5 Hz), 7.9 (1H, d, J=9 Hz), 7.73 (1H, dd, J=2.5, 8.5 Hz), 7.47 (1H, d, J=7.5 Hz), 2.63 (3H, s), mp 94–96° C.

Example 4

6-Fluoro-2-methyl quinoline (4)

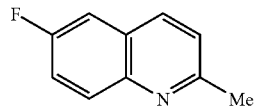

Using a method analogous to Method B, the title compound was prepared from the salt, 2.

$^1$H NMR δ (d$_6$ DMSO): 8.25 (1H, d, J=8.5 Hz), 8.0 (1H, dd, J=5.5, 9.5 Hz), 7.77 (1H, dd, J=3, 9.5 Hz), 7.63 (1H, td, J=3, 11.5 Hz), 7.48 (1H, d, J=7.5 Hz), 2.66 (3H, s), mp 54–56° C.

Example 5

1,2-Dimethyl quinolinium methylsulphate (5)

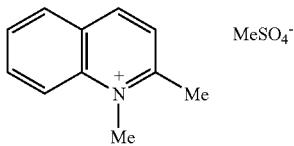

(Method C) (Quinaldinium methyl sulphate salts) Quinaldine (6 g, 41.9 mmol) and dimethyl sulphate (5.28 g, 41.9 mmol, 1 eq) were mixed and heated on a 100° C. oil bath for 5 mins giving a yellow solid. The crude product was recrystallised by dissolving in the minimum amount of methanol at reflux, allowing to cool slightly, precipitating with diethyl ether, cooling, filtering and drying to give the title compound (10.27 g, 38.1 mmol, 91%).

$^1$H NMR δ (d$_6$ DMSO): 9.1 (1H, d, J=8.5 Hz), 8.6 (1H, d, J=9.25 Hz), 8.4 (1H, dd, J=8.5, 1.25 Hz), 8.25 (1H, td, J=7.5, 1.5 Hz), 8.13 (1H, d, J=8.5 Hz), 8.0 (1H, td, J=8, 1 Hz), 4.46 (3H, s), 3.37 (3H, s), 3.09 (3H, s); mp 137–139° C.

Example 6

1,2-Dimethyl-6-chloro quinolinium methyl sulphate (6)

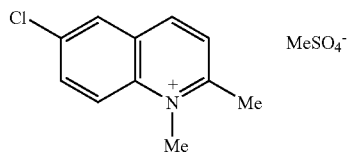

6-Chloro-2-methyl quinoline, 3 (3 g, 16.9 mmol) was alkylated with dimethylsulphate (2.13 g, 16.9 mmol) as above to give the title compound (4.88 g, 16.1 mmol, 95%).

$^1$H NMR δ (d$_6$ DMSO): 9.00 (1H, d, J=8.5 Hz), 8.62 (1H, d, J=9.5 Hz), 8.57 (1H, s, J=2.5 Hz), 8.25 (1H, dd, J=9.5 Hz, 2.5 Hz), 8.16 (1H, d, J=8.5 Hz), 4.45 (3H, s), 3.38 (3H, s), 3.08 (3H, s), mp 145–147° C.

Example 7

1,2,6-Trimethyl quinolinium methyl sulphate (7)

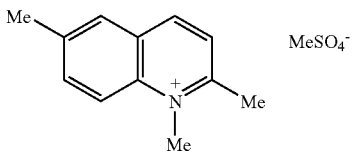

2,6-Dimethylquinoline (4.78 g, 30 mmol) was alkylated with dimethylsulphate (3.78 g, 30 mmol) as above to give the title compound (7.9 g, 28.5 mmol, 95%).

$^1$H NMR δ (d$_6$ DMSO): 8.94 (1H, d, J=10 Hz), 8.46 (1H, d, J=10 Hz), 7.99 (1H, s), 8.15 (1H, s), 7.95 (1H, s), 4.41 (3H, s), 3.37 (3H, s), 3.12 (3H, s), 2.52 (3H, s), mp 140–142° C.

Example 8

1,2-Dimethyl-6-fluoro quinolinium methyl sulphate (8)

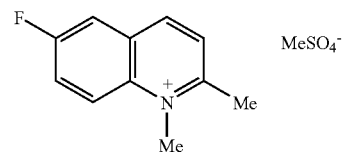

6-Fluoro-2-methylquinoline, 4 (25 g, 0.15 mol) was alkylated with dimethylsulphate (1.89 g, 0.15 mmol) as above to give the title compound (37.5 g, 0.13 mol, 86%).

$^1$H NMR δ (d$_6$ DMSO): 9.04 (1H, d, J=8.75 Hz), 8.7 (1H, dd, J=4.5, 9.75 Hz), 8.26 (1H, dd, J=3, 8.75 Hz), 8.22 (1H, d, J=3 Hz), 8.24 (1H, m), 4.71 (3H, s), 3.37 (3H, s), 3.08 (3H, s), mp 135–137° C.; CHN C$_{11}$H$_{11}$FN.CH$_3$O$_4$S.0.5H$_2$O calc. 48.64, 5.10, 4.73 found C, 48.64; H, 5.10; N, 4.73.

Example 9

6,8,13-Trimethyl-8H-quino[4,3,2-kl]acridinium methyl sulphate (9) (RHPS01)

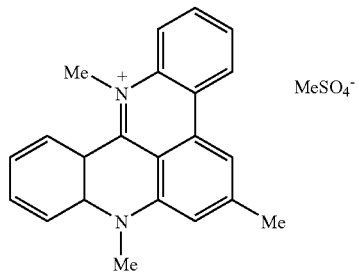

(Method C-1) 1,2-Dimethyl quinolinium methyl sulphate, 5 (2 g, 7.4 mmol) was dissolved in ethanol (20 cm$^3$) at reflux and piperidine (0.63 g, 7.4 mmol, 1 eq) added. Heating was continued for 5 days (TLC 1:1:1 BuOH:AcOH:H$_2$O) until starting material was consumed. The solvent was evaporated under reduced pressure to give a red oil. The product was crystallised from acetone to give the title compound (310 mg, 0.73 mmol, 20%) in two crops (yields take account of bi-molecular reaction). See, for example, Oszczapowicz et al., 1988.

$^1$H NMR δ (d$_6$ DMSO): 8.60 (1H, d, J=7.75 Hz), 8.39 (1H, d, J=8.75 Hz), 8.24 (1H, s), 8.08–7.98 (3H, m), 7.87 (1H, t, J=7.75 Hz), 7.80 (1H, s), 7.70 (1H, t, J=7.50 Hz), 7.58 (1H, dt, J=1.25, 8.00 Hz), 4.36 (3H, s), 4.15 (3H, s), 3.31 (3H, s), 2.83 (3H, s); mp 190–192° C.; IR (KBr disc, cm$^{-1}$) ν 3453, 2945, 2361, 1611, 1530, 1466, 1250, 1245, 1009, 760; UV (EtOH) λ 257 nm (Abs. 1.75); λ 294 nm (Abs. 2.45); λ 325 nm (Abs. 0.75); λ 485 nm (Abs. 1.1); λ 514 nm (Abs. 1.15); MS ES+ 311.1 consistent with C$_{23}$H$_{22}$N$_2$O$_4$S; HRMS C$_{24}$H$_{23}$N$_2$ calc. 339.1861 found 339.1868; CHN crystals from CH$_2$Cl$_2$ C$_{23}$H$_{22}$N$_2$O$_4$S.0.25CH$_2$Cl$_2$ calcd. C, 62.93; H, 5.25; N, 6.31; Found C, 62.76; H, 5.11; N, 6.31.

Example 10

3,11-Dichloro-6,8,13-trimethyl-8H-quino[4,3,2-kl] acridinium methylsulfate (10) (RHPS02)

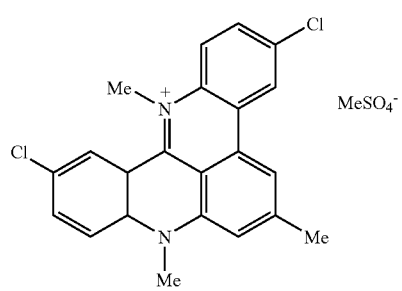

(Method C-2) 6-Chloro-1,2-dimethyl quinolinium methyl sulphate, 6 (600 mg, 2 mmol) was dissolved in ethanol (15 cm$^3$) at reflux and piperidine (0.17 g, 2 mmol, 1 eq) added, and heating continued for 16 hrs. The mixture was allowed to cool, concentrated to 10 cm$^3$ under reduced pressure and the product filtered off to give the title compound (180 mg, 0.37 mmol, 36%).

$^1$H NMR δ (d$_6$ DMSO): 8.87 (1H, d, J=2.25 Hz), 8.55–8.52 (2H, m), 8.24–8.09 (3H, m), 8.00–7.96 (2H, m), 4.37 (3H, s), 4.18 (3H, s), 3.38 (3H, s), 2.78 (3H, s); mp 250–252° C.; IR (KBr disc cm$^{-1}$) ν 3500, 2945, 1610, 1595, 1520, 1220, 1210, 1000, 750; UV (EtOH) λ 257 nm (Abs. 1.75); λ 294 nm (Abs. 2.45); λ 325 nm (Abs. 0.75); λ 485 nm (Abs. 1.1); λ 514 nm (Abs. 1.15); λ 585 nm (Abs. 0.2); MS: ES+ 379.0, 381.5, 383.6, consistent with C$_{23}$H$_{20}$Cl$_2$N$_2$O$_4$S; CHN crystals from MeOH/CHCl$_3$ C$_{23}$H$_{20}$Cl$_2$N$_2$O$_4$S.MeOH Calcd. C, 55.07; H, 4.62; N, 5.35; Found C, 55.29; H, 4.45; N, 5.15.

Example 11

3,6,8,11,13-Pentamethyl-8H-quino[4,3,2-kl]acridinium methyl sulphate (11) (RHPS03)

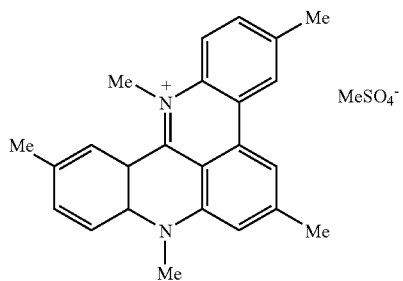

(Method C-2) 1,2,6-Trimethyl quinolinium methyl sulphate, 7 (7.15 g, 0.025 mol) was dissolved in ethanol (200 cm$^3$) at reflux and piperidine (2.5 ml, 0.025 mmol, 1 eq) added. Reflux was continued for 7 days before evaporating and crystallising the product from acetone to give the title compound (705 mg, 1.57 mmol, 12.5%).

$^1$H NMR δ (d$_6$ DMSO): 8.53(1H, s), 8.34 (1H, s), 8.23 (1H, s), 8.03 (1H, d, J=8.75 Hz), 8.0 (1H, d, J=8.75 Hz), 7.9 (2H, m), 7.73 (1H, dd, J=1.75, 7.75 Hz), 4.35 (3H, s), 4.11 (3H, s), 3.39 (3H, s), 2.76 (3H, s), 2.58 (3H, s), 2.56 (3H, s); mp 240–242° C.; IR (KBr disc cm$^{-1}$) ν 3439, 2933, 1616, 1576, 1534, 1250, 1227, 1009, 729; UV (EtOH) λ 257 nm (Abs. 1.75); λ 294 nm (Abs. 2.45); λ 325 nm (Abs. 0.75); λ 485 nm (Abs. 1.1); λ 514 nm (Abs. 1.15); MS: ES+ 339.3 consistent with C$_{25}$H$_{26}$N$_2$O$_4$S; HRMS C$_{22}$H$_{19}$N$_2$ calc. 311.1548 found 311.1545; CHN crystals from CH$_2$Cl$_2$ C$_{25}$H$_{26}$N$_2$O$_4$S.0.75CH$_2$Cl$_2$ Calcd. C, 60.14; H, 5.39; N, 5.45; Found C, 59.65; H, 5.34; N, 5.54.

Example 12

3,11-Difluoro-6,8,13-trimethyl-8H-quino[4,3,2-kl] acridinium methyl sulphate (12) (RHPS04)

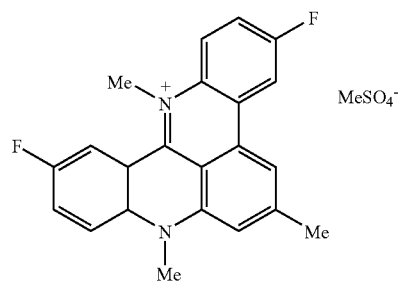

(Method C-4) 1,2-Dimethyl-6-fluoro-quinolinium methyl sulphate, 8 (26.4 g, 90 mmol) was dissolved in ethanol (1.19 L) at reflux and piperidine (9.1 cm$^3$, 90 mmol, 1 eq) added. The mixture was refluxed for 7 days. The solvent was removed under reduced pressure giving a purple oil. The product crystallised from acetone to give the title compound (2.37 g, 5.1 mmol, 11.5%).

$^1$H NMR δ (d$_6$ DMSO): 8.6 (1H, dd, J=3, 9 Hz), 8.42 (1H, s), 8.29 (1H, dd, J=3, 8.5 Hz), 8.23 (1H, t, J=5 Hz), 8.12 (1H, q, J=5 Hz), 8.0 (1H, dt, J=9 Hz 7.95 (1H, s), 7.85 (1H, dt, J=8.5, 4 Hz), 4.37 (3H, s), 4.17 (3H, s), 3.77 (3H, s), 3.38 (3H, s), $^{13}$C NMR (d$_6$ DMSO): 163.28, 159.33, 155.47, 151.95 (d, J=12 Hz), 148.85, 140.95 (d, J=55 Hz), 136.21, 130.97 (d, J=12.75 Hz), 125.61, 125.18 (d, J=37.5 Hz), 122.98 (d, J=36 Hz), 121.07 (d, J=32.5 Hz), 120.37, 119.98, 116.91, 115.93 (d, J=36.25 Hz), 115.07 (d, J=49.25 Hz), 114.87 (d, J=49.25 Hz), 110.76 (d, J=97.25 Hz), 53.85, 46.34, 37.35, 23.43; $^{19}$F NMR δF (d$_6$ DMSO) uncalibrated: −113.42, −117.92; mp 256–258° C.; IR (KBr disc, cm$^{-1}$): ν 3449, 1620, 1584, 1532, 1252, 1225, 1013, 721; UV (EtOH) λ 258 nm (Abs. 1.75); λ 294 nm (Abs. 2.45); λ 325 nm (Abs. 0.75); λ 485 nm (Abs. 1.1); λ514 nm (Abs. 1.15); HRMS C$_{22}$ H$_{17}$ N$_2$ F$_2$ calc 347.1360, found 347.1388; CHN crystals from DCM C$_{22}$ H$_{17}$ N$_2$ F$_2$. CH$_3$SO$_4$.0.5CH$_2$Cl$_2$ calc. C, 56.34; H, 4.23; N, 5.59; found C, 56.91; H, 4.74; N, 4.96. purity confirmed by HPLC.

Example 13

2-(3-Bromo-phenylamino)benzoic acid (13)

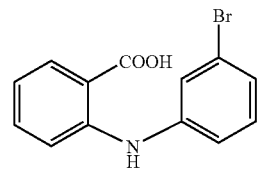

(Method D-1) (Benzoic Acids) (Ullmann Reaction) Under an atmosphere of nitrogen, 2-chlorobenzoic acid (90 g, 0.57 mol), 3-bromoaniline (150 g, 0.87 mol), potassium carbonate (96 g, 0.68 mol) and copper powder (850 mg, 13.4 mmol, catalytic) were mixed in pentanol (130 mL) and heated to reflux for 5 hrs. The pentanol and excess bromoaniline were removed by steam distillation before adding charcoal, filtering hot and cooling. Acidification with 2M HCl (500 mL) gave a grey solid which was collected by filtration. Recrystallisation from ethanol water gave the title compound (81.3 g, 0.28 mol, 49%). See, for example, Hodgeman et al., 1972.

$^1$H NMR δ (d$_6$ DMSO): 13.2 (1H, s), 9.63 (1H, s), 7.93 (1H, dd, J=2.5, 7.5 Hz), 7.46–7.44 (2H, m), 7.32–7.19 (4H, m), 6.88 (1H, dt, J=1, 7.5 Hz); mp 169–171° C., lit. 170–172° C.

Example 14

2-(3-Bromo-phenylamino)-4-chlorobenzoic acid (14)

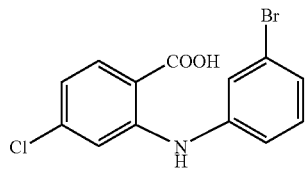

(Method D-2) Under an atmosphere of nitrogen, 2,4-dichlorobenzoic acid (36 g, 0.19 mol), 3-bromoaniline (48 g, 0.28 mol), potassium carbonate (32 g, 0.23 mol), and copper powder (1 g, 0.016 mol, catalytic) were mixed in dry DMF (150 ml) and heated to 150° C. for 18 hrs. The DMF was removed under reduced pressure, water (200 mL) added and the mixture acidified with 2M HCl (400 mL) to give a brown solid which was collected by filtration. Recrystallisation from ethanol/water (60/40) gave the title compound (43 g, 0.116 mol 61%) as a grey solid. See, for example, Hodgeman et al., 1972.

$^1$H NMR δ (d$_6$ DMSO): 9.7 (1H, s), 7.9 (1H, d, 9.5 Hz), 7.5 (1H, s), 7.4 (3H, m), 7.16 (1H, s), 6.9 (1H, d, 3 Hz); mp 205–207° C.

Example 15

1-Bromo-10-methyl-10H-acridin-9-one (15)

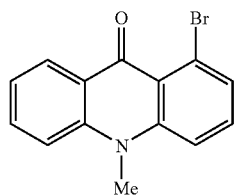

(Method E-1) 2-(3-Bromo-phenylamino)benzoic acid, 13 (9.5 g, 32.5 mmol) was dissolved in conc. sulphuric acid (50 ml) and heated to 100° C. for 40 mins. After cooling, water was added slowly giving a green solid. The solid was filtered off and washed with water, and dried over phosphorous pentoxide. The crude material was partially dissolved in DMF (100 ml) and slowly added under nitrogen to sodium hydride (3.75 g, 156 mmol) in DMF (50 ml), and the mixture stirred for 30 mins. Dimethyl sulphate (12 ml, 72 mmol) was added and stirring continued for a further 30 mins before adding acetic acid (1 ml), then water (400 ml). The precipitate was filtered off, and the crude mix of 1 and 3-bromo acridones separated by column chromatography to give the title compound (2.43 g, 8.86 mmol, 26% over 2 steps). See, for example, Hodgeman et al., 1972.

(Method E-2) (Scaled-up method) 2-(3-Bromo-phenylamino)benzoic acid, 13 (40 g, 137 mmol) was dissolved in c. H$_2$SO$_4$ (600 ml) and treated as above. Methylation as above, triple recrystallisation from benzene gave the title compound (7.9 g, 27.5 mmol, 20% over 2 steps).

$^1$H NMR δ (DMSO): 8.5 (1H, dd, J=1.75, 8 Hz), 7.47 (4H, m), 7.25 (2H, m), 3.86 (1H, s); mp 219–221° C., lit. 221–221.5° C.

Example 16

1-Bromo-6-chloro-10-methyl-10H-acridin-9-one (16)

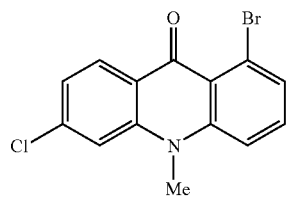

(Method E-3) 2-(3-Bromo-phenylamino)-4-chlorobenzoic acid, 14 (4 g, 12.2 mmol) was heated in conc. H$_2$SO$_4$ (50 ml) for 30 min then allowed to cool to room temperature. Water was added slowly and the precipitate filtered off, washed with water and dried over phosphorous pentoxide. The crude material was suspended in DMF (50 mL) and added under nitrogen to NaH (1.2 g, 50 mmol) in DMF (50 mL). After 30 min dimethylsulphate (3 ml, 18 mmol) was added and stirring continued for 1 hr. Addition of water gave a precipitate the title compound (625 mg, 2.02 mmol, 17%) as the more polar product after separation by column chromatography (ethyl acetate:hexane 1:4)

$^1$H NMR δ (d$_6$ DMSO): 8.1 (1H, s), 7.82 (1H, s), 7.7 (1H, d, J=8 Hz), 7.5 (2H, m), 7.22 (1H, d, J=8 Hz), 3.8 (3H, s); mp 223–225° C.; CHN C$_{14}$H$_9$BrClNO calc. C, 52.13; H, 2.81; N, 4.34; found C, 51.76; H, 2.78; N, 4.02.

Example 17

1-3-Dihydroxy-10H-acridin-9-one (17)

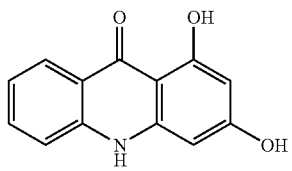

(Method E-4) Methyl anthranilate (90 g, 0.72 mol), anhydrous phlorglucinol (109 g, 0.86 mol), para-toluenesulphonic acid (6 g, 0.035 mol, catalytic) and hexanol (360 ml) were mixed and heated to reflux with Dean-Stark removal of water for 2.5 hrs giving a yellow/orange suspension. After cooling, petroleum ether (40/60°, 2 L) was added and the solid filtered off. The residue was washed with petroleum ether (500 mL) and dichloromethane (150 mL) to give the title compound (149.4 g, 0.66 mmol, 91%). See, for example, Reisch et al., 1991.

¹H NMR δ (d6 DMSO): 14.24 (1H, s), 11.77 (1H, s), 10.56 (1H, s), 8.13 (1H, d, 8 Hz), 7.69 (1H, ddd, J=8.3, 7.8, 1.4 Hz), 7.45 (1H, d, J=8 Hz), 7.23 (1H, ddd, J=8.0, 7.8, 1.4 Hz), 6.27 (1H, d, J=1.6 Hz), 6.0 (1H, d, J=1.6 Hz); mp >300° C. lit. >350° C.

Example 18

6-Chloro-1,3-dihydroxy-10H-acridin-9-one (18)

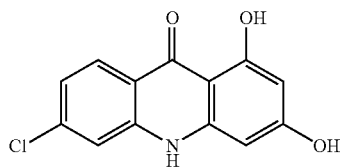

(Method E-5) 2-Amino-4-chlorobenzoate (50 g, 0.27 mol), dry phlorglucinol (40 g, 0.32 mol), hexanol (120 ml), and p-toluene sulphonic acid (1.6 g, 9 mmol) were mixed and heated to reflux with Dean-Stark removal of water for 2 hrs. On cooling petroleum ether (2 L) was slowly added and the solid was filtered off, washed with petroleum ether and dichloromethane to give the title compound (58.8 g, 0.22 mmol, 83.4%).

¹H NMR δ (d₆ DMSO): 14.02 (1H, s), 11.84 (1H, s), 10.61 (1H, s), 8.12 (1H, d), 7.46 (1H, J=2.5 Hz), 7.24 (1H, dd, J=2.5, 7.7 Hz), 6.28 (1H, d, J=2.5 Hz), 6.03 (1H, d, J=2.5 Hz); decomposes 250° C.

Example 19

1-Hydroxy-3-methoxy-10-methyl-10H-acridin-9-one (19)

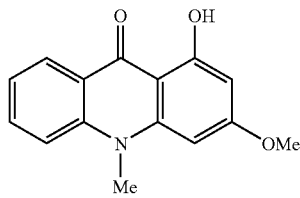

(Method E-6) 1-3-Dihydroxy-10H-acridin-9-one, 17 (42 g, 0.18 mol) and potassium carbonate (69 g, 0.5 mol) were mixed in dry acetone (1.5 L) and iodomethane (150 mL, 0.63 mol) added. The suspension was heated to reflux for 8 hrs, then stirred at room temperature for a further 18 hrs, tlc and NMR samples showing complete reaction. The suspension was filtered, the residue washed well with DCM and the combined filtrates evaporated under reduced pressure. Recrystallisation from DMF, washing with diethyl ether, and drying in vacuo gave the title compound (29.2 g, 0.116 mol, 68%).

¹H NMR δ (CDCl₃): 14.97 (1H, s), 8.39 (1H, d, J=2.5 Hz), 7.67 (1H, t, J=7.5 Hz), 7.41 (1H, d, J=7.5 Hz), 7.23 (1H, m), 6.24 (2H, s), 3.9 (3H, s), 3.73 (3H, s); mp 162–164° C., lit. 164–165° C.

Example 20

6-Chloro-1-hydroxy-3-methoxy-10-methyl-10H-acridin-9-one (20)

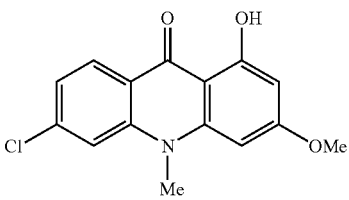

A method analogous to Method E-6, applied to 6-chloro-1,3-dihydroxy-10-methyl-10H-acridin-9-one, 18 (52 g, 0.2 mol), dry acetone (1.75 L), potassium carbonate (80 g, 0.58 mol) and iodomethane (175 ml, 0.74 mol) added for 3 hrs reflux gave complete reaction, work-up and recrystallisation gave the title compound (37 g, 0.13 moles, 65%).

¹H NMR (CDCl₃) δH: 14.65 (1H, s), 8.23 (1H, d, J=7.5 Hz), 7.93 (1H, s), 7.35 (1H, d, J=7.5 Hz), 6.58 (1H, s), 6.3 (1H, s), 3.92 (3H, s), 3.83 (3H, s).

Example 21

Sulfuric acid 3-methoxy-10-methyl-9-oxo-9,10-dihydro-acridin-1-yltrifluoromethyl ester (21)

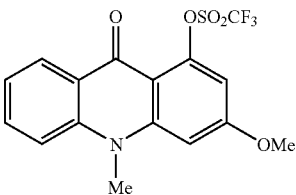

(Method F-1) Under an atmosphere of nitrogen 1-hydroxy-3-methoxy-10-methyl-10H-acridin-9-one, 19 (28 g, 0.116 mol) and N-ethyl diisopropylamine (18.7 mL, 0.116 mol, 1 eq) were partially dissolved in dry DCM (2 L) and the solution cooled to −40° C. Trifluoromethanesulphonic acid anhydride (15.5 mL, 0.116 mol, 1 eq) was slowly added as a solution in DCM (100 mL) and the mixture stirred and allowed to warm slowly to room temperature over 18 hrs. The solution was washed with water, the lower organic layer dried (Na₂SO₄), filtered and evaporated under reduced pressure adsorbing onto silica. The crude was purified by column chromatography (1:4 EtOAc:hexane until the product was eluting, and column wash with neat CHCl₃) to give the title compound (25.4 g, 0.066 moles, 57%).

¹H NMR δ (CDCl₃): 8.5 (1H, dd, 2.5 Hz, 7.5 Hz), 7.65 (1H, dt, 1.5, 6.5 Hz), 7.4 (1H, d, 13 Hz), 7.28 (1H, m), 6.79 (1H, d, 2.5 Hz), 6.6 (1H, d, 2.5 Hz), 3.95 (3H, s), 3.78 (3H, s); ¹³C NMR δ (d₆ DMSO): 173, 161.5, 148.2, 144.5, 140.8, 133.2, 125.2, 121.3, 121.0, 115.22, 107.0, 103.6, 98.2, 55.4, 34.1; mp 189–191° C.; MS EI+ 387; CHN $C_{16}H_{12}F_3NO_5S$ calc. C, 49.62; H, 3.12; N, 3.62; found C, 49.58; H, 3.12; N, 3.49.

Example 22

Sulfuric acid 6-chloro-3-methoxy-10-methyl-9-oxo-9,10-dihydro-acridin-1-yl trifluoromethyl ester (22)

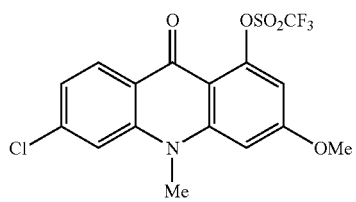

A method analogous to Method F-1, applied to 6-chloro-1-hydroxy-3-methoxy-10-methylacridione, 20 (37 g, 0.128 moles), N-ethyl-diisopropylethylamine (22.5 mL, 0.128 moles, 1 eq), dry DCM (2 L) and trifluormethanesulphonic acid anhydride (21.7 mL, 1 eq) in DCM (100 mL) gave the title compound (32.5 g, 0.077 moles, 57%).

$^1$H NMR δ (CDCl$_3$): 8.46 (1H, d, J=8 Hz), 7.44 (1H, s), 7.24 (1H, d, J=8 Hz), 6.84 (1H, s), 6.6 (1H, s), 3.98 (3H, s), 3.81 (3H, s); $^{13}$C NMR (CDCl$_3$) δC: 206.84, 174.81, 163.12, 150.38, 145.85, 142.70, 140.44, 129.53, 122.73, 121.79, 114.58, 104.55, 98.61; mp 234–236° C.; IR (KBr disc cm$^{-1}$) ν 1643, 1615, 1597, 1463, 1464, 1424, 1306, 1244, 1223, 1200, 1146, 1125, 1069, 995, 922, 833, 810; MS EI+ 421, 423; CHN $C_{16}H_{11}ClF_3NO_5S$ calcd C, 45.56; H, 2.63; N, 3.32; found C, 45.79; H, 2.71; N, 3.16.

Example 23

(2-Pivaloylaminobenzene) boronic acid (23)

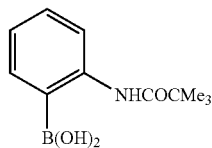

(Method G-1) (Boronic Acids via ortho-lithiation) Under an atmosphere of nitrogen, n-butyllithium (224 mL, 0.56 mol, 2.8 eq) was slowly added to a THF (400 mL) solution of pivaloylaminobenzene (35.4 g, 0.2 mol) at −25° C. After stirring for 6 hrs at ambient temperature trimethyl borate (63.6 mL, 0.56 mol, 2 eq) was added at −25° C. and the mixture allowed to warm to −15° C. and held for 2.5 hrs before aqueous hydrolysis at 0° C. The aqueous layer was separated, washed with dichloromethane (200 mL) and acidified with 2M HCl (150 mL) to give the title compound as a white solid (20.3 g). Further material (4.6 g,) was extracted from the acidic solution with dichloromethane (total 0.11 mol, 56.3%). See, for example, Gullier et al., 1995.

$^1$H NMR δ (d$_6$ DMSO): 10.93 (1H, s,), 7.5 (1H, d, J=7.5 Hz), 7.4 (1H, d, 7.5 Hz), 7.05 (1H, t, J=7.5 Hz), 6.87 (1H, t, J=7.5 Hz), 3.15 (2H, s), 1.16 (9H, s); mp >260° C., lit. >250° C.

Example 24

5-Chloro (2-Pivaloylaminobenzene) boronic acid (24)

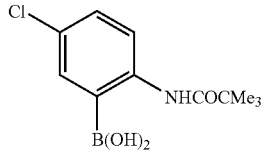

(Method G-2) Under an atmosphere of nitrogen, n-butyllithium (22.75 mL, 2.2 eq) was slowly added to a solution of 4-chloropivaloylamino benzene (16.5 g, 0.078 mol) in dry THF (360 mL) at 0° C. After 2 hrs the mixture was cooled to −78° C. and trimethylborate (19.5 mL, 2.2 eq) slowly added. The mixture was allowed to warm to −15° C. and stirred for 2.5 hrs giving a clear colourless solution. Water (90 mL) was added, the lower, aqueous layer removed, washed with dichloromethane (150 mL) and acidified (90 mL 2M HCl) giving the title compound as a white solid (12.6 g, 0.049 mol, 63.2%). See, for example, Timari et al, 1996.

$^1$H NMR δ (d$_6$ DMSO): 11.35 (1H, s), 7.8 (1H, d, 10 Hz), 7.5 (1H, d, 2.5 Hz), 7.3 (1H, dd, 2.5, 10 Hz), 3.8 (2H, s), 1.19 (9H, s); mp: >260° C., lit. >250° C.

Example 25

2,2-Dimethyl-N-[2-(10-methyl-9-oxo-9,10-dihydro-acridin-1-yl)-phenyl]-propionamide (25)

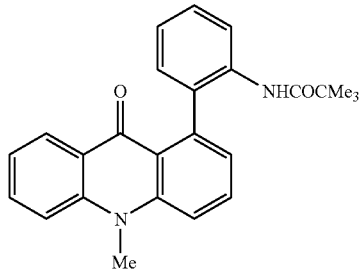

(Method H-1) (Suzuki Route) 1-Bromo-10-methyl-10H-acridin-9-one, 15 (100 mg, 0.35 mmol), (2-pivaloylaminobenzene)boronic acid, 23 (94 mg, 1.2 eq), DME (10 mL), water (2 mL), and sodium hydrogen carbonate (88 mg, 1.05 mmol, 3 eq) were mixed and flushed with nitrogen. Tetrakis (triphenyphosphine)palladium (0) (10 mol %) was added and the mixture heated to reflux for 5 hrs. Water (3 mL) was added and the product extracted with EtOAc (20 mL) then the organic extract dried (MgSO$_4$) filtered and evaporated under reduced pressure to give a yellow oil. This was purified by column chromatograhy (99:1 DCM: MeOH) to give the title compound (120 mg, 0.31 mmol, 88%).

$^1$H NMR δ (CDCl$_3$): 8.34 (1H, d, J=8 Hz), 8.0 (1H, d, J=8.25 Hz), 7.7 (3H, m), 7.54 (1H, d, J=8 Hz), 7.4 (2H, m), 7.22 (1H, d, J=7 Hz), 7.17 (1H, d, J=7 Hz), 7.1 (1H, d, J=6 Hz), 7.0 (1H, d, J=6 Hz), 3.93 (3H, s), 0.9 (9H, s); mp 160–162° C.

Example 26

8-Methyl-8H-quino[4,3,2-kl]acridine (26)

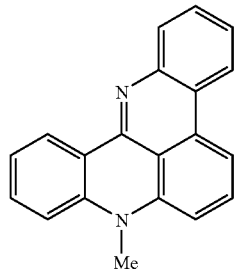

(Method H-2) (Cyclisation) 2,2-Dimethyl-N-[2-(10-methyl-9-oxo-9,10-dihydro-acridin-1-yl)-phenyl]-propionamide, 25 (50 mg, 0.13 mmol) was dissolved in 1:1 THF/6N HCl (20 mL) and the mixture heated to reflux for 5 days giving a bright orange solution. The mixture was basified (aq. $Na_2CO_3$) and extracted with ethyl acetate (50 mL) and the organic layer dried ($Na_2SO_4$), and evaporated under reduced pressure. The crude product was purified by column chromatography (1:4 EtOAc: hexane) to give the title compound as a yellow solid (35 mg, 0.12 mmol, 95%).

$^1$H NMR δ ($CDCl_3$): 8.97 (1H, s), 8.4 (1H, d, J=7.5 Hz), 8.1 (1H, s, 7 Hz), 7.97 (1H, s), 7.83 (1H, t, J=8 Hz), 7.71 (1H, dt, J=1.5, 7.5 Hz), 7.67 (1H, dt, J=0.8, 8 Hz), 7.49 (1H, dt, J=0.75, 8 Hz), 7.3 (2H, m), 7.15 (1H, d, J=8 Hz), 3.72 (s, 3H); $^1$H NMR δ ($d_6$ DMSO): 8.8 (1H, dd, J=1.25, 7.5 Hz), 8.5 (1H, dd, J=1, 7.5 Hz), 8.1 (1H, d, J=8 Hz), 7.88 (2H, m), 7.6 (4H, m), 7.38 (1H, d, J=7.5 Hz), 7.23 (1H, dt, J=1.5, 8 Hz), 3.71 (3H, s); mp 212–214° C.

Example 27

8-Methyl-8H-quino[4,3,2-kl]acridine (27)

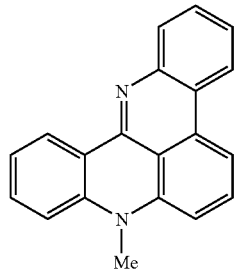

The general coupling procedure (Method I-1), described below, applied to 1-bromo-10-methyl-10H-acridone, 15 (150 mg, 0.55 mmol), (2-pivaloylaminobenzene)boronic acid, 23 (150 mg, 0.68 mmol, 1.2 eq), sodium hydrogen carbonate (60 mg, 0.71 mmol. 1.3 eq), DME (15 mL) and water (3.5 mL) for 4 hrs reflux, and aqueous work-up ($H_2O$, 50 mL, EtOAc, 60 mL) gave a yellow solid.

(Method I-1: General Coupling Procedure) The appropriate 10-methyl-10H-acridin-9-one, 2-(pivaloylaminobenzene)-boronic acid, 23, $NaHCO_3$, DME, and distilled water were mixed and the suspension flushed with nitrogen. Catalytic tetrakis(triphenylphosphine)palladium (0) was added, and the mixture heated to reflux under nitrogen. When all starting material was consumed by tlc, water was added to the cooled mixture, and the organics extracted with ethyl acetate. The organic layer was dried ($MgSO_4$), filtered and evaporated under reduced pressure to give the crude coupled product.

The crude product was cyclised by the general cyclisation procedure B (Method J-2), described below, with phosphorous oxychloride (1 mL), purification by column chromatography giving the title compound (140 mg, 0.50 mmol, 91%). Analysis: ($^1$H NMR and mp) consistent with authentic sample.

(Method J-1: General Cyclisation Procedure A) Phosphorous oxychloride was added to the dry, crude coupling product and the mixture heated in a 100° C. oil bath for 20 mins giving a red solid. The residual solvent was evaporated under reduced pressure, and the solid residue added cautiously to an ammonia ice mix, and stirred vigorously for 10 mins. The solid was filtered off and either purified by column chromatography (adsorption onto silica, 1:4 EtOAc:hexane) or crystallisation.

(Method J-2: General Cyclisation Procedure B) The crude coupling product was dissolved in ethanol, 6M HCl added and the mixture heated to reflux for the desired time. The solvent was evaporated, and 5M HCl added, the solid filtered off, neutralised with sat. aq. sodium hydrogen carbonate and purified to give the desired compound.

Example 28

3-Chloro-8-methyl-8H-quino[4,3,2-kl]acridine (28)

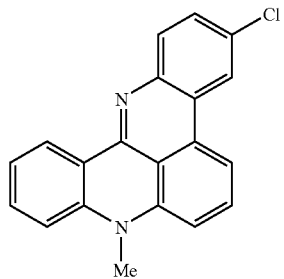

1-Bromo-10-methyl-10H-acridin-9-one, 15 (3 g, 10.9 mmol) and (5-chloro-2-pivaloylaminobenzene) boronic acid, 24 (3.2 g, 12.5 mmol), were coupled by the general coupling procedure (Method I-1) with sodium hydrogen carbonate (1.22 g, 14.5 mmol, 1.4 eq), DME (300 mL) and water (70 mL) and Pd(PPh$_3$)$_4$ (10 mol %) for 4 hrs.

The crude product was cyclised by general cyclisation procedure A (Method J-1) with phosphorous oxychloride (15 mL), purification by column chromatography giving the title compound (2.5 g, 7.9 mmol, 72.4%).

$^1$H NMR δ ($CDCl_3$): 8.84 (1H, dd, J=1.5, 8 Hz), 8.25 (1H, d, J=7.5 Hz), 7.90 (1H, d, J=2 Hz), 6.85 (1H, d, J=8 Hz), 7.65 (1H, t, J=6 Hz), 7.53 (2H, m), 7.23–7.18 (2H, m), 7.03 (1H, d, J=8 Hz), 3.59 (3H, s); $^{13}$C NMR δ ($CDCl_3$): 150, 144.53, 142.02, 141.8, 133.99, 132.20, 132.14, 130.96, 129.83, 126.44, 124.51, 122.55, 122.47, 121.98, 116.5, 114.23, 111.63, 109.15, 34.12; mp 226–228° C.; IR (KBr disc cm$^{-1}$) ν 3442, 2234, 1597, 1551, 1493, 1460, 1354, 1331, 1279, 1233, 1181, 1107, 1080, 1045, 831, 766, 741, 656, 548; CHN $C_{20}H_{13}ClN_2$·0.25$H_2O$ C, 74.77; H, 4.24; N, 8.72. found C, 74.57; H, 4.12; N, 8.68.

Example 29

10-Chloro-8-methyl-8H-quino[4,3,2-kl]acridine (29)

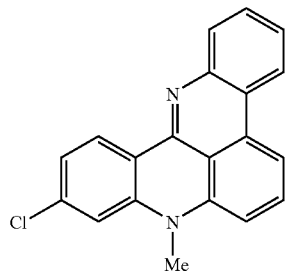

1-Bromo-6-chloro-10-methyl-10H-acridin-9-one, 16 (220 mg, 0.68 mmol) and (2-pivaloylaminobenzene) boronic acid, 23 (173 mg, 0.78 mmol, 1.15 eq) were coupled by the general coupling procedure (Method I-1) with sodium hydrogen carbonate (71 mg, 0.85 mmol, 1.25 eq), Pd(PPh$_3$)$_4$ (94 mg, 0.082 mmol, 12 mol %), DME (20 mL) and water (5 mL) for 18 hrs.

The crude product was cyclised by the general cyclisation procedure B (Method J-2) with ethanol (40 mL) and 6M HCl (60 mL), purification by column chromatography giving the title compound (147 mg, 0.46 mmol, 68%).

$^1$H NMR δ (CDCl$_3$): 8.86 (1H, d, J=8 Hz), 8.40 (1H, dd, J=2, 8 Hz), 8.05–8.0 (2H, m), 7.78 (1H, t, J=8 Hz), 7.67 (1H, dt, J=1.25, 8 Hz), 7.50 (1H, dt, J=1.25, 8 Hz), 7.18 (1H, dd, J=1.75, 8.75 Hz), 7.10 (1H, d, J=8.25 Hz), 3.68 (3H, s); $^1$H NMR δ (d$_6$ DMSO): 8.75 (1H, d, J=8 Hz), 8.58 (1H, d, J=8 Hz), 8.2 (1H, d, J=8 Hz), 7.94–7.87 (2H, m), 7.73–7.76 (2H, m), 7.54 (1H, t, J=8 Hz), 7.43 (1H, d, J=8 Hz), 7.28 (1H, dd, J=2, 8 Hz), 3.70 (3H, s); mp 272–274° C.; IR (KBr disc cm$^{-1}$) ν 2962, 2357, 1606, 1585, 1458, 1261, 1093, 1024, 804; HRMS C$_{20}$H$_{14}$N$_2$Cl calc. 317.084551 found 317.08595

Example 30

3,10-Dichloro-8-methyl-8H-quino[4,3,2-kl]acridine (30)

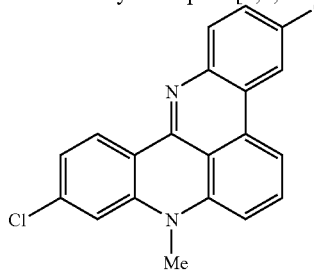

1-Bromo-6-chloro-10-methyl-10H-acridin-9-one, 16 (220 mg, 0.68 mmol) and 5-chloro-(2-pivaloylaminobenzene) boronic acid, 24 (200 mg, 0.78 mmol, 1.15 eq) were coupled by the general coupling procedure (Method I-1) with sodium hydrogen carbonate (71 mg, 0.85 mmol, 1.25 eq), Pd(PPh$_3$)$_4$ (94 mg, 0.082 mmol, 12 mol %), DME (20 mL) and water (5 mL) for 18 hrs.

The crude product was cyclised by the general cyclisation procedure B (Method J-2) with ethanol (40 mL) and 6M HCl (60 mL), purification by column chromatography giving the title compound (143 mg, 0.41 mmol, 60%).

$^1$H NMR δ (d$_6$ DMSO): 8.7 (1H, d, J=8 Hz), 8.62 (1H, s), 8.22 (1H, d, J=7.5 Hz), 7.89 (2H, m), 7.68 (2H, m), 7.45 (1H, d, J=8 Hz), 7.27 (1H, dd, J=2, 8 Hz), 3.69 (3H, s); mp 273–275° C.; IR (KBr disc cm$^{-1}$) ν 1963, 1607, 1589, 1551, 1451, 1422, 1262, 1099, 1022, 820.

Example 31

6-Methoxy-8-methyl-8H-quino[4,3,2-kl]acridine (31)

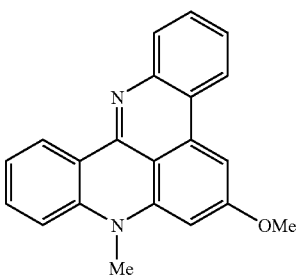

Sulfuric acid 3-methoxy-10-methyl-9-oxo-9,10-dihydro-acridin-1-yl trifluoromethyl ester, 21 (4.5 g, 11.3 mmol) and (2-pivaloylaminobenzene) boronic acid, 23 (3.3 g, 1.2 eq) were coupled by the general coupling procedure (Method I-1) with sodium hydrogen carbonate (1.33 g, 1.4 eq), Pd(PPh$_3$)$_4$ (12 mol %) DME (300 mL) and water (30 mL) for 18 hrs.

The crude product was cyclised by the general cyclisation procedure A (Method J-1) with phosphorous oxychloride (10 mL) purification by column chromatography giving the title compound (1.94 g, 6.2 mmol, 55%).

$^1$H NMR δ (d$_6$ DMSO): 8.6 (1H, d, 8 Hz), 8.4 (1H, d, 8 Hz), 8.27 (1H, s), 8.1 (3H, m), 7.9 (1H, s), 7.8 (1H, s), 7.71 (1H, t, 8 Hz), 7.6 (1H, t, 8 Hz), 4.3 (3H, s), 4.01 (3H, s); $^1$H NMR δ (CDCl$_3$): 8.9 (1H, dd, J=1, 8 Hz), 8.25 (1H, dd, J=1, 8 Hz), 8.0 (1H, dd, J=1, 8 Hz), 7.63 (1H, dt, J=1, 6 Hz), 7.5–7.42 (2H, m), 7.33 (1H, d, J=1.5 Hz), 7.25–7.21 (2H, m), 6.54 (1H, d, J=1.5 Hz); mp 214–216° C.; IR (KBr disc cm$^{-1}$) ν 1606, 1589, 1556, 1464, 1417, 1359, 1329, 1290, 1209, 1168, 1147, 1097, 1047, 821, 798, 752; CHN C$_{21}$H$_{16}$N$_2$O.0.5H$_2$O calculated C, 78.48, H, 5.33, N, 8.72. found C, 78.05; H, 5.08; N, 8.57.

Example 32

3-Chloro-6-methoxy-8H-quino[4,3,2-kl]acridine (32)

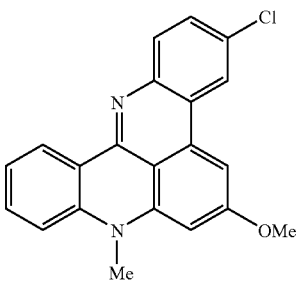

Synthesis 1

Sulfuric acid 3-methoxy-10-methyl-9-oxo-9,10-dihydro-acridin-1-yl trifluoromethyl ester, 21 (6.9 g, 17.4 mmol) and 5-chloro-(2-pivaloylaminobenzene)boronic acid, 24 (5.33 g, 20.9 mmol, 1.2 eq) were coupled by the general coupling procedure (Method I-1) with sodium hydrogen carbonate (2 g, 1.4 eq), DME (200 mL) and water (10 mL) for 18 hrs.

The crude product was cyclised by the general coupling procedure A (Method J-1) with phosphorous oxychloride (10 mL), crystallisation in methanol giving the title compound (3.71 g, 10.7 mmol, 61.5%).

Synthesis 2

Sulfuric acid 3-methoxy-10-methyl-9-oxo-9,10-dihydro-acridin-1-yl trifluoromethyl ester, 21 (18 g, 46.4 mmol) and 5-chloro-(2-pivaloylaminobenzene) boronic acid, 24 (14.8 g, 1.25 eq) were coupled by the general coupling procedure (Method I-1) with sodium hydrogen carbonate (5.3 g, 1.4 eq), Pd(PPh$_3$)$_4$ (6.5 g, 14 mol %), DME (450 mL) and water (22 mL) for 18 hrs.

(Method J-3) The crude material was cyclised with ethanol (100 mL) and 5M HCl (120 ml) for 18 hrs with yellow crystals precipitating. The crude solid was washed before neutralisation (acetone, 150 ml), then neutralised (sat. sodium hydrogencarbonate, 200 mL). The product was dissolved in DCM and dried (MgSO$_4$), filtered and evaporated under reduced pressure. Trituration with hexane and filtration gave the title compound as a yellow solid (11.2 g, 33.2 mmol, 70%).

$^1$H NMR δ (CDCl$_3$): 8.80 (1H, dd, J=1.5, 8 Hz), 8.08 (1H, d, J=2.25 Hz), 7.86 (1H, d, J=8 Hz), 7.5–7.45 (2H, m), 7.23–7.14 (2H, m), 7.05 (1H, d, J=2 Hz), 6.4 (1H, d, J=2 Hz), 3.91 (3H, s), 3.44 (3H, s); mp 205–207° C.; IR (KBr disc cm$^{-1}$) ν 1601, 1554, 1462, 1415, 1327, 1288, 1209, 1157, 1105, 1057, 817, 746, 721, 651, 542; MS FAB+ 347, HRMS C$_{21}$H$_{16}$ClN$_2$O calc. 349.092641, 347.094835 found 349.092166, 347.095116; CHN C$_{21}$H$_{15}$ClN$_2$O.1.5H$_2$O calculated C, 67.47 H, 4.85 N, 7.49 found C, 67.81; H, 4.18; N, 7.61.

Example 33

10-Chloro-6-methoxy-8H-quino[4,3,2-kl]acridine (33)

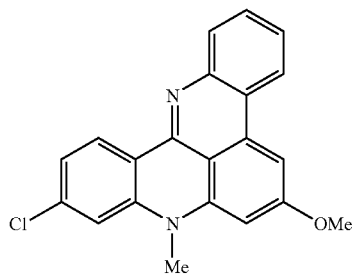

Sulfuric acid 6-chloro-3-methoxy-10-methyl-9-oxo-9,10-dihydro-acridin-1-yl trifluoromethyl ester, 22 (3.5 g, 8.3 mmol) and (2-pivaloylaminobenzene) boronic acid, 23 (2.33 g, 10.4 mmol) were coupled by the general coupling procedure (Method I-1) with sodium hydrogen carbonate (1.05 g, 1.4 eq), Pd(PPh$_3$)$_4$ (12 mol %), DME (230 mL) and water (23 mL) for 18 hrs.

The crude product was cyclised by general cyclisation procedure A (Method J-1) with phosphorous oxychloride (5 mL), purification by column chromatography giving the title compound (1.45 g, 4.2 mmol, 50%).

$^1$H NMR δH (DMSO): 8.7 (1H, d, J=8.5 Hz), 8.55 (1H, d, J=7.75 Hz), 7.86 (1H, d, J=8.25 Hz), 7.61 (3H, m), 7.5 (1H, t, J=7.5 Hz), 7.24 (1H, d, J=8.75 Hz), 6.88 (1H, s), 4.04 (3H, s), 3.64 (3H, s); mp 240–242° C.; IR (KBr disc cm$^{-1}$) ν 2933, 1606, 1587, 1440, 1284, 1211, 1168, 1058, 817, 761, 650; MS AP+ 347.4, 349.4; CHN C$_{21}$H$_{15}$ClN$_2$O.1.5H$_2$O calculated C, 72.73; H, 4.36; N, 8.08; found C, 72.13; H, 4.37; N, 8.02.

Example 34

3,10-Dichloro-6-methoxy-8-methyl-8H-quino[4,3,2-kl]acridine (34)

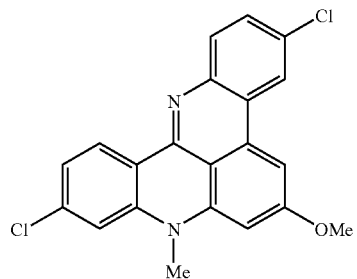

Sulfuric acid 6-Chloro-3-methoxy-10-methyl-9-oxo-9,10-dihydro-acridin-1-yl trifluoromethyl ester, 22 (287 g, 0.68 mmol) and 5-chloro-(2-pivaloylaminobenzene) boronic acid, 24 (200 g, 0.78 mmol, 1.15 eq) were coupled by the general coupling procedure (Method I-1) with sodium hydrogen carbonate (71 g, 0.85 mmol, 1.25 eq), Pd(PPh$_3$)$_4$ (94 mg, 12 mol %), DME (12 mL) and water (0.5 mL) for 18 hrs.

The crude material was cyclised by the general cyclisation procedure B (Method J-2) with ethanol (5 mL) and 5M HCl (5 ml) for 18 hrs at reflux, purification by column chromatography giving a yellow solid the title compound (113 mg, 0.30 mmol, 58%).

$^1$H NMR δ (d$_6$ DMSO): 8.69–8.65 (2H, m), 7.84 (1H, d, J=8 Hz), 7.66–7.6 (3H, m), 7.25 (1H, d, J=8 Hz), 6.87 (1H, s), 4.04 (3H, s), 3.62 (3H, s); mp 287–289° C.; IR (KBr disc cm$^{-1}$) ν 1585, 1548, 1406, 1211, 1107, 1047, 871, 819, 650; CHN C$_{21}$H$_{14}$Cl$_2$N$_2$O.0.75H$_2$O calc. C, 63.89; H, 3.98; N, 7.10; found C, 64.01; H, 3.86; N, 6.66.

Example 35

6-Hydroxy-8-methyl-8H-quino[4,3,2-kl]acridine (35)

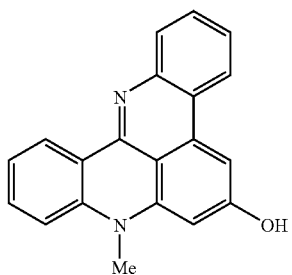

The general procedure (Method K, described below) applied to 6-methoxy-8-methyl-8H-quino[4,3,2-kl]acridine, 31 (400 mg, 1.28 mmol), dry benzene (100 ml) aluminium chloride (900 mg), methanol (100 ml), sat. aq. sodium hydrogen carbonate (40 ml), and ethyl acetate (100 ml) gave the title compound (381 mg, 1.27 mmol, 99.7%).

(Method K) (Demethylation) The appropriate 6-methoxyquinoacridine was suspended in benzene and anhydrous aluminium chloride added (3 eq). The mixture was heated to 80° C., giving a red oily suspension and bright green haze on the solvent, until complete reaction was seen by tlc (0.2 mL sample, 0.5 mL methanol quench, 0.2 mL sat. aq. NaHCO$_3$ neutralisation, neat EtOAC eluent) then allowed to cool to room temperature. Methanol was added slowly with ice cooling of the suspension and the stirring continued until all red oil was gone. The solvent was evaporated under reduced pressure, and the residue treated with sat. aq. sodium hydrogen carbonate. The organics were separated form the crude filtrate by soxhlet extraction with ethyl acetate. Filtration of the precipitate on cooling gave the desired compound.

$^1$H NMR δ (d$_6$ DMSO): 8.74 (1H, d, J=7.5 Hz), 8.26 (1H, d, J=7 Hz), 7.8 (1H, d, J=8.5 Hz), 7.57 (4H, m), 7.39 (2H, m), 7.21 (1H, t, J=6.5 Hz), 6.75 (1H, s), 3.62 (3H, s); decomposes at 250° C.; IR (KBr disc cm$^{-1}$) ν 2928, 1604, 1589, 1462, 1429, 1352, 1292, 1205, 760, 746.

Example 36

3-Chloro-6-hydroxy-8-methyl-8H-quino[4,3,2-kl]acridine (36)

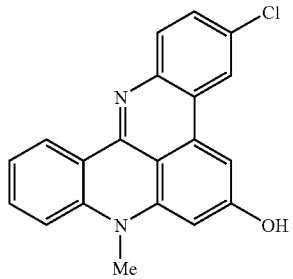

The general procedure (Method K) applied to 3-chloro-6-methoxy-8-methyl-8H-quino[4,3,2-kl]acridine, 32 (5.5 g, 15.9 mmol), with aluminium chloride (6.3 g, 3 eq), and benzene (500 ml) gave the title compound as a yellow solid (4.5 g, 13.5 mmol, 88%).

$^1$H NMR δ (d$_6$ DMSO): 8.72 (1H, d, J=7.25 Hz), 8.31 (1H, s), 7.8 (1H, d, J=8.75 Hz), 7.62 (3H, m), 7.41 (1H, s), 7.24 (1H, t, J=6.75 Hz), 6.82 (1H, s), 3.64 (3H, s); decomposes 150° C.; (KBr disc cm$^{-1}$) ν 2928, 1595, 1460, 1288, 1180, 1107, 833, 746; CHN C$_{20}$H$_{13}$ClN$_2$ calc. C, 72.18; H, 3.94; N, 8.42; found C, 71.89; H, 3.95; N, 7.98.

Example 37

10-Chloro-6-hydroxy-8-methyl-8H-quino[4,3,2-kl]acridine (37)

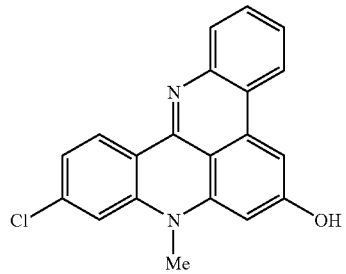

The general procedure (Method K) applied to 10-chloro-6-methoxy-8-methyl-8H-quino[4,3,2-kl]acridine, 33 (2.6 g, 7.5 mmol), with aluminium chloride (3.2 g, 3 eq), and benzene (500 ml) gave the title compound a yellow solid (2.43 g, 7.3 mmol, 98%).

$^1$H NMR δ (d$_6$ DMSO): 10.54 (1H, s), 8.72 (1H, d, J=7.50 Hz), 8.32 (1H, d, J=7.50 Hz), 7.85 (1H, d, J=7.5 Hz), 7.68–7.62 (2H, m), 7.53–7.44 (2H, m), 7.26 (1H, dd, J=1.00, 7.50 Hz), 6.79 (1H, d, J=1 Hz), 3.62 (3H, s); mp decomposes 270° C.; IR (KBr disc cm$^{-1}$) ν 2922, 1620, 1560, 1477, 1440, 1365, 1232, 1041, 806, 746; MS AP+ 333.4.

Example 38

Trifluoromethanesulphonic acid 3-chloro-8-methyl-8H-quino[4,3,2-kl]acridin-6-yl ester (38)

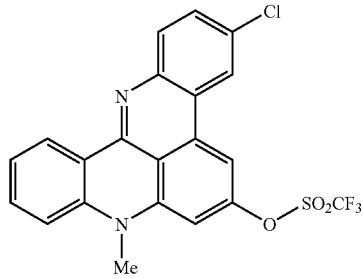

(Method L) Under an atmosphere of nitrogen, trifluoromethanesulphonic acid anhydride (1.14 ml, 6.4 mmol, 1 eq) was added dropwise to a stirred cold (0° C.) suspension of 3-chloro-6-hydroxy-8-methyl-8H-quino[4,3,2-kl]acridine, 36 (2.23 g, 6.4 mmol) in DCM (1 L). On warming to RT a green solution was formed. Aqueous work-up (water, 500 mL), separation of the organic layer, drying (MgSO$_4$), filtering, adsorption onto silica, and column chromatography (85:15 hexane:ethyl acetate) gave the title compound as a yellow solid, (2 g, 4.3 mmol, 67%).

$^1$H NMR δ (CDCl$_3$): 8.8 (1H, dd, J=1, 8 Hz), 8.16 (1H, d, J=2 Hz), 7.96 (1H, d, J=9 Hz), 7.61 (3H, m), 7.32 (2H, m), 6.9 (1H, d), 3.66 (3H, s); mp 193–195° C.; IR (KBr disc cm$^{-1}$) ν 1597.16, 1554.72, 1421.63, 1327.11, 1222.95, 1205.59, 1136.14, 974.11, 925.89, 869.95, 841.02, 761.93, 599.90; MS AP+ 465.3, 467.3; CHN $C_{21}H_{12}ClF_3N_2O_3S \cdot 0.5H_2O$ calculated C, 53.23; H, 2.77; N, 5.91; found C, 53.06; H, 2.58; N, 5.74.

Example 39

Trifluoromethanesulphonic acid 10-chloro-8-methyl-8H-quino[4,3,2-kl]acridin-6-yl ester (39)

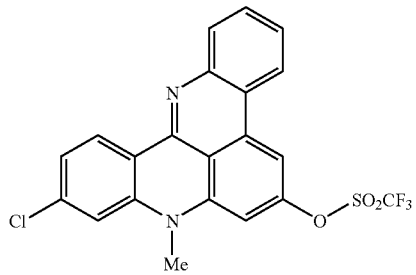

The general procedure (Method L) applied to trifluoromethanesulphonic anhydride (0.05 ml, 0.3 mmol, 1 eq), 10-chloro-6-hydroxy-8-methyl-8H-quino[4,3,2-kl]acridine, 37 (100 mg, 0.3 mmol) in DCM (50 mL) gave the title compound as a yellow solid, (114 mg, 0.25 mmol, 81%).

$^1$H NMR δ (CDCl$_3$): 8.78 (d, 1H), 8.23 (1H, dd, J=2, 8 Hz), 8.02 (1H, dd, J=2, 8 Hz), 7.72 (2H, m), 7.54 (1H, m), 7.17 (2H, m), 6.81 (1H, d, J=2 Hz); mp 239–241° C.; IR (KBr disc cm$^{-1}$) ν 1597, 1421, 1217, 1138, 983, 827, 746; MS AP+ 465.3, 467.3; CHN $C_{21}H_{12}ClF_3N_2O_3S \cdot 1.5H_2O$ calculated C, 51.28; H, 3.07; N, 5.70. found C, 51.48; H, 3.07; N, 5.40.

Example 40

(E)-3-(8-Methyl-8H-quino[4,3,2-kl]acridin-3-yl) acrylic acid methyl ester (40)

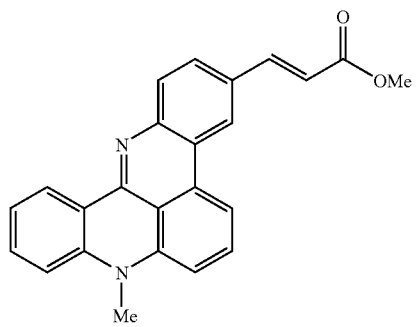

The general procedure (Method M, described below) applied to 3-chloro-8-methyl-8H-quino[4,3,2-kl]acridine, 28 (160 mg, 0.5 mmol) and methyl acrylate (0.064 mL, 1.5 eq) gave the title compound (120 mg, 0.33 mmol, 66%).

(Method M; Heck Reaction) The chloro substituted 8-methyl-8H-quino[4,3,2-kl]acridine, potassium phosphate (2 eq), tris(dibenzylideneacetone)dipalladium (0) (2 mol %), tri-t-butyl phosphine (0.05 M in dioxane, 8 mol %), and the appropriate alkene were mixed in a screw-top tube and flushed with nitrogen. The tube was sealed and the mixture heated to reflux (170° C. oil bath) for 48 hrs. The reaction was allowed to cool to room temperature, DCM added and the suspension filtered through celite, washing with copious DCM. The products were adsorbed onto silica by evaporation under reduced pressure and purified by column chromatography (5% methanol in DCM), the combined alkene fractions evaporated under reduced pressure. Trituration with ether and filtration gave the desired compounds as red/orange solids.

$^1$H NMR δ (d$_6$ DMSO): 8.87 (1H, s), 8.76 (1H, d, J=8 Hz), 8.25 (1H, d, J=8 Hz), 8.0 (1H, d, J=8 Hz), 7.86 (3H, m), 7.62 (2H, m), 7.4 (1H, d, J=8 Hz), 7.24 (1H, t, J=6 Hz), 6.78 (1H, d, J=12.5 Hz), 3.79 (3H, s), 3.72 (3H, s); mp 252–254° C.; IR (KBr disc cm$^{-1}$) ν 1693, 1688, 1589, 1551, 1514, 1503, 1464, 1443, 1425, 1362, 1352, 1333, 1262, 1209, 1173, 1154, 1096, 1082, 1045, 824; HRMS FAB+ $C_{24}H_{19}N_2O_2$ calculated 367.144653 found 367.144554.

Example 41

3-(8-Methyl-8H-quino[4,3,2-kl]acridin-3-yl)propionic acid methyl ester (41)

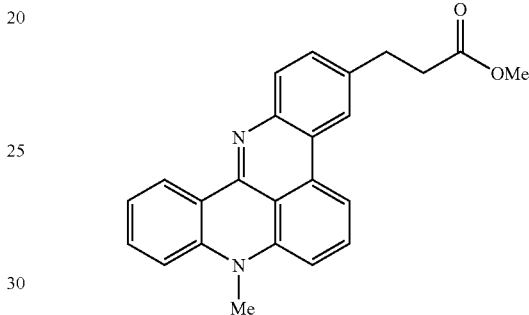

(Method N) (E)-3-(8-Methyl-8H-quino[4,3,2-kl]acridin-3-yl)-acrylic acid methyl ester, 40 (50 mg, 0.14 mmol) was suspended in ethyl acetate (150 mL) and shaken under pressure of hydrogen (40 psi) with 10% palladium on carbon (100 mg) for 2 days. The mixture was filtered through celite, the solvent evaporated under reduced pressure, the product adsorbed onto silica and purified by column chromatography (1:4 EtOAc:hexane) to give the title compound (36 mg, 0.098 mmol, 70%).

$^1$H NMR δ (CDCl$_3$): 2.7 (2H, t, 6 Hz), 3.18 (2H, 2, 6 Hz), 3.6 (3H, s), 3.7 (3H, s), 7.0 (1H, d, 8 Hz), 7.2 (2H, m), 7.5 (2H, m), 7.7 (1H, m), 7.9 (2H, m), 8.16 (1H, s), 8.9 (1H, d, 8 Hz).

Example 42

(E)-3-(8-methyl-8H-quino[4,3,2-kl]acridin-3-yl) acrylonitrile (42)

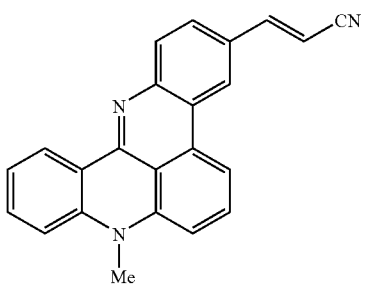

The general procedure (Method M) applied to 3-chloro-8-methyl-8H-quino[4,3,2-kl]acridine, 28 (300 mg, 0.94 mol) and acrylonitrile (0.144 mL, 2 eq) gave the title compound (193 mg, 0.58 mmol, 62%).

¹H NMR δ (DMSO): 8.84 (1H, s), 8.8 (1H, d, J=8 Hz), 8.22 (1H, d, J=8 Hz), 8.0–7.92 (3H, m), 7.77 (1H, d, J=16.8 Hz), 7.71–7.63 (2H, m), 7.48 (1H, d, J=8 Hz), 7.30 (1H, dt, J=1.5, 6 Hz), 6.68 (1H, d, J=16.8 Hz), 3.78 (3H, s); mp 262–264° C.; HRMS FAB+ C₂₃H₁₆N₃ calc 334.134423 found 334.133351; IR (KBr disc cm⁻¹) ν 2963, 2922, 2864, 1721, 1603, 1589, 1543, 1510, 1460, 1443, 1352, 1329, 1283, 1262, 1175, 1094, 1075, 1042, 1026.

Example 43

(E)-3-(8-Methyl-8H-quino[4,3,2-kl]acridin-3-yl)acrylamide (43)

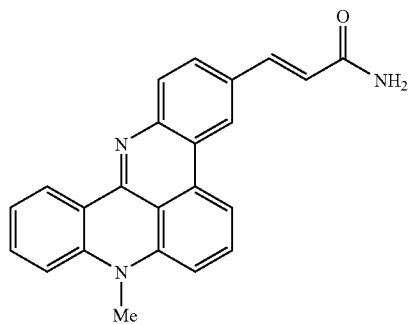

The general procedure (Method M) applied to 3-chloro-8-methyl-8H-quino[4,3,2-kl]acridine, 28 (100 mg, 0.32 mmol) and acrylamide (46 mg, 2 eq) gave the title compound (102 mg, 0.29 mmol, 91%).

¹H NMR δ (DMSO): 8.80 (1H, d, J=8 Hz), 8.72 (1H, s), 8.23 (1H, d, J=8 Hz), 7.94–7.88 (3H, m), 7.73–7.64 (3H, m), 7.58 (1H, s, br NH), 7.44 (1H, d, J=8 Hz), 7.29 (1H, dt, J=1.5, 6.5 Hz), 7.17 (1H, s, br NH), 8.73 (1H, d, J=17.8 Hz), 3.74 (3H, s); mp 284–286° C.; IR (KBr disc cm⁻¹) ν 2965, 1678, 1605, 1589, 1551, 1508, 1468, 1443, 1429, 1412, 1387, 1354, 1331, 1283, 1262, 1098, 1082, 1026, 831; HRMS FAB+ C₂₃H₁₈N₃O calc. 352.144987 found 352.144821

Example 44

(E)-3-(8-Methyl-8H-quino[4,3,2-kl]acridin-3-yl)-1-morpholin-4-yl-propenone (44)

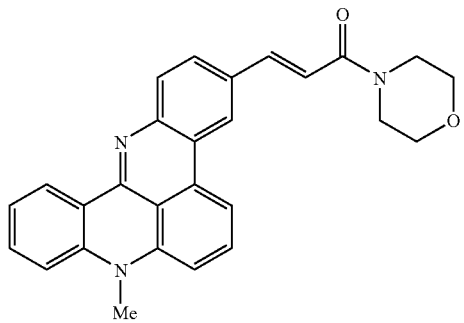

The general procedure (Method M) applied to 3-chloro-8-methyl-8H-quino[4,3,2-kl]acridine, 28 (100 mg, 0.32 mmol) and acryloylmorpholine (0.08 mL, 1.5 eq) gave the title compound (124 mg, 0.29 mmol, 92%).

¹H NMR δ (DMSO): 8.86 (1H, s), 8.81 (1H, d, J=8 Hz), 8.32 (1H, d, J=8 Hz), 8.09 (1H, d, J=8 Hz), 7.96–7.88 (2H, m), 7.79 (1H, d, J=15 Hz), 7.67–7.91 (2H, m), 7.48 (1H, d, J=7.25 Hz), 7.43 (1H, s), 7.26 (1H, m, J=2, 6 Hz), 3.82 (2H, s, br), 3.75 (3H, s), 3.65 (6H, s, br); mp 251–253° C.; MS AP+ 422.4, 335.3; CHN C₁₇H₂₃N₃O₂.0.5H₂O calc. C, 75.33; H, 5.62; N, 9.76; found C, 75.26; H, 5.55; N, 9.88.

Example 45

(E)-3-(3-Chloro-8-methyl-8H-quino[4,3,2-kl]acridin-6-yl)-1-morpholin-4-yl-peopenone (45)

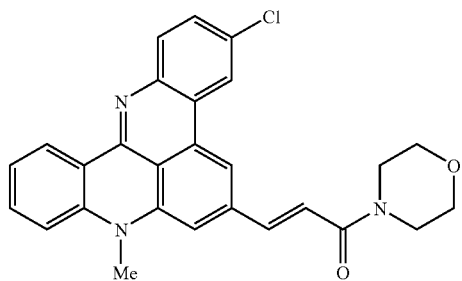

(Method O) A 3-neck flask was charged with trifluoromethanesulphonic acid 3-chloro-8-methyl-8H-quino[4,3,2-kl]acridin-6-yl ester, 38 (200 mg, 0.43 mmol), 4-acryloylmorpholine (108 μL, 2 eq), palladium acetate (10 mg, 10 mol %), triphehylphosphine (22 mg, 20 mol %), triethylamine (72 μL, 1.2 eq), and dioxane (2 mL), the flask flushed with nitrogen and the mixture heated to reflux for 18 hrs, tlc showing complete conversion. On cooling DCM (20 mL) was added and the suspension filtered through celite with copious washings. Adsorption onto silica and column chromatography (1:1 ethyl acetate:hexane to 99:1 ethyl acetate:methanol), evaporation of the combined fractions, and trituration with ether gave the title compound as an orange solid (195 mg, 0.42 mmol, 99%).

¹H NMR δ (DMSO): 8.76–8.73 (2H, m), 8.52 (1H, s), 7.88 (1H, t, J=6.5 Hz), 7.7–7.6 (6H, m), 7.28 (1H, m, J=2, 6.5 Hz), 3.87 (2H, s), 3.78 (3H, s, br), 3.57 (6H, s, br); mp decomposes; IR (KBr disc cm⁻¹) ν 2858, 1649, 1592, 1591, 1554, 1419, 1332, 1259, 1224, 1114, 1043, 825.

Example 46

(E)-3-(6-Methoxy-8-methyl-8H-quino[4,3,2-kl]acridin-10-yl)-1-morpholin-4-yl-propenone (46)

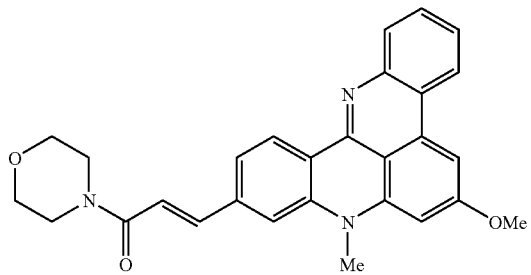

The general procedure (Method M) applied to 10-chloro-6-methoxy-8-methyl-8H-quino[4,3,2-kl]acridine, 39 (200 mg, 0.58 mmol) and 4-acryloylmorpholine (147 µL, 2 eq) gave the title compound (226 mg, 0.50 mmol, 86%).

$^1$H NMR δ (DMSO): 8.75 (1H, d, J=8 Hz), 8.56 (1H, d, J=8 Hz), 7.90 (1H, d, J=8 Hz), 7.83 (1H, s), 7.73–7.64 (4H, m), 7.52–7.43 (2H, m), 6.88 (1H, s), 4.05 (3H, s), 3.81 (2H, s, br), 3.72 (3H, s), 3.65 (6H, s, br); $^{13}$C NMR δH (DMSO): 164.7, 162.8, 156.4, 148.1, 145.7, 143.0, 141.7, 138.5, 136.0, 129.5, 128.8, 127.6, 125.6, 124.8, 123.6, 122.8, 122.15, 120.4, 119.5, 115.2, 114.0, 111.7, 66.6, 55.9, 45.9, 34.0; mp 248–150° C.; IR (KBr disc cm$^{-1}$) ν 1641, 1606, 1444, 1211, 1113, 815

Example 47

Acetic acid 3-[(E)-3-(3-morpholin-4-yl-3-oxo-propenyl)-8-methyl-8H-quino[4,3,2-kl]acridin-6-yl]-propyl ester (47)

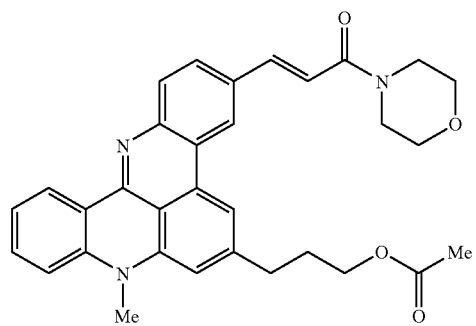

The general procedure (Method M) applied to acetic acid 3-(3-chloro-8-methyl-8H-quino[4,3,2-kl]acridin-6-yl)-propyl ester, 49 (100 mg, 0.247 mmol) and 4-acryloylmorpholine (70 mg, 63 µL, 2 eq) gave the title compound (104 mg, 0.2 mmol, 83%). Purity was checked by tlc.

Example 48

N-[(E)-3-(3-Chloro-8-methyl-8H-quino[4,3,2-kl]acridin-6-yl)-allyl]-trifluoroacetamide (48)

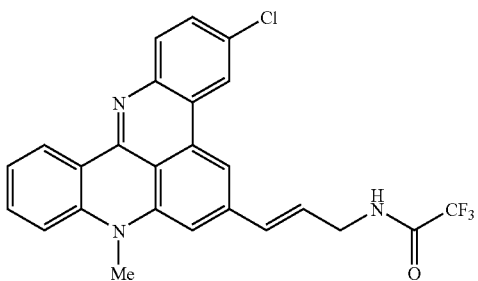

(Method P) Under an atmosphere of nitrogen, trifluoromethanesulphonic acid 3-chloro-8-methyl-8H-quino[4,3,2-kl]acridin-6-yl ester, 38 (30 mg, 0.075 mmol), allyltrifluoroacetamide (17 mg, 1.5 eq), palladium (II) acetate (2 mg, 10 mol %), triphenyl phosphine (4 mg, 20 mol %), dicyclohexylamine (0.032 mL, 2 eq), and dioxane were mixed in a sealed tube and heated reflux in a sealed tube for 18 hrs. On cooling, the products were dissolved in dichloromethane and adsorbed onto silica. Separation of the more polar product by column chromatography (85:15 hexane: ethyl acetate) gave the title compound (22 mg, 0.045 mmol, 60%).

$^1$H NMR δ (d$_6$ acetone): 8.65 (1H, s), 8.63 (1H, dd, J=2, 8 Hz), 8.29 (1H, d, J=2.5 Hz), 7.9 (1H, s), 7.71 (1H, d, J=10 Hz), 7.44 (2H, m), 7.32 (1H, d, J=10 Hz), 7.13 (1H, s), 7.07 (1H, dt J=1, 8 Hz), 6.6 (2H, m), 4.1 (2H, t, J=7.5 Hz), 3.54 (3H, s); mp

Example 49

Acetic acid 3-(3-chloro-8-methyl-8H-quino[4,3,2-kl]acridin-6-yl)propyl ester (49)

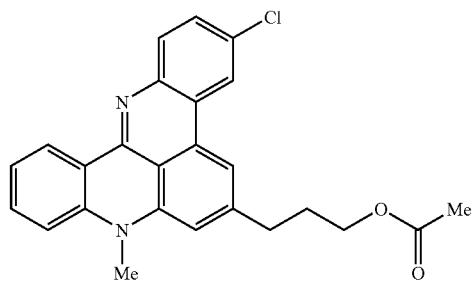

The general procedure (Method Q and R-1, described below) applied to allyl acetate (0.37 mL, 3.44 mmol, 4 eq), 9-BBN (3.4 mL, 2 eq) with 3.5 hrs RT stirring, then trifluoromethanesufonic acid 3-chloro-8-methyl-8H-quino[4,3,2-kl]acridin-6-yl ester, 38 (400 mg, 0.86 mmol) and dioxane (10 mL) gave the title compound (210 mg, 0.51 mmol, 60%).

(Method Q) Preparation of Alkyl Boranes: The desired alkene was slowly added to 9-borabicyclo[3.3.1]nonane (9-BBN) (0.5M in THF) and the solution cooled to 0° C., before allowing to warm to room temperature and stirring.

(Method R-1) Coupling Reaction: Aryl triflates: The appropriate aryl triflate electrophile, palladium acetate (10 mol %), triphenyl phosphine (20 mol %), $Cs_2CO_3$ (2 eq), and dioxane were combined and the mixture heated to 100° C. for 16 hrs. On cooling, DCM was added and the products adsorbed onto silica, and eluted by column chromatography (4:1 hexane:ethyl acetate to 3:1 heaxane:ethyl acetate), the combined fractions evaporated, the product triturated with hexane and the resulting solid collected by filtration.

(Method R-2) Coupling Reaction: Aryl chlorides: The appropriate chloroalkyl-8-methyl-8H-quino[4,3,2-kl]acridine electrophile, tris(dibenzylideneacetone)dipalladium (0) (4 mol %), tri-t-butyl phosphine (8 mol %) in dioxane (0.05M), $Cs_2CO_3$ (2 eq), and dioxane were added to the mixture and the reaction heated to 150° C. for 18 hrs. On cooling, DCM was added and the products adsorbed onto silica, and eluted by column chromatography the combined fractions evaporated, the product triturated with hexane and the resulting solid collected by filtration.

All reactions were carried out under nitrogen $^1$H NMR δ (d$_6$ DMSO): 8.73 (1H, d, J=8 Hz), 8.60 (1H, d, J=2 Hz), 8.03 (1H, s), 8.86 (1H, d, J=8 Hz), 7.7–7.55 (3H, m), 7.27–7.22 (2H, m), 4.12 (2H, t, J=6 Hz), 3.69 (3H, s), 2.92 (2H, t, J=7.5 Hz), 2.08 (2H, m), 2.06 (3H, s); $^{13}$C NMR δ (d$_6$ DMSO): 170.0, 148.9, 146.0, 143.4, 140.8, 140.6, 132.5, 131.7, 129.9, 128.8, 128.7, 124.6, 123.5, 122.1, 120.8, 120.4, 114.5, 113.9, 111.1, 109.8, 63.0, 33.2, 32.3, 29.1, 20.3; mp 152–154° C.; IR (KBr disc cm$^{-1}$) v 2930, 1740, 1613, 1590, 1553, 1462, 1358, 1339, 1233, 1098, 1044; MS AP+ 417.4.

Example 50

Acetic acid 3-(10-chloro-8-methyl-8H-quino[4,3,2-kl]acridin-6-yl)propyl ester (50)

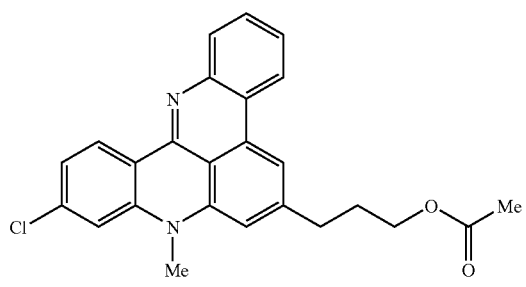

The general procedure (Method Q and R-1) applied to allyl acetate (0.17 mL, 1.58 mmol, 3.7 eq), 9-BBN (2 mL, 2.3 eq) with 3.5 hrs RT stir, then trifluoromethanesufonic acid 10-chloro-8-methyl-8H-quino[4,3,2-kl]acridin-6-yl ester, 39 (200 mg, 0.43 mmol) and dioxane (5 mL) gave the title compound (110 mg, 0.27 mmol, 63%).

$^1$H NMR δ (CDCl$_3$): 8.86 (1H, d, J=8 Hz), 8.38 (1H, dd, J=2, 8 Hz), 8.02 (1H, d, 2, 8 Hz), 8.41 (1H, s), 7.67 (1H, dt, J=1.5, 6 Hz), 7.49 (1H, dt, J=1.3, 8 Hz), 7.18 (1H, dd, J=2, 8 Hz), 6.93 (1H, s), 4.21 (2H, t, J=6.5 Hz), 3.65 (3H, s), 2.95 (2H, t, J=7.5 Hz), 2.14 (2H, m), 2.1 (3H, s); mp 162–164° C.; MS AP+ 417.3; IR (KBr disc cm$^{-1}$) v 2955, 1736, 1607, 1586, 1489, 1364, 1250, 1036, 870; CHN $C_{25}H_{21}ClN_2O_2 \cdot 2/3H_2O$ calc. C, 70.01; H, 5.25; N, 6.53; found C, 70.10; H, 5.64; N, 5.85.

Example 51

Acetic acid 3-[3-(3-acetoxy-propyl)-8-methyl-8H-quino[4,3,2-kl]acridin-6-yl]-propyl ester (51)

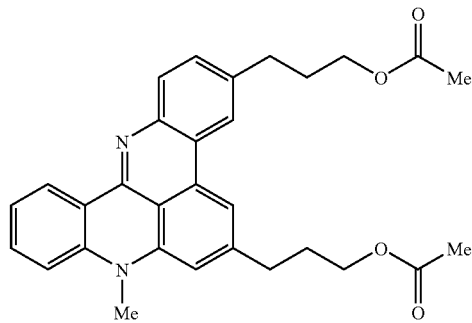

The general procedure (Method Q and R-2) applied to allyl acetate (0.17 mL, 1.55 mmol, 2.1 eq), 9-BBN (3 mL, 2 eq) with 3.5 hrs RT stir, then acetic acid 3-(3-chloro-8-methyl-8H-quino[4,3,2-kl]acridin-6-yl)-propyl ester, 49 (300 mg, 0.74 mmol) and dioxane (3 mL) gave the title compound (45 mg, 0.096 mmol, 13%). Purity was checked by tlc.

Example 52

Acetic acid 3-[10-(3-acetoxy-propyl)-8-methyl-8H-quino[4,3,2-kl]acridin-6-yl]-propyl ester (52)

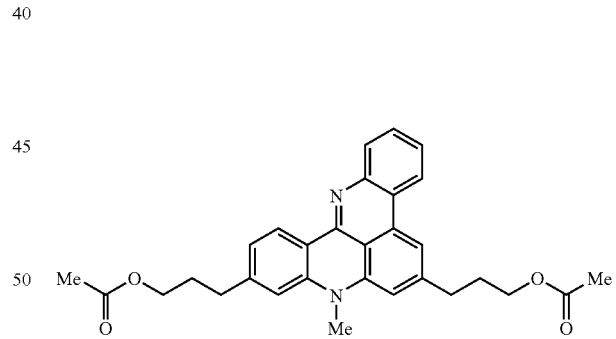

The general procedure (Method Q and R-2) applied to allyl acetate (0.083 mL, 0.77 mmol, 1.2 eq), 9-BBN (1.54 mL, 0.77 mmol 1.2 eq) with 3.5 hrs RT stir, then acetic acid 3-(10-chloro-8-methyl-8H-quino[4,3,2-kl]acridin-6-yl)propyl ester, 50 (260 mg, 0.64 mmol) gave the title compound (60 mg, 0.13 mmol, 20%).

$^1$H NMR δ (CDCl$_3$): 8.87 (1H, d, J=8 Hz), 8.4 (1H, dd, J=1.5, 8 Hz), 8.05 (1H, dd, J=1, 8 Hz), 7.83 (1H, s), 7.67 (1H, dt, J=1.3, 7 Hz), 7.49 (1H, dt, J=1.5, 7 Hz), 7.11 (2H, m), 6.95 (1H, s), 4.2 (4H, m), 3.76 (3H, s), 2.96 (2H, t, J=7.5 Hz), 2.83 (2H, t, 7.5 Hz), 2.1 (10H, m).

Example 53

N-[3-(3-Chloro-8-methyl-8H-quino[4,3,2-kl]acridin-6-yl)-propargyl]-2,2,2-trifluoroacetamide (53)

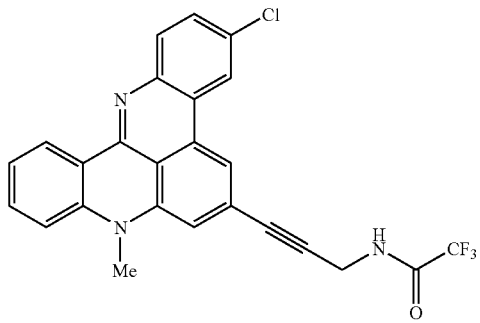

(Method S) Trifluoromethanesufonic acid 3-chloro-8-methyl-8H-quino[4,3,2-kl]acridin-6-yl ester kl]acridine, 38 (100 mg, 0.22 mmol), propargyltrifluoroacetamide (65 mg, 2 eq), triethylamine (57 µL, 2 eq), copper iodide (33 mg, 0.17 mmol), tetrakistriphenylphosphine palladium (0) (53 mg, 20 mol %) and dioxane (10 mL) were mixed and the flask flushed with nitrogen. The reaction was heated to reflux for 18 hrs giving complete conversion by tlc. Dissolution in DCM (20 mL), adsorption onto silica and column chromatography (1:7 to 1:3 ethyl acetate in hexane) gave the title compound as a yellow solid (84 mg, 0.18 mmol, 83%).

$^1$H NMR δ (d$_6$ DMSO): 10.23 (1H, s), 8.76 (1H, dd, J=1.5, 8 Hz), 8.7 (1H, d, J=2 Hz), 8.27 (1H, d, J=2 Hz), 7.92 (1H, d, J=8 Hz), 7.7 (3H, m), 7.39 (1H, s), 7.3 (1H, dt, J=1.5, 6.5 Hz), 4.44 (2H, s), 3.72 (3H, s); mp 255–257° C.; IR (KBr disc cm$^{-1}$) ν 1710, 1606, 1589, 1554, 1462, 1207, 1184, 1151, 1105, 696, 653, 613; CHN C$_{24}$H$_{15}$ClF$_3$N$_3$O$_2$.2H$_2$O calc. C, 59.83; H, 3.82; N, 8.37; found C, 59.74; H, 3.08; N, 8.34.

Example 54

8-Methyl-8H-quino[4,3,2-kl]acridine-3-carbonitrile (54)

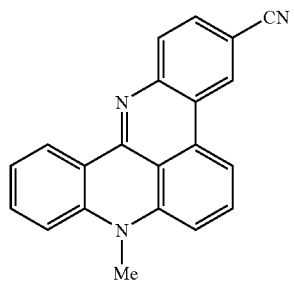

(Method T) 3-Chloro-8-methyl-8H-quino[4,3,2-kl]acridine, 28 (150 mg, 0.47 mmol), tris(dibenzylideneacetone) dipalladium (0) (9 mg), bisdiphenylphosphino ferrocene (17 mg), zinc powder (5 mg), zinc cyanide (33 mg) and DMA were mixed in a sealed tube, flushed with nitrogen, the tube sealed and the mixture heated to 100° C. for 3 days. The cooled mixture was taken up in dichloromethane (50 mL), washed with 2M ammonium hydroxide (20 mL) and water (20 mL), dried, filtered, evaporated and purified by column chromatography to the title compound (147 mg, 0.46 mmol, 99%).

$^1$H NMR δ (CDCl$_3$): 8.93 (1H, d, J=7.25 Hz), 8.65 (1H, s), 8.0 (1H, d, J=8 Hz), 7.9 (1H, t, J=8 Hz), 7.8 (1H, t, J=7.5 Hz), 7.63 (1H, t, J=7.5 Hz), 7.38–7.13 (3H, m), 3.73 (3H, s).

Example 55

8,13-Dimethyl-8H-quino[4,3,2-kl]acridinium iodide (55) (RHPS05)

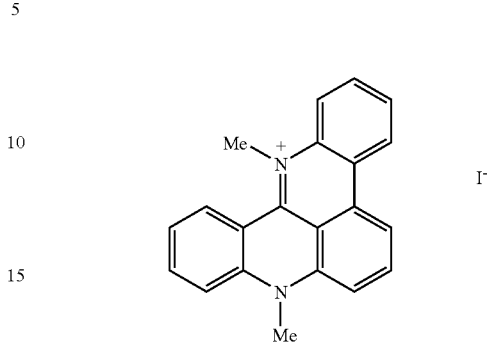

The general procedure with work-up A applied to 8-methyl-8H-quino[4,3,2-kl]acridine (100 mg, 0.35 mmol), 26, and methyl iodide (2 mL) for 2 days gave the title compound (118 mg, 0.28 mmol, 79%).

(Method U) Methylation: General Procedure: The appropriate 8-methyl-8H-quino[4,3,2-kl]acridine was mixed with methyl iodide in a sealed tube and heated to 100° C. for the given time. On cooling the product was:

(A): Collected by filtration and washed with diethyl ether; or, (B): Dissolved in DCM and purified by column chromatography (5–10% MeOH in DCM); or, (C): Dissolved in DCM and purified by preparative tlc (5% MeOH in DCM).

$^1$H NMR δ (DMSO): 8.78 (1H, dd, J=1, 6 Hz), 8.52 (2H, t, J=6 Hz), 8.34 (1H, t, J=8 Hz), 8.13 (4H, m), 7.95 (1H, dt, J=1,6 Hz), 7.8 (1H, dt, J=1,6 Hz), 7.64 (1H, dt, J=1,6 Hz), 4.47 (3H, s), 4.2 (3H, s); mp 214–216° C., IR (KBr disc cm$^{-1}$) 3478, 2934, 2492, 1655, 1640, 1487, 1458, 1341, 1161, 1090, 947, 752 CHN Crystals from CHCl$_3$ C$_{21}$H$_{17}$N$_2$.I.2/3CHCl$_3$ calc. C, 51.65; H, 3.53; N, 5.56; found C, 51.40; H, 3.72; N, 5.72.

Example 56

3-Chloro-8,13-dimethyl-8H-quino[4,3,2-kl]acridinium iodide (56) (RHPS06)

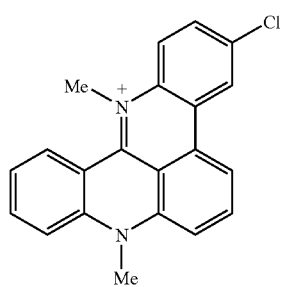

The general procedure (Method U) with work-up (A) applied to 3-chloro-8-methyl-8H-quino[4,3,2-kl]acridine, 28 (100 mg, 0.32 mmol) and methyl iodide (2 mL) for 2 days gave the title compound (118 mg, 0.26 mmol, 80%).

$^1$H NMR δ (DMSO): 8.9 (1H, d, J=2 Hz), 8.7 (1H, d, J=8 Hz), 8.6 (1H, d, J=8 Hz), 8.37 (1H, t J=8 Hz), 8.2 (4H, m), 8.0 (1H, dd, J=3, 8 Hz), 7.65 (1H, t, J=8 Hz), 4.4 (3H, s), 4.2 (3H, s); mp 225–227° C.; IR (KBr disc cm$^{-1}$) ν 3451 (br), 2924, 1611, 1584, 1532, 1460, 1449, 1400, 1354, 1428, 1165, 1096, 1043, 818, 770, 727, 660; HRMS C$_{21}$H$_{17}$ClN$_2$$^{35}$Cl calc. 333.097251 found 333.097219 $^{37}$Cl calc 331.100201 found 331.100201; CHN crystals from CH$_2$Cl$_2$ C$_{21}$H$_{17}$ClN$_2$.I.2CH$_2$Cl$_2$ calc C, 43.95; H, 3.21; N, 4.46; found C, 44.65; H, 3.11; N, 4.86.

Example 57

10-Chloro-8,13-dimethyl-8H-quino[4,3,2-kl]acridinium iodide (57) (RHPS14)

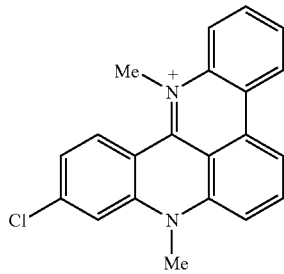

The general procedure (Method U) with work-up (B) applied to 10-chloro-8-methyl-8H-quino[4,3,2-kl]acridine, 29 (50 mg, 0.16 mmol) and methyl iodide (2 mL) for 2 days gave the title compound (21 mg, 0.046 mmol, 30%).

$^1$H NMR δ (DMSO): 8.81 (1H, d, J=7.25 Hz), 8.60 (1H, d, J=7.75 Hz), 8.52 (1H, d, J=9.25 Hz), 8.37 (1H, t, J=8.50 Hz), 8.19 (1H, d, J=8.50 Hz), 8.10 (1H, d, J=8.75 Hz), 7.97 (1H, t, J=7.25 Hz), 7.81 (1H, t, J=7.00 Hz), 7.67 (1H, dd, J=2.25, 9 Hz), 4.41 (3H, s), 4.18 (3H, s); mp 205–207° C.

Example 58

3,10-Dichloro-8,13-dimethyl-8H-quino[4,3,2-kl]acridinium iodide (58) (RHPS07)

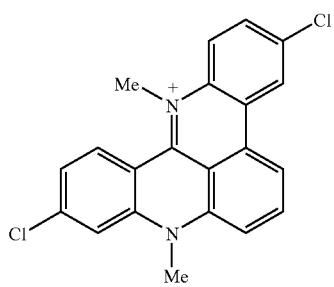

The general procedure (Method U) with work-up (C) applied to 3,10-dichloro-8-methyl-8H-quino[4,3,2-kl]acridine, 30 (32 mg, 0.087 mmol) and methyl iodide (2 mL) for 2 days gave the title compound (15 mg, 0.03 mmol, 35%).

$^1$H NMR δ (DMSO): 8.89 (1H, s), 8.65 (1H, d, J=7.75 Hz), 8.50 (1H, d, J=8.5 Hz), 8.39–8.32 (2H, m), 8.19–8.11 (2H, m), 7.98 (1H, dd, J=1, 8.75 Hz), 4.37 (3H, s), 4.18 (3H, s); mp decomposes >200° C.

Example 59

8,13-Dimethyl-6-methoxy-8H-quino[4,3,2-kl]acridinium iodide (59) (RHPS08)

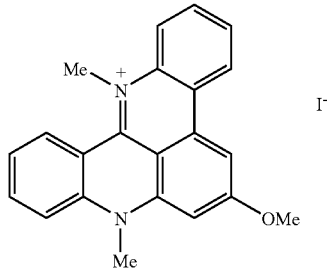

The general procedure (Method U) with work-up (A) applied to 6-methoxy-8-methyl-8H-quino[4,3,2-kl]acridine, 31 (50 mg, 0.16 mmol) and methyl iodide (2 mL) for 2 days gave the title compound (63 mg, 0.14 mmol, 88%).

$^1$H NMR δ (DMSO): 8.7 (1H, d, J=8 Hz), 8.4 (1H, d, J=8 Hz), 7.9 (5H, m), 7.7 (1H, t, J=8 Hz), 7.6 (1H, t, J=8 Hz), 7.35 (3H, s), 4.3 (3H, s), 4.17 (3H, s), 4.1 (3H, s); mp 208–210° C., IR (KBr disc cm$^{-1}$) ν 1611, 1580, 1532, 1468, 1346, 1248, 1206; HRMS C$_{22}$H$_{19}$N$_2$O calc. 327.149738 found 327.151131

Example 60

3-Chloro-8,13-dimethyl-6-methoxy-8H-quino[4,3,2-kl]acridinium iodide (60) (RHPS10)

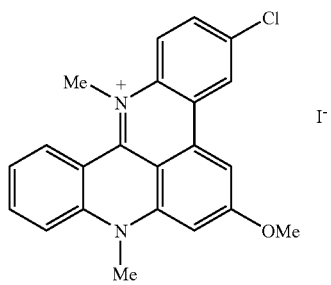

The general procedure (Method U) with work-up (A) applied to 3-chloro-8,13-dimethyl-6-methoxy-8-methyl-8H-quino[4,3,2-kl]acridine, 32 (100 mg, 0.28 mmol) and methyl iodide (2 mL) for 3 days gave the title compound (94 mg, 0.19 mmol, 69%).

$^1$H NMR δ (DMSO): 8.93 (1H, d, J=2 Hz), 8.44 (1H, dd, J=1, 8 Hz), 8.1 (4H, m), 7.94 (1H, dd, J=2.5, 8 Hz), 7.61 (1H, t, J=7.5 Hz), 7.45 (1H, d, J=3 Hz), 4.33 (3H, s), 4.2 (3H, s), 4.06 (3H, s); mp 203–205° C.

Example 61

10-Chloro-8,13-dimethyl-6-methoxy-8H-quino[4,3,2-kl]acridinium iodide (61) (RHPS12)

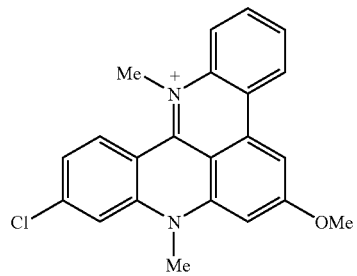

The general procedure (Method U) with work-up (A) applied to 10-chloro-8,13-dimethyl-6-methoxy-8-methyl-8H-quino[4,3,2-kl]acridine, 33 (50 mg, 0.14 mmol) and methyl iodide (2 mL) for 2 days gave the title compound (41 mg, 0.084 mmol, 60%).

$^1$H NMR δ (DMSO): 8.80 (1H, d, J=7.5 Hz), 8.44 (1H, d, J=8.75 Hz), 8.24 (1H, s), 8.1 (2H, m), 7.95 (1H, t, J=8 Hz), 7.75 (1H, t, J=7.75 Hz), 7.61 (1H, d, J=8.75 Hz), 7.42 (3H, s), 4.3 (3H, s), 4.16 (3H, s), 4.03 (3H, s); mp decomposes 170° C., MS FAB+ 361.

Example 62

6-Methoxycarbonyloxy-8,13-dimethyl-8H-quino[4,3,2-kl]acridinium iodide (62) (RHPS13)

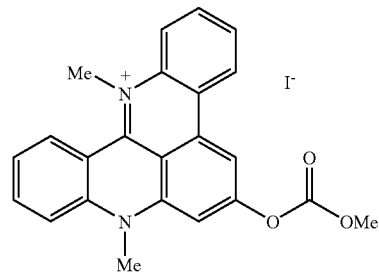

(Method V) Methylchloroformate (0.02 mL, 0.28 mmol) was added slowly to a suspension of 6-hydroxy-8-methyl-8H-quino[4,3,2-kl]acridine, 35 (70 mg, 0.24 mmol) and triethylamine (0.04 mL, 0.28 mmol, 1.2 eq) in DCM (50 mL) at room temperature and stirred for 18 hrs. The solution was washed with water (50 mL), the organic layer separated, dried (MgSO$_4$), filtered and evaporated. The crude product was mixed with methyl iodide (2 mL) in a sealed tube and heated at 100° C. for 3 days. On cooling the product was filtered off, and washed with ether to give the title compound (78 mg, 0.16 mmol, 66% over 2 steps).

$^1$H NMR δ (DMSO): 8.74 (1H, d, J=7.5 Hz), 8.43 (1H, d, J=8 Hz), 8.13–8.0 (4H, m), 7.92 (1H, t, J=7.5 Hz), 7.72 (1H, t, J=7.5 Hz), 7.59 (1H, t, J=7.5 Hz), 7.37 (1H, d, J=2 Hz), 4.32 (3H, s), 4.17 (3H, s), 4.1 (3H, s); $^{13}$C NMR δ (DMSO): 165.6, 151.3, 143.2, 142.5, 138.9, 135.5, 133.9, 132.0, 129.8, 127.1, 124.8, 122.7, 122.1, 119.5, 117.4, 114.7, 112.0, 102.0, 98.1, 56.9, 45.8, 36.5; mp 199–201° C.; IR (KBr disc cm$^{-1}$) ν 1612, 1579, 1467, 1248, 1222, 1205, 1014, 761.

Example 63

6-Acetoxy-8,13-dimethyl-8H-quino[4,3,2-kl]acridinium iodide (63) (RHPS11)

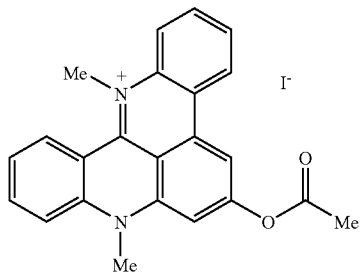

(Method W) Acetyl chloride (0.02 mL, 0.28 mmol) was added slowly to a suspension of 6-hydroxy-8-methyl-8H-quino[4,3,2-kl]acridine, 35 (70 mg, 0.24 mmol) and triethylamine (0.04 mL, 0.28 mmol, 1.2 eq) in DCM (50 mL) at room temperature and stirred for 18 hrs. The solution was washed with water (50 mL), the organic layer separated, dried (MgSO$_4$), filtered and evaporated. The crude product was mixed with methyl iodide (2 mL) in a sealed tube and heated at 100° C. for 3 days. On cooling the product was filtered off, and washed with ether to give the title compound (92 mg, 0.19 mmol, 79% over 2 steps).

$^1$H NMR δ (d$_6$ DMSO): 8.74 (1H, d, J=7.50 Hz), 8.53 (1H, d, J=8.75 Hz), 8.42 (1H, s), 8.21–8.10 (3H, m), 7.99 (1H, t, J=8.50 Hz), 7.93 (1H, s), 7.79 (1H, t, J=7.50 Hz), 7.65 (1H, t, J=8.00 Hz), 4.42 (3H, s), 4.15 (3H, s), 2.43 (3H, s); mp decomposes; IR (KBr disc cm$^{-1}$) ν 1742, 1615, 1584, 1532, 1466, 1425, 1343, 1244, 1211, 1177, 1101, 1049, 1017; MS FAB+ 355.

Example 64

(E)-3-(8,13-Dimethyl-8H-quino[4,3,2-kl]acridinium-3-yl)-acrylic acid methyl ester iodide (64) (RHPS15)

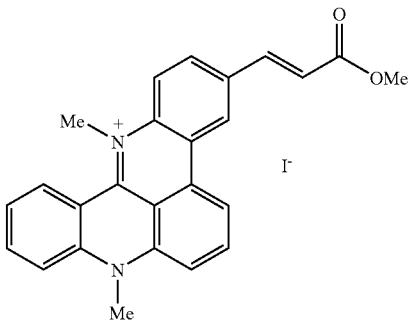

The general procedure (Method U) with work-up (A) applied to (E)-3-(8-methyl-8H-quino[4,3,2-kl]acridin-3-yl)-acrylic acid methyl ester, 40 (30 mg, 0.082 mmol) and methyl iodide (2 mL) for 2 days gave the title compound (25 mg, 0.049 mmol, 60%).

$^1$H NMR δ (d$_6$ DMSO): 9.10 (1H, s), 8.66 (1H, d, J=8 Hz), 8.52 (1H, d, J=9.5 Hz), 8.406 (1H, t, J=8.25 Hz), 8.23 (1H, t, J=9 Hz), 8.13 (4H, m), 7.83 (1H, d, J=16 Hz), 7.65 (1H, t, J=7 Hz), 7.041 (1H, d, J=16 Hz), 4.35 (3H, s), 4.21 (3H, s), 3.79 (3H, s); mp 200–202° C.; IR (KBr disc cm$^{-1}$) ν 1613, 1584, 1256, 1177, 1096; MS FAB+ 381; HRMS C$_{25}$H$_{21}$N$_2$O$_2$calc. 381.1603 found 381.1608

Example 65

3-(8,13-Dimethyl-8H-quino[4,3,2-kl]acridinium-3-yl)-propionic acid methyl ester iodide (65) (RHSP09)

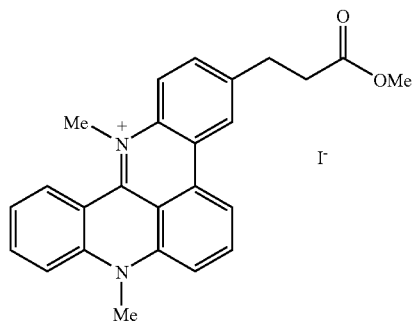

The general procedure (Method U) with work-up (A) applied to 3-(8-methyl-8H-quino[4,3,2-kl]acridin-3-yl)-propionic acid methyl ester, 41 (30 mg, 0.081 mmol) and methyl iodide (2 mL) for 2 days gave the title compound (21 mg, 0.039 mmol, 48%).

$^1$H NMR δ (d$_6$ DMSO): 8.67 (1H, s), 8.47 (2H, m), 8.31 (1H, m), 8.1 (4H, m), 7.83 (1H, d, 8 Hz), 7.63 (1H, d, 6 Hz), 4.39 (3H, s), 4.19 (3H, s), 3.62 (3H, s), 3.15 (2H, m), 2.7 (2H, m); mp decomposes; IR (KBr disc cm$^{-1}$) ν 2963, 1611, 1437, 1260, 1094, 1024; HRMS C$_{25}$H$_{23}$N$_2$O$_2$ calc. 383.175953 found 383.176224.

Example 66

8,13-Dimethyl-(E)-3-(3-morpholin-4-yl-3-oxo-propenyl)-8H-quino[4,3,2-kl]acridinium iodide (66) (RHPS16)

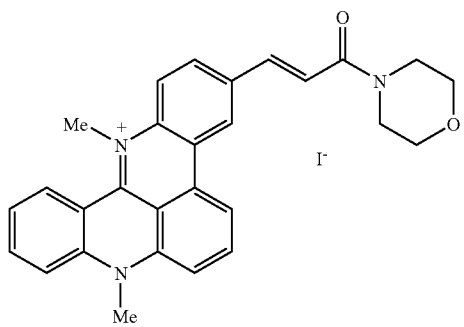

The general procedure (Method U) with work-up (A) applied to (E)-3-(8-methyl-8H-quino[4,3,2-kl]acridin-3-yl)-1-morpholin-4-yl-propenone, 44 (50 mg, 0.12 mmol) and methyl iodide (2 mL) for 2 days gave the title compound (38 mg, 0.067 mmol, 57%).

$^1$H NMR δ (d$_6$ DMSO): 8.99 (1H, s), 8.63 (1H, d, J=8 Hz), 8.5 (1H, d, J=8 Hz), 8.36 (1H, t, J=8 Hz), 8.25 (1H, t, J=8 Hz), 8.22 (1H, s), 8.11 (4H, m), 7.75 (1H, d, J=15 Hz), 7.62 (1H, t, 7.5 Hz), 7.56 (1H, d, J=15 Hz), 4.4 (3H, s), 4.2 (3H, s), 3.84 (2H, s, br), 3.65 (6H, br, s); mp decomposes 240° C.; IR (KBr disc cm$^{-1}$) ν 1613, 1584, 1254, 1117, 1011; MS FAB+ 436.

Example 67

3-Chloro-8,13-dimethyl-(E)-6-(3-morpholin-4-yl-3-oxo-propenyl)-8H-quino[4,3,2-kl]acridinium iodide (67) (RHSP21)

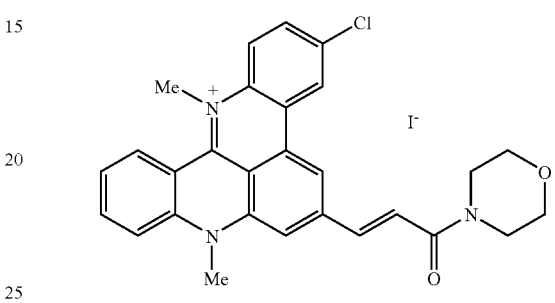

The general procedure (Method U) with work-up (B) (final eluent 15% MeOH/DCM, 1%AcOH) applied to 3-chloro-(E)-6-(8-methyl-8H-quino[4,3,2-kl]acridin-3-yl)-1-morpholin-4-yl-propenone, 45 (25 mg, 0.053 mmol) and methyl iodide (2 mL) gave the title compound (16 mg, 0.027 mmol, 50%).

$^1$H NMR δ (d$_6$ DMSO): 9.00 (1H, s), 8.89 (1H, s), 8.49 (1H, d, J=9.25 Hz), 8.37 (1H, s), 8.23–8.14 (3H, m), 8.00–7.92 (3H, m), 7.65 (1H, t, J=7.25 Hz), 4.37 (3H, s), 4.24 (3H, s), 3.90 (2H, br, s), 3.67 (6H, br, s); mp decomposes >200° C.; HRMS C$_{28}$H$_{25}$ClN$_3$O$_2$ calc. 470.163530 found 470.164458

Example 68

8,13-dimethyl-(E)-10-(3-morpholin-4-yl-3-oxo-propenyl)-6-methoxy-8H-quino[4,3,2-kl]acridinium iodide (68) (RHSP22)

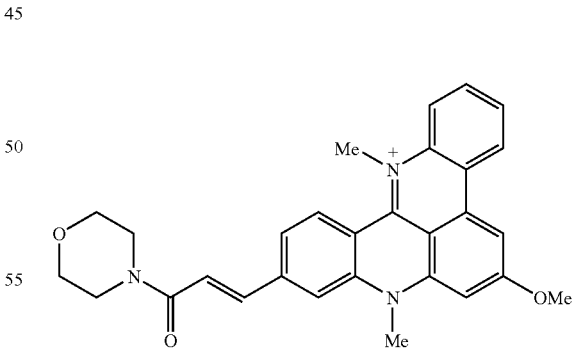

The general procedure (Method U) with work-up (C) applied to (E)-10-acryloylmorpholine-6-methoxy-8-methyl-8H-quino[4,3,2-kl]acridine, 46 (50 mg, 0.107 mol) and methyl iodide (2 mL) for 2 days gave the title compound (25 mg, 0.04 mol, 37%).

$^1$H NMR δ (d$_6$ DMSO): 8.80 (1H, d, J=7.25 Hz), 8.44 (1H, d, J=9.25 Hz), 8.37 (1H, s), 8.12–8.02 (3H, m), 7.94 (1H, t, J=8.75 Hz), 7.87–7.67 (3H, m), 7.44 (1H, s), 4.36

(3H, s), 4.20 (3H, s), 4.17 (3H, s), 3.81 (2H, br, s), 3.65 (6H, br, s); HRMS $C_{29}H_{28}N_3O_3$ calc. 466.213067 found 466.212421.

Example 69

6-(3-Acetoxy-propyl)-8,13-dimethyl-3-(3-morpholin-4-yl-3-oxo-propenyl)-8H-quino[4,3,2-kl]acridinium iodide (69) (RHSP19)

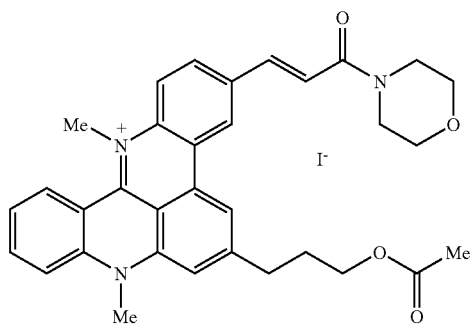

The general procedure (Method U) with work-up (A) applied to 6-(3-Acetoxy-propyl)-8,13-dimethyl-3-(3-morpholin-4-yl-3-oxo-propenyl)-8H-quino[4,3,2-kl]acridine, 47 (100 mg, 0.2 mmol) and methyl iodide (2 mL) for 3 days gave the title compound (75 mg, 0.115 mmol, 58%).

$^1$H NMR δ (CDCl$_3$): 8.68 (1H, d, J=8 Hz), 8.55 (1H, s), 8.5 (1H, s), 7.9 (3H, m), 7.6 (2H, m), 7.36 (1H, dd, J=2, 8 Hz), 7.29 (1H, d, J=15 Hz), 7.11 (1H, d, J=15 Hz), 4.54 (3H, s), 4.21 (2H, t, J=8 Hz), 4.18 (3H, s), 3.7 (8H, m), 3.28 (2H, t, J=7 Hz), 2.24 (2H, t, J=8 Hz), 2.12 (3H, s); $^{13}$C NMR δ (CDCl$_3$): 171.2, 165.1, 152.3, 151.6, 143.3, 140.2, 139.9, 138.9, 136.0, 134.0, 131.4, 131. 3,130.4, 123.5, 123.0, 122.8, 120.1, 120.0, 116.7, 116.6, 115.2, 114.7, 112.7, 63.4, 47.3, 46.0, 42.6, 36.8, 33.5, 30.36, 21.18; mp 159–161° C.; IR (KBr disc cm$^{-1}$) v 1612, 1579, 1450, 1253, 1232, 1113; HRMS $C_{33}H_{34}N_3O_4$ calc. 536.254932 found 536.257211

Example 70

3,6-Bis-(3-acetoxy-propyl)-8,13-dimethyl-8H-quino[4,3,2-kl]acridinium iodide (70) (RHSP18)

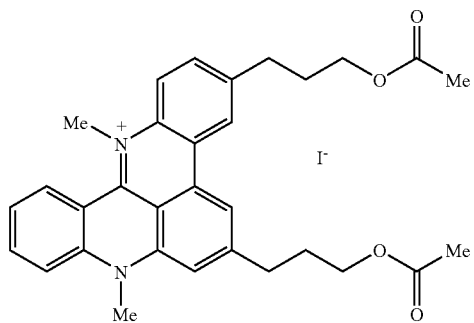

The general procedure (Method U) with work-up (C) applied to acetic acid 3-[3-(3-acetoxy-propyl)-8-methyl-8H-quino[4,3,2-kl]acridin-6-yl]-propyl ester, 51 (50 mg, 0.106 mmol) and methyl iodide (2 mL) for 2 days gave the title compound (35 mg, 0.057 mmol, 54%).

$^1$H NMR δ (CDCl$_3$): 8.54 (1H, d, J=8 Hz), 8.29 (1H, s), 8.12 (2H, m), 8.79 (2H, m), 7.72 (2H, m), 7.58 (1H, t, J=8 Hz), 4.63 (3H, s), 4.21 (7H, m), 3.17 (2H, t, J=7.5 Hz), 2.97 (2H, t, J=7.5 Hz), 2.27 (3H, t, J=7.5 Hz), 2.12 (8H, m); mp >300° C.; HRMS $C_{31}H_{33}N_2O_4$ calc. 497.244033 found 497.246197

Example 71

6,10-Bis-(3-acetoxy-propyl)-8,13-dimethyl-8H-quino[4,3,2-kl]acridinium iodide (71) (RHSP17)

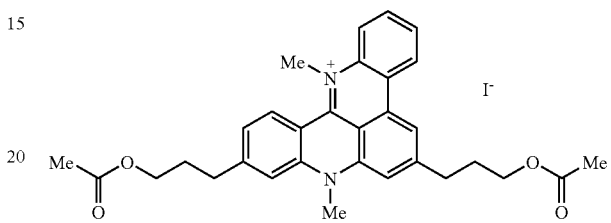

The general procedure (Method U) with work-up (B) applied to acetic acid 3-[10-(3-acetoxy-propyl)-8-methyl-8H-quino[4,3,2-kl]acridin-6-yl]-propyl ester, 52 (53 mg, 0.11 mmol) was mixed with methyl iodide (2 mL) for 2 days gave the title compound (28 mg, 0.046 mmol, 42%).

$^1$H NMR δ (CD$_2$Cl$_2$): 8.42 (2H, d, J=8.5 Hz), 8.04 (1H, s), 7.96 (1H, d, J=8.5 Hz), 7.65 (4H, m), 7.46 (1H,c d, J=8 Hz), 4.44 (3H, s), 4.12 (7H, m), 3.09 (2H, t, J=8 Hz), 2.96 (2H, t, J=8 Hz), 2.08 (4H, m), 2.04 (6H, m); $^{13}$C NMR δ (CDCl$_3$): 171.0, 151.6, 151.4, 151.3, 143.5, 140.3, 138.6, 132.3, 130.8,127.6, 124.7, 123.9, 122.3, 119.3, 116.0, 114.9, 114.7, 113.0, 112.8, 63.2, 47.0, 37.5, 32.9, 30.2, 29.5, 21.0, 20.97; mp >300° C.; HRMS $C_{31}H_{33}N_2O_4$ calc. 497.244033 found 497.242223.

Biological Data

Tag Polymerase Assay

Compounds were tested using a Taq assay to eliminate broad-spectrum polymerase inhibitors and thus filter out any false positives which might have occurred in the TRAP assay. Thus, preferred compounds are "Taq-negative." Compounds were tested as their acid addition salts at 10, 20 and 50 μM final concentrations in a PCR 50 μL master mix containing 10 ng pCI-neo mammalian expression vector (Promega, Southampton, UK) and forward (GGAGTTC-CGCGTTACATAAC) and reverse (GTCTGCTCGAAG-CATTAACC) primers (200 nmol) as described in the art (see, e.g., Perry et al., 1998a). The product of approximately 1 kb was visualized on a 2% w/w agarose gel following amplification (30 cycles of 941 C. for 1 min, 551 C. for 1 min and 721 C. for 2.5 min). All compounds were found to be Taq negative.

Modified Telomeric Repeat Amplification Protocol (TRAP) Assay

The ability of compounds to inhibit telomerase in a cell-free assay was assessed with a modified TRAP assay using extracts from exponentially growing A2780 human ovarian carcinoma cells. The TRAP assay was performed in 2 steps: (a) telomerase-mediated extension of the forward primer (TS: 5'-AATCCGTCGAGCAGAGTT, Oswel Ltd., Southampton, UK) contained in a 40 μL reaction mix comprising TRAP buffer (20 mM Tris-HCl (pH 8.3), 68 mM KCl, 1.5 mM $MgCl_2$, 1 mM EGTA, 0.05% v/v Tween 20), 0.05 μg bovine serum albumin, 50 μM of each deoxynucleotide triphosphate, 0.1 μg TS primer, and 3 μCi of [α-$^{32}$P] dCTP (Amersham plc, UK). Protein (0.04 μg) was then incubated with the reaction mix±agent (acid addition and quaternary dimethiodide salts) at final concentrations of up to 50 μM for 20 min at 251 C. A lysis buffer (no protein) control, heat-inactivated protein control, and 50% protein (0.02 μg) control were included in each assay; and (b) while heating at 801 C. in a PCR block of a thermal cycler (Hybaid, UK) for 5 min to inactivate telomerase activity, 0.1 μg of reverse CX primer (3'-AATCCCATTCCCATTC-CCATTCCC-5') and 2 Units of Taq DNA polymerase ("red hot", Advanced Biotechnologies) were added. A 3-step PCR was then performed: 94° C. for 30 s, 50° C. for 30 s, and 721 C. for 1 min for 31 cycles. Telomerase-extended PCR products in the presence or absence of compounds were then determined either by electrophoretic separation using 8% w/w acrylamide denaturing gels and analysis by phosphorimaging or autoradiography, or by harvesting on Whatman filters (25 mm glass microfibre) and analysis by liquid scintillation counting. The data are summarized in Table 1.

Growth Inhibition Assay

Growth inhibition was measured in the following cells lines using the sulforhodamine B (SRB) assay:

A2780: human ovarian carcinoma cell line.
CH1: human ovarian carcinoma cell line.
SKOV-3: human ovarian carcinoma cell line.
A431: human vulval carcinoma cells (short telomeres).
GM847: carcinoma cell line immortalised by ALT pathway.

Briefly, between 3000 and 6000 cells were seeded into the wells of 96-well microtiter plates and allowed to attach overnight. Test compounds (salts) were dissolved at 500 μM in water and immediately added to wells in quadruplicate at final concentrations of 0.05, 0.25, 1, 5 and 25 μM. Following an incubation period of 96 hr, remaining cells were fixed with ice-cold 10% w/v trichloroacetic acid (30 min) and stained with 0.4% SRB in 1% v/v acetic acid (15 min). Mean absorbance at 540 nm for each drug concentration was expressed as a percentage of the control untreated well absorbance, and $IC_{50}$ values (concentration required to inhibit cell growth by 50%) were determined for each agent. The data are summarized in Table 1.

TABLE 1

Telomerase Inhibitory Activity and Cytotoxicity

| | | | Cytotoxicity $IC_{50}$ (μM) | | | | |
|---|---|---|---|---|---|---|---|
| | Compound | $^{tel}IC_{50}$ (μM) | A2780 | CH1 | SKOV-3 | A431 | GM847 |
| 1 | 9 | RHPS01 | 0.74 | 0.9 | 0.37 | 3.6 | — | — |
| 2 | 10 | RHPS02 | 0.24 | 1.3 | 1.4 | 9.3 | — | — |
| 3 | 11 | RHPS03 | 0.18 | 0.33 | 0.29 | 0.75 | — | — |
| 4 | 12 | RHPS04 | 0.31 | 1.1 | 0.50 | 23.0 | — | — |
| 5 | 55 | RHPS05 | 1.55 | 1.6 | 1.1 | 18.0 | — | — |
| 6 | 56 | RHPS06 | 0.26 | 1.1 | 0.5 | 12.5 | — | — |
| 7 | 58 | RHPS07 | 0.94 | 14.5 | 3.8 | >25 | — | — |
| 8 | 59 | RHPS08 | 0.47 | 0.62 | 0.13 | 3.6 | — | — |
| 9 | 65 | RHPS09 | 3.02 | >25 | 11.5 | >25 | — | — |
| 10 | 60 | RHPS10 | 0.24 | — | 1.1 | 6.3 | 3.2 | 0.8 |
| 11 | 63 | RHPS11 | 1.70 | — | 1.6 | 3.5 | 1.7 | 17.7 |
| 12 | 61 | RHPS12 | 0.28 | — | 0.3 | 10.0 | 1.0 | 0.4 |
| 13 | 62 | RHPS13 | 0.57 | — | 0.2 | 1.5 | 0.4 | 0.5 |
| 14 | 64 | RHPS15 | 0.19 | — | 2.2 | 19.0 | 3.2 | 4.5 |
| 15 | 66 | RHPS16 | 0.37 | — | 17.8 | >25.0 | 12.5 | >25.0 |

REFERENCES

A number of patents and publications are cited above in order to more fully describe and disclose the invention and the state of the art to which the invention pertains. Full citations for these references are provided below. Each of these references is incorporated herein by reference in its entirety into the present disclosure.

Albert, A., 1966, *The Acridines,* 2nd Edition, Edward Arnold (Publishers) Ltd., London.

Autexier, 1999, "Telomerase as a Possible Target for Anticancer Therapy," *Chemistry & Biology,* November 1999, Vol. 6, pp. R299–R303.

Bostock-Smith, C. E., et al., 1999 (Part 6), *Biochemistry,* Vol. 38, No. 1, pp. 6723–6731.

Coulson, D. R., 1990, *Inorg. Synth.,* p. 28.

Gimenez-Arnau et al., 1998, "Antitumour Polycyclic Acridines, Part 4," *Anti-Cancer Drug Design,* Vol. 13, pp. 431–451.

Gimenez-Arnau et al., 1998, "Antitumour Polycyclic Acridines, Part 2," *Anti-Cancer Drug Design,* Vol. 13, pp. 125–143.

Gullier, F.; Nivoliers, F.; Godard, A.; Marsais, F.; Queguiner, G.; Siddiqui, M. A.; Sneikus, V., 1995, *J. Org. Chem.,* Vol. 60, p. 292

Hagan, D. J., et al., 1997 (Part 1), *J. Chem. Soc., Perkin Trans. I,* pp. 2739–2746.

Hagan, D. J., et al., 1998 (Part 3), *J. Chem. Soc., Perkin Trans. I,* pp. 915–923.

Hodgeman, D. K. C.; Prager, R. H., 1972, *Aus. J. Chem.,* Vol. 25, p. 194

Jaroszewska-Manaj, J., et al., 2000, *Magn. Reson. Chem.,* Vol. 38, No. 6, pp. 482–485.

Julino, M., et al., 1998 (Part 5), *J. Chem. Soc., Perkin Trans. I,* pp. 1677–1684.

Katritzky, A. R., et al., 1999, *J. Heterocyclic Chem.,* Vol. 36, pp. 927–932.

Littke, A. F., et al., 1999, *J. Org. Chem.,* Vol. 64, pp. 10–11.

Missailidis, S., et al., 1997, *Spectrosc. Biol. Mol.: Mod. Trends,* (Euro. Conf.), 7th, Eds. Carmona, P., et al., pp. 391–392.

Mitchell, G., et al., 1987, *J. Chem. Soc., Perkin Trans. 1,* Vol. 2, pp. 403–412.

Neidle et al., 1999, "Telomerase as an Anti-Cancer Target: Current Status and Future Prospects," *Anti-Cancer Drug Design,* Vol. 14, pp. 341–347.

Oszczapowicz, J.; Jaroszewska-Manaj, J.; Ciszak, E.; Gdaniec, M., 1988, *Tetrahedron,* Vol. 44, No. 21, pp. 6645–6650.

Perry et al., 1998a, "1,4- and 2,6-Disubstituted Amidoanthracene-9,10-dione Derivatives as Inhibitors of Human Telomerase," *J. Med. Chem.,* Vol. 41, pp. 3253–3260.

Perry et al., 1998b, "Telomeres and Telomerase: Targets for Cancer Chemotherapy?," *Exp. Opin. Ther. Patents,* Vol. 8, No. 12, pp. 1567–1586.

Prager, R. H., et al., 1972, *Aus. J. Chem.,* Vol. 25, p. 194.

Reisch, J.; Herath, M. T. B.; Kumar, N. S., 1991, *Liebigs Ann. Chem.,* pp. 695–689.

Sharma et al., 1997, "Preclinical and Clinical Strategies for Development of Telomerase and Telomere Inhibitors," *Annals of Oncology,* Vol. 8, pp. 1063–1074.

Song, Z; Mertzmann, M.; Hughes, D. L., 1993, "Substituted quinolines were prepared by a modified Scraup synthesis," *J. Heterocyclic Chem.,* Vol. 30, p. 17.

Stanslas, J., et al., 2000, *J. Med. Chem.,* Vol. 43, pp. 1563–1572.

Timari, G.; Soos, T.; Hajos, G.; Messmer, A.; Nacsa, J.; Molnar, J., 1996, *Bioorg. Med. Chem. Lett.*, Vol. 6, No. 23, p. 2831–2836.

Urquidi et al., 1998, "Telomerase in Cancer: Clinical Applications," *Ann. Med.*, Vol. 30, pp. 419–430.

Wolfe, J. P., et al., 2000, *J. Org. Chem.*, Vol. 65, p. 1158.

What the invention claimed is:

1. A compound selected from compounds of the following formula, and pharmaceutically acceptable salts and solvates thereof:

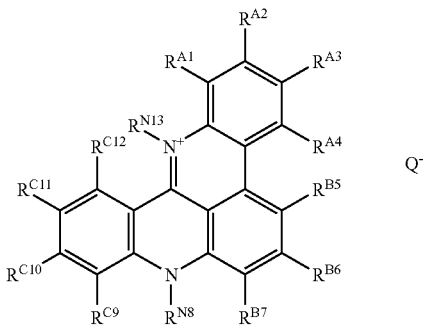

wherein:
each one of $R^{A1}$, $R^{A2}$, $R^{A3}$, and $R^{A4}$ is independently —H or a ring substituent;
each one of $R^{B5}$, $R^{B6}$, and $R^{B7}$ is independently —H or a ring substituent;
each one of $R^{C9}$, $R^{C10}$, $R^{C11}$, and $R^{C12}$ is independently —H or a ring substituent;
$R^{N8}$ is independently a nitrogen substituent;
$R^{N13}$ is independently a nitrogen substituent; and,
Q is independently an anion;
wherein:
said ring substituents are independently selected from:
halo;
hydroxy;
ether;
formyl;
acyl;
carboxy;
ester;
acyloxy;
oxycarbonyloxy;
amido;
acylamido;
tetrazolyl;
amino;
nitro;
cyano;
azido;
sulfhydryl;
thioether;
sulfonamido;
unsubstituted $C_{1-7}$alkyl;
$C_{1-7}$haloalkyl;
$C_{1-7}$hydroxyalkyl;
$C_{1-7}$carboxyalkyl;
$C_{1-7}$acyloxyalkyl;
$C_{1-7}$oxycarbonylalkyl;
$C_{1-7}$oxycarbonyloxyalkyl;
$C_{1-7}$aminoalkyl;
$C_{1-7}$amidoalkyl;
$C_{1-7}$acylamidoalkyl;
$C_{1-7}$cyanoalkyl; and
$C_{5-20}$aryl-$C_{1-7}$alkyl; and
said nitrogen substituents are independently selected from:
unsubstituted $C_{1-7}$alkyl;
$C_{1-7}$haloalkyl;
$C_{1-7}$hydroxyalkyl;
$C_{1-7}$alkoxyalkyl;
$C_{1-7}$carboxyalkyl;
$C_{1-7}$aminoalkyl;
$C_{5-20}$aryl-$C_{1-7}$alkyl;
$C_{3-20}$heterocyclyl;
$C_{5-20}$aryl;
$C_{1-7}$alkyl-$C_{5-20}$aryl; and
$C_{5-20}$haloaryl;
and wherein:
each alkyl group is aliphatic, and is saturated or partially unsaturated; and
each aryl group is a carboaryl group or a heteroaryl group;
with the proviso that the compound is not:
8,13-diethyl-6-methyl-8H-quino[4,3,2-kl]acridinium iodide; or,
8,13-diethyl-3,6,11-trimethyl-8H-quino[4,3,2-kl]acridinium iodide.

2. A compound according to claim 1, wherein:
$R^{A1}$ and $R^{A4}$ are both —H;
$R^{B5}$ and $R^{B7}$ are both —H;
$R^{C9}$ and $R^{C12}$ are both —H;
and wherein the compound is selected from compounds of the following formula and pharmaceutically acceptable salts and solvates thereof:

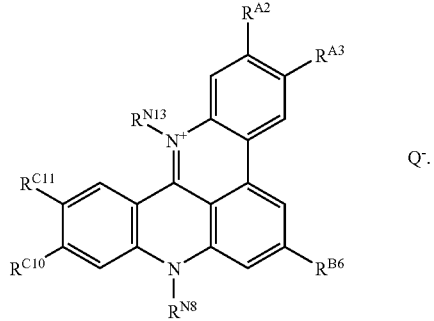

3. A compound according to claim 2, wherein:
$R^{A1}$, $R^{A2}$, $R^{A3}$, and $R^{A4}$ are all —H;
$R^{B5}$, $R^{B6}$, and $R^{B7}$ are all —H; and,
$R^{C9}$, $R^{C10}$, $R^{C11}$, and $R^{C12}$ are all —H;
(8,13-disubstituted); or
$R^{A1}$, $R^{A2}$, and $R^{A4}$ are all —H;
$R^{B5}$, $R^{B6}$, and $R^{B7}$ are all —H;
$R^{C9}$, $R^{C10}$, $R^{C11}$, and $R^{C12}$ are all —H; and,
$R^{A3}$ is not —H;
(3,8,13-trisubstituted); or
$R^{A1}$, $R^{A2}$, $R^{A3}$, and $R^{A4}$ are all —H;
$R^{B5}$ and $R^{B7}$ are both —H;
$R^{C9}$, $R^{C10}$, $R^{C11}$, and $R^{C12}$ are all —H; and,
$R^{B6}$ is not —H;
(6,8,13-trisubstituted); or
$R^{A1}$, $R^{A2}$, $R^{A3}$, and $R^{A4}$ are all —H;
$R^{B5}$, $R^{B6}$, and $R^{B7}$ are all —H;
$R^{C9}$, $R^{C11}$, and $R^{C12}$ are all —H; and,
$RC^{10}$ is not —H;

(8,10,13-trisubstituted); or
$R^{A1}$, $R^{A2}$, and $R^{A4}$ are all —H;
$R^{B5}$ and $R^{B7}$ are both —H;
$R^{C9}$, $R^{C10}$, $R^{C11}$, and $R^{C12}$ are all —H; and,
$R^{A3}$ and $R^{B6}$ are both not —H;
(3,6,8,13-tetrasubstituted); or
$R^{A1}$, $R^{A2}$ and $R^{A4}$ are all —H;
$R^{B5}$, $R^{B6}$, and $R^{B7}$ are all —H;
$R^{C9}$, $R^{C11}$, and $R^{C12}$ are all —H; and,
$R^{A3}$ and $R^{C10}$ are both not —H;
(3,8,10,13-tetrasubstituted); or
$R^{A1}$, $R^{A2}$, $R^{A3}$, and $R^{A4}$ are all —H;
$R^{B5}$ and $R^{B7}$ are both —H;
$R^{C9}$, $R^{C11}$, and $R^{C12}$ are all —H; and,
$R^{B6}$ and $R^{C10}$ are both not —H;
(6,8,10,13-tetrasubstituted); or
$R^{A1}$, $R^{A2}$, and $R^{A4}$ are all —H;
$R^{B5}$ and $R^{B7}$ are both —H;
$R^{C9}$, $R^{C11}$, and $R^{C12}$ are all —H; and,
$R^{A3}$, $R^{B6}$, and $R^{C10}$ are all not —H;
(3,6,8,10,13-pentasubstituted); or
$R^{A1}$, $R^{A2}$, and $R^{A4}$ are all —H;
$R^{B5}$ and $R^{B7}$ are both —H;
$R^{C9}$, $R^{C10}$, and $R^{C12}$ are all —H; and,
$R^{A3}$, $R^{B6}$, and $R^{C11}$ are all not —H;
(3,6,8,11,13-pentasubstituted).

4. A compound according to claim 1, wherein each of said nitrogen substituents, $R^{N8}$ and $R^{N13}$, is independently selected from:
 unsubstituted $C_{1-4}$alkyl;
 $C_{1-4}$haloalkyl;
 $C_{1-4}$hydroxyalkyl;
 $C_{1-4}$alkoxyalkyl;
 $C_{1-4}$carboxyalkyl; and
 $C_{1-4}$aminoalkyl.

5. A compound according to claim 2, wherein each of said nitrogen substituents, $R^{N8}$ and $R^{N13}$, is independently selected from:
 unsubstituted $C_{1-4}$alkyl;
 $C_{1-4}$haloalkyl;
 $C_{1-4}$hydroxyalkyl;
 $C_{1-4}$alkoxyalkyl;
 $C_{1-4}$carboxyalkyl; and
 $C_{1-4}$aminoalkyl.

6. A compound according to claim 5, wherein said nitrogen substituents, $R^{N8}$ and $R^{N13}$, are not both -Et.

7. A compound according to claim 1, wherein each of said nitrogen substituents, $R^{N8}$ and $R^{N13}$, is independently selected from:
 unsubstituted $C_1$alkyl;
 $C_1$haloalkyl;
 $C_1$hydroxyalkyl;
 $C_1$alkoxyalkyl;
 $C_1$carboxyalkyl; and
 $C_1$aminoalkyl.

8. A compound according claim 1, wherein each of said nitrogen substituents, $R^{N8}$ and $R^{N13}$, is independently: -Me, —$CF_3$, —$CHF_2$, —$CH_2F$, —$CH_2OH$, or —$CH_2NH_2$.

9. A compound according to claim 2, wherein each of said nitrogen substituents, $R^{N8}$ and $R^{N13}$, is independently -Me, —$CF_3$, —$CHF_2$, —$CH_2F$, —$CH_2OH$, or —$CH_2NH_2$.

10. A compound according to claim 1, wherein said nitrogen substituents, $R^{N8}$ and $R^{N13}$, are both -Me.

11. A compound according to claim 2, wherein said nitrogen substituents, $R^{N8}$ and $R^{N13}$, are both -Me.

12. A compound according to claim 1, wherein each of said ring substituents is independently selected from:
 halo;
 $C_{1-7}$alkoxy;
 ester;
 acyloxy;
 oxycarbonyloxy;
 amido;
 acylamido;
 amino;
 nitro;
 cyano;
 azido;
 unsubstituted $C_{1-7}$alkyl;
 $C_{1-7}$haloalkyl;
 $C_{1-7}$hydroxyalkyl;
 $C_{1-7}$carboxyalkyl;
 $C_{1-7}$acyloxyalkyl;
 $C_{1-7}$oxycarbonylalkyl;
 $C_{1-7}$oxycarbonyloxyalkyl;
 $C_{1-7}$aminoalkyl;
 $C_{1-7}$amidoalkyl;
 $C_{1-7}$acylamidoalkyl;
 $C_{1-7}$cyanoalkyl; and
 $C_{5-20}$aryl-$C_{1-7}$alkyl.

13. A compound according to claim 1, wherein each of said ring substituents is independently selected from:
 halo;
 $C_{1-7}$alkoxy;
 ester;
 acyloxy;
 oxycarbonyloxy;
 cyano;
 unsubstituted $C_{1-7}$alkyl;
 $C_{1-7}$haloalkyl;
 $C_{1-7}$hydroxyalkyl;
 $C_{1-7}$carboxyalkyl;
 $C_{1-7}$acyloxyalkyl;
 $C_{1-7}$oxycarbonylalkyl;
 $C_{1-7}$oxycarbonyloxyalkyl;
 $C_{1-7}$aminoalkyl;
 $C_{1-7}$amidoalkyl;
 $C_{1-7}$acylamidoalkyl;
 $C_{1-7}$cyanoalkyl; and
 $C_{5-20}$aryl-$C_{1-7}$alkyl.

14. A compound according to claim 4, wherein each of said ring substituents is independently selected from:
 halo;
 $C_{1-7}$alkoxy;
 ester;
 acyloxy;
 oxycarbonyloxy;
 amido;
 acylamido;
 amino;
 nitro;
 cyano;
 azido;
 unsubstituted $C_{1-7}$alkyl;
 $C_{1-7}$haloalkyl;
 $C_{1-7}$hydroxyalkyl;
 $C_{1-7}$carboxyalkyl;
 $C_{1-7}$acyloxyalkyl;
 $C_{1-7}$oxycarbonylalkyl;
 $C_{1-7}$oxycarbonyloxyalkyl;
 $C_{1-7}$aminoalkyl;
 $C_{1-7}$amidoalkyl;
 $C_{1-7}$acylamidoalkyl;
 $C_{1-7}$cyanoalkyl; and $C_{5-20}$aryl-$C_{1-7}$alkyl.

15. A compound according to claim 4, wherein each of said ring substituents is independently selected from:
    halo;
    $C_{1-7}$alkoxy;
    ester;
    acyloxy;
    oxycarbonyloxy;
    cyano;
    unsubstituted $C_{1-7}$alkyl;
    $C_{1-7}$haloalkyl;
    $C_{1-7}$hydroxyalkyl;
    $C_{1-7}$carboxyalkyl;
    $C_{1-7}$acyloxyalkyl;
    $C_{1-7}$oxycarbonylalkyl;
    $C_{1-7}$oxycarbonyloxyalkyl;
    $C_{1-7}$aminoalkyl;
    $C_{1-7}$amidoalkyl;
    $C_{1-7}$acylamidoalkyl;
    $C_{1-7}$cyanoalkyl; and
    $C_{5-20}$aryl-$C_{1-7}$alkyl.

16. A compound according to claim 1, wherein each of said ring substituents is independently selected from:
    —F, —Cl, —Br, —I;
    —OMe, —OEt, —O(nPr), —O(iPr), —O(nBu), —O(tBu), —OCH$_2$Ph; —OCF$_3$, —OCHF$_2$, —OCH$_2$F, —OCCl$_3$, —OCBr$_3$, —OCH$_2$CH$_2$F, —OCH$_2$CHF$_2$, —CH$_2$CF$_3$;
    —C(=O)Me, —C(=O)Et, —C(=O)(nPr), —C(=O)(iPr), —C(=O)(nBu), —C(=O)(tBu), —C(=O)Ph;
    —C(=O)OMe, —C(=O)OEt, —C(=O)O(nPr), —C(=O)O(iPr), —C(=O)O(nBu), —C(=O)O(tBu);
    —OC(=O)Me, —OC(=O)Et, —OC(=O)(nPr), —OC(=O)(iPr), —OC(=O)(nBu), —OC(=O)(tBu);
    —OC(=O)OMe, —OC(=O)OEt, —OC(=O)O(nPr), —OC(=O)O(iPr), —OC(=O)O(nBu), —OC(=O)O(tBu);
    —C(=O)NH$_2$, —C(=O)NHMe, —C(=O)NHEt, —C(=O)NH(nPr), —C(=O)NH(iPr), —C(=O)NH(nBu), —C(=O)NH(tBu), —C(=O)NMe$_2$, —C(=O)NEt$_2$, —C(=O)N(nPr)$_2$, —C(=O)N(iPr)$_2$, —C(=O)N(nBu)$_2$, —C(=O)N(tBu)$_2$;
    —NHC(=O)Me, —NHC(=O)Et, —NHC(=O)(nPr), —NHC(=O)(iPr), —NHC(=O)(nBu), —NHC(=O)(tBu), —NHC(=O)Ph, succinimidyl, maleimidyl;
    —NH$_2$, —NHMe, —NHEt, —NH(nPr), —NH(iPr), —NH(nBu), —NH(tBu), —NMe$_2$, —NEt$_2$, —N(nPr)$_2$, —N(iPr)$_2$, —N(nBu)$_2$, —N(tBu)$_2$;
    —NH(CH$_2$)$_2$NH$_2$, —NH(CH$_2$)$_3$NH$_2$, —NH(CH$_2$)$_4$NH$_2$, —NH(CH$_2$)$_5$NH$_2$, —NH(CH$_2$)$_6$NH$_2$, —NHCH$_2$NH(Me), —NH(CH$_2$)$_2$NH(Me), —NH(CH$_2$)$_3$NH(Me), —NH(CH$_2$)$_4$NH(Me), —NH(CH$_2$)$_5$NH(Me), —NH(CH$_2$)$_6$NH(Me), —NHCH$_2$NH(Et), —NH(CH$_2$)$_2$NH(Et), —NH(CH$_2$)$_3$NH(Et), —NH(CH$_2$)$_4$NH(Et), —NH(CH$_2$)$_5$NH(Et), —NH(CH$_2$)$_6$NH(Et);
    —NO$_2$;
    —CN;
    —N$_3$;
    -Me, -Et, -nPr, -iPr, -nBu, -tBu;
    —OF$_3$, —CHF$_2$, —CH$_2$F, —CCl$_3$, —CBr$_3$, —CH$_2$CH$_2$F, —CH$_2$CHF$_2$, —CH$_2$CF$_3$;
    —CH$_2$OH, —CH$_2$CH$_2$OH, —CH(OH)CH$_2$OH;
    —CH$_2$COOH, —CH$_2$CH$_2$COOH, —CH$_2$CH$_2$CH$_2$COOH;
    —CH$_2$OC(=O)Me, —CH$_2$CH$_2$OC(=O)Me, —CH=CHOC(=O)Me;
    —CH$_2$C(=O)OMe, —CH$_2$CH$_2$C(=O)OMe, —CH=CHC(=O)OMe;
    —CH$_2$OC(=O)OMe, —CH$_2$CH$_2$OC(=O)OMe, —CH=CHOC(=O)OMe;
    —CH$_2$NH$_2$, —CH$_2$CH$_2$NH$_2$, —CH=CHNH$_2$, —CH$_2$CH$_2$NMe$_2$;
    —CH$_2$NHC(=O)Me, —CH$_2$CH$_2$NHC(=O)Me, —CH=CHNHC(=O)Me;
    —CH$_2$C(=O)NH$_2$, —CH$_2$CH$_2$C(=O)NH$_2$, —CH=CHC(=O)NH$_2$;
    —CH$_2$CN, —CH$_2$CH$_2$CN, and —CH=CHCN.

17. A compound according to claim 1, wherein each of said ring substituents is independently selected from:
    —F, —Cl, -Me, —OMe, —CN,
    —C(=O)OMe, —OC(=O)Me, —OC(=O)OMe,
    —CH$_2$CH$_2$C(=O)OMe,
    —CH$_2$CH$_2$OC(=O)Me,
    —CH=CHC(=O)OMe,
    —CH=CHOC(=O)Me,
    —CH=CHC(=O)NH$_2$,
    —CH=CHC(=O)(morpholin-4-yl),
    —CH=CHCH$_2$NHC(=O)CF$_3$,
    —CH=CHCN, and
    —C≡CCH$_2$NHC(=O)CF$_3$.

18. A compound according to claim 1, wherein each of said ring substituents is independently: —F, —Cl, -Me, —OMe, —C(=O)OMe, —OC(=O)Me, or —OC(=O)OMe.

19. A compound according to claim 5, wherein each of said ring substituents is independently: —F, —Cl, -Me, —OMe, —C(=O)OMe, —OC(=O)Me, or —OC(=O)OMe.

20. A compound according to claim 6, wherein each of said ring substituents is independently: —F, —Cl, -Me, —OMe, —C(=O)OMe, —OC(=O)Me, or —OC(=O)OMe.

21. A compound according to claim 11, wherein each of said ring substituents is independently: —F, —Cl, -Me, —OMe, —C(=O)OMe, —OC(=O)Me, or —OC(=O)OMe.

22. A compound according claim 1, wherein the anion is independently derived from one or more of: the following inorganic acids: hydrochloric, hydrobromic, hydroiodic, sulfuric, sulfurous, nitric, nitrous, phosphoric, and phosphorous; the following organic acids: acetic, propionic, succinic, gycolic, stearic, lactic, malic, tartaric, citric, ascorbic, maleic, hydroxymaleic, phenylacetic, glutamic, benzoic, salicylic, sulfanilic, 2-acetyoxybenzoic, fumaric, toluenesulfonic, methanesulfonic, ethanesulfonic, ethane disulfonic, oxalic, isethionic, gluconic, and valeric; and the following polymeric acids: tannic acid and carboxymethyl cellulose.

23. A compound according to claim 2, wherein the anion is independently derived from one or more of: the following inorganic acids: hydrochloric, hydrobromic, and hydroiodic; and the following organic acids: methanesulfonic, ethanesulfonic, isethionic, fumaric, and gluconic.

24. A compound according to claim 2, wherein the anion is independently: chloride, bromide, iodide, methylsulfate, ethylsulfate, isethionate, fumarate, or gluconate.

25. A compound according to claim 5, wherein the anion is independently: chloride, bromide, iodide, methylsulfate, ethylsulfate, isethionate, fumarate, or gluconate.

26. A compound according to claim 20, wherein the anion is independently: chloride, bromide, iodide, methylsulfate, ethylsulfate, isethionate, fumarate, or gluconate.

27. A compound according to claim 20, wherein the anion is independently iodide or methylsulfate.
28. A compound according to claim 1, wherein the compound is selected from the following compounds, and pharmaceutically acceptable salts and solvates thereof:
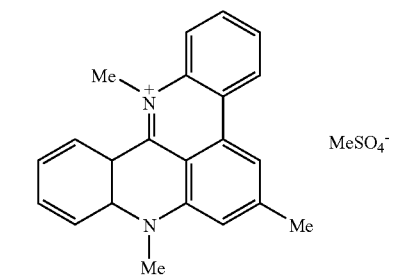
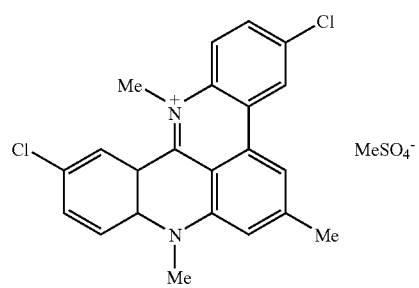
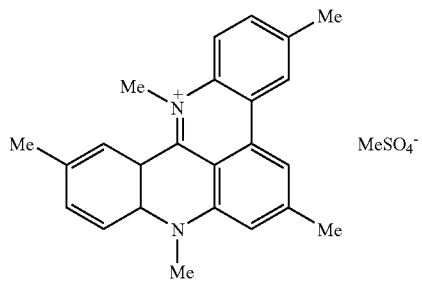
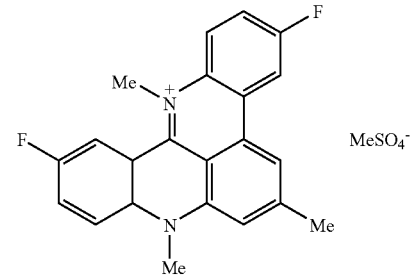
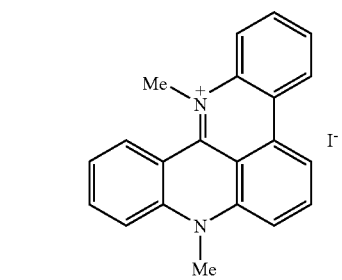
-continued
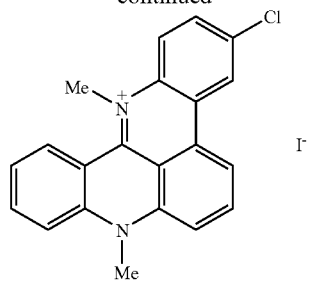
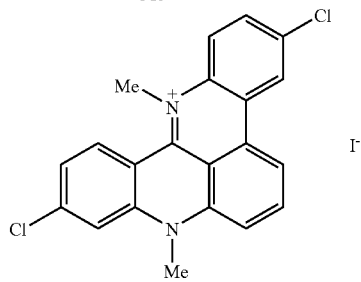
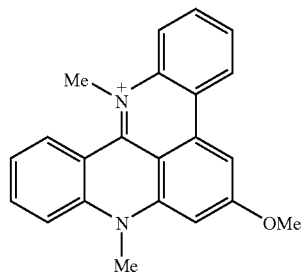
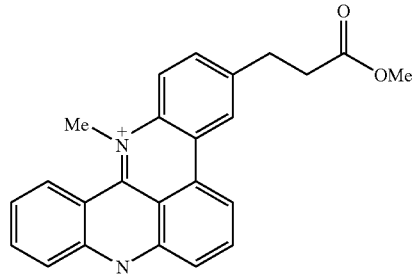
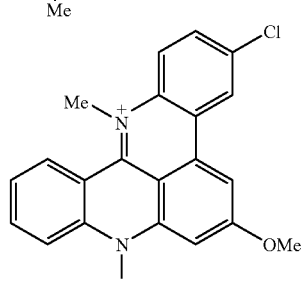
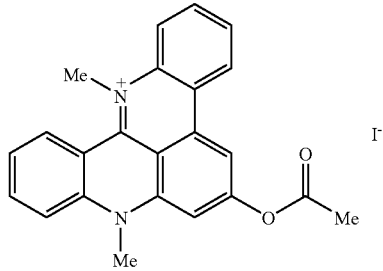

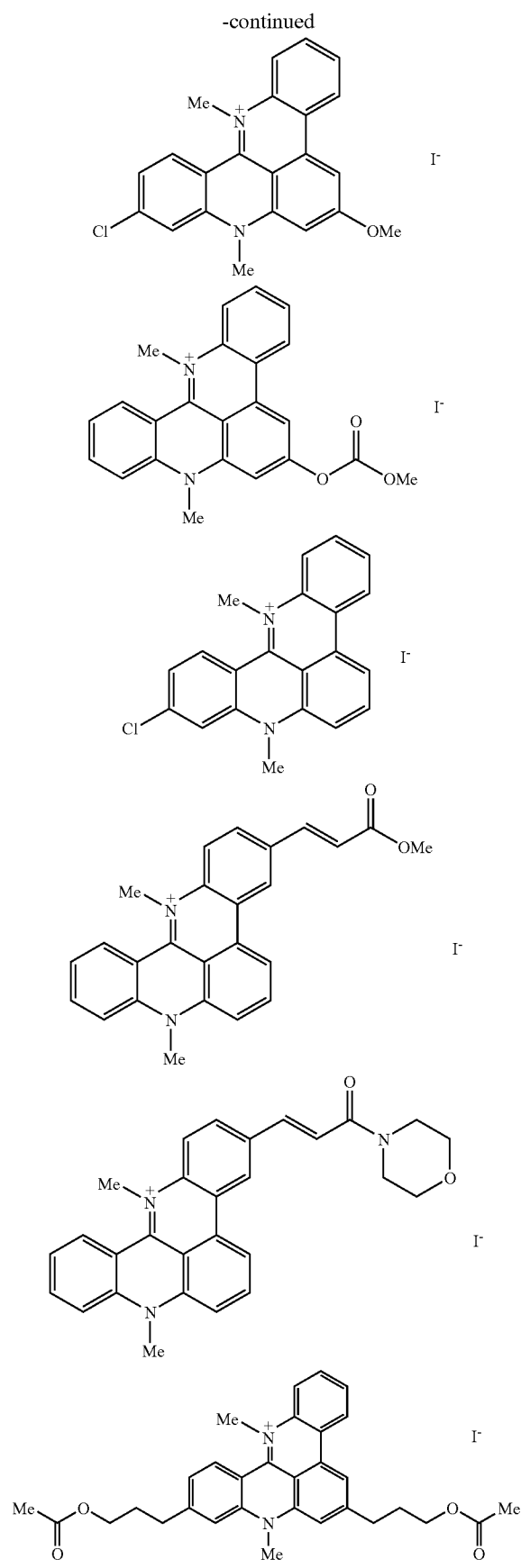
29. A composition comprising a compound according to claim 1 and a pharmaceutically acceptable carrier or diluent.
30. A method of inhibiting telomerase in vitro or in vivo, comprising contacting a cell with an effective amount of compound selected from compounds of the following formula, and pharmaceutically acceptable salts and solvates thereof:

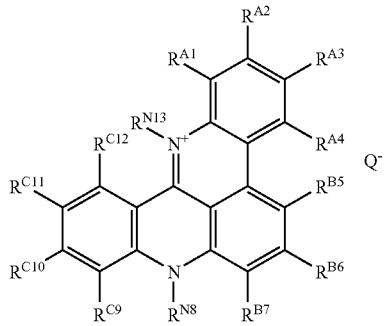

wherein:
each one of $R^{A1}$, $R^{A2}$, $R^{A3}$, and $R^{A4}$ is independently —H or a ring substituent;
each one of $R^{B5}$, $R^{B6}$, and $R^{B7}$ is independently —H or a ring substituent;
each one of $R^{C9}$, $R^{C10}$, $R^{C11}$, and $R^{C12}$ is independently —H or a ring substituent;
$R^{N8}$ is independently a nitrogen substituent;
$R^{N13}$ is independently a nitrogen substituent; and,
Q is independently an anion;
wherein:
said ring substituents are independently selected from:
halo;
hydroxy;
ether;
formyl;
acyl;
carboxy;
ester;
acyloxy;
oxycarbonyloxy;
amido;
acylamido;
tetrazolyl;
amino;
nitro;
cyano;
azido;
sulfhydryl;
thioether;
sulfonamido;
unsubstituted $C_{1-7}$alkyl;
$C_{1-7}$haloalkyl;
$C_{1-7}$hydroxyalkyl;
$C_{1-7}$carboxyalkyl;
$C_{1-7}$acyloxyalkyl;
$C_{1-7}$oxycarbonylalkyl;
$C_{1-7}$oxycarbonyloxyalkyl;
$C_{1-7}$aminoalkyl;
$C_{1-7}$amidoalkyl;
$C_{1-7}$acylamidoalkyl;
$C_{1-7}$cyanoalkyl; and
$C_{5-20}$aryl-$C_{1-7}$alkyl; and,
said nitrogen substituents are independently selected from:
unsubstituted $C_{1-7}$alkyl;
$C_{1-7}$haloalkyl;
$C_{1-7}$hydroxyalkyl;
$C_{1-7}$alkoxyalkyl;
$C_{1-7}$carboxyalkyl;
$C_{1-7}$aminoalkyl;
$C_{5-20}$aryl-$C_{1-7}$alkyl;
$C_{3-20}$heterocyclyl;
$C_{5-20}$aryl;
$C_{1-7}$alkyl-$C_{5-20}$aryl; and
$C_{5-20}$haloaryl;
and wherein:
each alkyl group is aliphatic, and is saturated or partially unsaturated; and
each aryl group is a carboaryl group or a heteroaryl group.

31. A method according to claim 30, wherein
$R^{A1}$ and $R^{A4}$ are both —H;
$R^{B5}$ and $R^{B7}$ are both —H;
$R^{C9}$ and $R^{C12}$ are both —H;
and wherein the compound is selected from compounds of the following formula and pharmaceutically acceptable salts and solvates thereof:

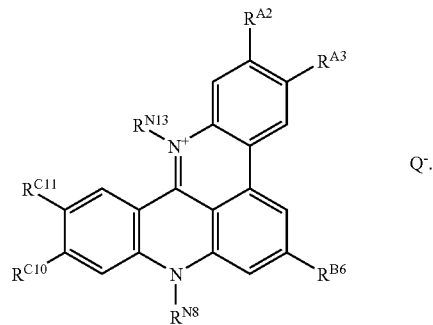

32. A method according to claim 31, wherein:
$R^{A1}$, $R^{A2}$, $R^{A3}$, and $R^{A4}$ are all —H;
$R^{B5}$, $R^{B6}$, and $R^{B7}$ are all —H; and,
$R^{C9}$, $R^{C10}$, $R^{C11}$, and $R^{C12}$ are all —H;
(8,13-disubstituted); or
$R^{A1}$, $R^{A2}$, and $R^{A4}$ are all —H;
$R^{B5}$, $R^{B6}$, and $R^{B7}$ are all —H;
$R^{C9}$, $R^{C10}$, $R^{C11}$, and $R^{C12}$ are all —H; and,
$R^{A3}$ is not —H;
(3,8,13-trisubstituted); or
$R^{A1}$, $R^{A2}$, $R^{A3}$, and $R^{A4}$ are all —H;
$R^{B5}$ and $R^{B7}$ are both —H;
$R^{C9}$, $R^{C10}$, $R^{C11}$, and $R^{C12}$ are all —H; and,
$R^{B6}$ is not —H;
(6,8,13-trisubstituted); or
$R^{A1}$, $R^{A2}$, $R^{A3}$, and $R^{A4}$ are all —H;
$R^{B5}$, $R^{B6}$, and $R^{B7}$ are all —H;
$R^{C9}$, $R^{C11}$, and $R^{C12}$ are all —H; and,
$R^{C10}$ is not —H;
(8,10,13-trisubstituted); or
$R^{A1}$, $R^{A2}$, and $R^{A4}$ are all —H;
$R^{B5}$ and $R^{B7}$ are both —H;
$R^{C9}$, $R^{C10}$, $R^{C11}$, and $R^{C12}$ are all —H; and,
$R^{A3}$ and $R^{B6}$ are both not —H;
(3,6,8,13-tetrasubstituted); or
$R^{A1}$, $R^{A2}$, and $R^{A4}$ are all —H;
$R^{B5}$, $R^{B6}$, and $R^{B7}$ are all —H;
$R^{C9}$, $R^{C11}$, and $R^{C12}$ are all —H; and,
$R^{A3}$ and $R^{C10}$ are both not —H;
(3,8,10,13-tetrasubstituted); or
$R^{A1}$, $R^{A2}$, $R^{A3}$, and $R^{A4}$ are all —H;

$R^{B5}$ and $R^{B7}$ are both —H;
$R^{C9}$, $R^{C11}$, and $R^{C12}$ are all —H; and,
$R^{B6}$ and $R^{C10}$ are both not —H;
(6,8,10,13-tetrasubstituted); or
$R^{A1}$, $R^{A2}$, and $R^{A4}$ are all —H;
$R^{B5}$ and $R^{B7}$ are both —H;
$R^{C9}$, $R^{C11}$, and $R^{C12}$ are all —H; and,
$R^{A3}$, $R^{B5}$, and $R^{C10}$ are a llnot —H;
(3,6,8,10,13-pentasubstituted); or
$R^{A1}$, $R^{A2}$, and $R^{A4}$ are all —H;
$R^{B5}$ and $R^{B7}$ are both —H;
$R^{C9}$, $R^{C10}$, and $R^{C12}$ are all —H; and,
$R^{A3}$, $R^{B6}$, and $R^{C11}$ are all not —H;
(3,6,8,11,13-pentasubstituted).

33. A method according to claim 30, wherein said nitrogen substituents, $R^{N8}$ and $R^{N13}$, are independently selected from:
  unsubstituted $C_{1-4}$alkyl;
  $C_{1-4}$haloalkyl;
  $C_{1-4}$hydroxyalkyl;
  $C_{1-4}$alkoxyalkyl;
  $C_{1-4}$carboxyalkyl; and
  $C_{1-4}$aminoalkyl.

34. A method according to claim 33, wherein said nitrogen substituents, $R^{N8}$ and $R^{N13}$, are not both -Et.

35. A method according to claim 30, wherein said nitrogen substituents, $R^{N8}$ and $R^{N13}$, are independently selected from:
  unsubstituted $C_1$alkyl;
  $C_1$haloalkyl;
  $C_1$hydroxyalkyl;
  $C_1$alkoxyalkyl;
  $C_1$carboxyalkyl; and
  $C_1$aminoalkyl.

36. A method according to claim 30, wherein each of said nitrogen substituents, $R^{N8}$ and $R^{N13}$, is independently -Me, —OF$_3$, —CHF$_2$, —CH$_2$F, —CH$_2$OH, or —CH$_2$NH$_2$.

37. A method according to claim 30, wherein said nitrogen substituents, $R^{N8}$ and $R^{N13}$, are both -Me.

38. A method according to claim 30, wherein each of said ring substituents is independently selected from:
  halo;
  ether;
  ester;
  acyloxy;
  oxycarbonyloxy;
  amido;
  acylamido;
  amino;
  nitro;
  cyano;
  azido;
  unsubstituted $C_{1-7}$alkyl;
  $C_{1-7}$haloalkyl;
  $C_{1-7}$hydroxyalkyl;
  $C_{1-7}$carboxyalkyl;
  $C_{1-7}$acyloxyalkyl;
  $C_{1-7}$oxycarbonylalkyl;
  $C_{1-7}$oxycarbonyloxyalkyl;
  $C_{1-7}$aminoalkyl;
  $C_{1-7}$amidoalkyl;
  $C_{1-7}$acylamidoalkyl;
  $C_{1-7}$cyanoalkyl; and
  $C_{5-20}$aryl-$C_{1-7}$alkyl.

39. A method according to claim 30, wherein each of said ring substituents is independently selected from:
  halo;
  $C_{1-7}$alkoxy;
  ester;
  acyloxy
  oxycarbonyloxy;
  cyano;
  unsubstituted $C_{1-7}$alkyl;
  $C_{1-7}$haloalkyl;
  $C_{1-7}$hydroxyalkyl;
  $C_{1-7}$carboxyalkyl;
  $C_{1-7}$acyloxyalkyl;
  $C_{1-7}$oxycarbonylalkyl;
  $C_{1-7}$oxycarbonyloxyalkyl;
  $C_{1-7}$aminoalkyl;
  $C_{1-7}$amidoalkyl;
  $C_{1-7}$acylamidoalkyl;
  $C_{1-7}$cyanoalkyl; and
  $C_{5-20}$aryl-$C_{1-7}$alkyl.

40. A method accorcilng to claim 33, wherein each of said ring substituents is independently selected from:
  halo;
  $C_{1-7}$alkoxy;
  ester;
  acyloxy;
  oxycarbonyloxy;
  cyano;
  unsubstituted $C_{1-7}$alkyl;
  $C_{1-7}$haloalkyl;
  $C_{1-7}$hydroxyalkyl;
  $C_{1-7}$carboxyalkyl;
  $C_{1-7}$acyloxyalkyl;
  $C_{1-7}$oxycarbonylalkyl;
  $C_{1-7}$oxycarbonyloxyalkyl;
  $C_{1-7}$aminoalkyl;
  $C_{1-7}$amidoalkyl;
  $C_{1-7}$acylamidoalkyl;
  $C_{1-7}$cyanoalkyl; and
  $C_{5-20}$aryl-$C_{1-7}$alkyl.

41. A method according to claim 30, wherein each of said ring substituents is independently selected from:
  —F, —Cl, —Br, —I;
  —OMe, —OEt, —C(nPr), —C(iPr), —O(nBu), —O(tBu), —OCH$_2$Ph;
  —OCF$_3$, —OCHF$_2$, —OCH$_2$F, —OCCl$_3$, —OCBr$_3$, —OCH$_2$CH$_2$F, —OCH$_2$CHF$_2$, —OCH$_2$CF$_3$;
  —C(=O)Me, —C(=O)Et, —C(=O)(nPr), —C(=O)(iPr), —C(=O)(nBu), —C(=O)(tBu), —C(=O)Ph;
  —C(=O)OMe, —C(=O)OEt, —C(=O)O(nPr), —C(=O)O(iPr), —C(=O)O(nBu), —C(=O)O(tBu);
  —OC(=O)Me, —OC(=O)Et, —OC(=O)(nPr), —OC(=O)(iPr), —OC(=O)(nBu), —OC(=O)(tBu);
  —OC(=O)OMe, —OC(=O)OEt, —OC(=O)O(nPr), —OC(=O)O(iPr), —OC(=O)O(nBu), —OC(=O)O(tBu);
  —C(=O)NH$_2$, —C(=O)NHMe, —C(=O)NHEt, —C(=O)NH(nPr), —C(=O)NH(iPr), —C(=O)NH(nBu), —C(=O)NH(tBu), —C(=O)NMe$_2$, —C(=O)NEt$_2$, —C(=O)N(nPr)$_2$, —C(=O)N(iPr)$_2$, —C(=O)N(nBu)$_2$, —C(=O)N(tBu)$_2$;
  —NHC(=O)Me, —NHC(=O)Et, —NHC(=O)(nPr), —NHC(=O)(iPr), —NHC(=O)(nBu), —NHC(=O)(tBu), —NHC(=O)Ph, succinimidyl, maleimidyl;
  —NH$_2$, —NHMe, —NHEt, —NH(nPr), —NH(iPr), —NH(nBu), —NH(tBu), —NMe$_2$, —NEt$_2$, —N(nPr)$_2$, —N(iPr)$_2$, —N(nBu)$_2$, —N(tBu)$_2$;
  —NH(CH$_2$)$_2$NH$_2$, —NH(CH$_2$)$_3$NH$_2$, —NH(CH$_2$)$_4$NH$_2$, —NH(CH$_2$)$_5$NH$_2$, —NH(CH$_2$)$_6$NH$_2$, —NHCH$_2$NH(Me), —NH(CH$_2$)$_2$NH(Me), —NH(CH$_2$)$_3$NH(Me), —NH(CH$_2$)$_4$NH(Me), —NH(CH$_2$)$_5$NH(Me), —NH(CH$_2$)$_6$NH(Me), —NHCH$_2$NH(Et), —NH(CH$_2$)$_2$NH(Et), —NH(CH$_2$)$_3$NH(Et), —NH(CH$_2$)$_4$NH(Et), —NH(CH$_2$)$_5$NH(Et), —NH(CH$_2$)$_6$NH(Et);
—NO$_2$;
—CN;
—N$_3$;
-Me, -Et, -nPr, -iPr, -nBu, -tBu;
—CF$_3$, —CHF$_2$, —CH$_2$F, —CCl$_3$, —CBr$_3$, —CH$_2$CH$_2$F, —CH$_2$CHF$_2$, —CH$_2$CF$_3$;
—CH$_2$OH, —CH$_2$CH$_2$OH, —CH(OH)CH$_2$OH;
—CH$_2$COOH, —CH$_2$CH$_2$COOH, —CH$_2$CH$_2$CH$_2$COOH;
—CH$_2$OC(=O)Me, —CH$_2$CH$_2$OC(=O)Me, —CH=CHOC(=O)Me;
—CH$_2$C(=O)OMe, —CH$_2$CH$_2$C(=O)OMe, —CH=CHC(=O)OMe;
—CH$_2$OC(=O)OMe, —CH$_2$CH$_2$OC(=O)OMe, —CH=CHOC(=O)OMe;
—CH$_2$NH$_2$, —CH$_2$CH$_2$NH$_2$, —CH=CHNH$_2$, —CH$_2$CH$_2$NMe$_2$;
—CH$_2$NHC(=O)Me, —CH$_2$CH$_2$NHC(=O)Me, —CH=CHNHC(=O)Me;
—CH$_2$C(=O)NH$_2$, —CH$_2$CH$_2$C(=O)NH$_2$, —CH=CHC(=O)NH$_2$;
—CH$_2$CN, —CH$_2$CH$_2$CN, and —CH=CHCN.

42. A method according to claim 30, wherein each of said ring substituents is independently selected from:
—F, —Cl, -Me, —OMe, —CN,
—C(=O)OMe, —OC(=O)Me, —OC(=O)OMe,
—CH$_2$CH$_2$C(=O)OMe,
—CH$_2$CH$_2$OC(=O)Me,
—CH=CHC(=O)OMe,
—CH=CHOC(=O)Me,
—CH=CHC(=O)NH$_2$,
—CH=CHC(=O)(morpholin-4-yl),
—CH=CHCH$_2$NHC(=O)CF$_3$,
—CH=CHCN, and
—C≡CCH$_2$NHC(=O)CF$_3$.

43. A method according to claim 30, wherein each of said ring substituents is independently: —F, —Cl, -Me, —OMe, —C(=O)OMe, —OC(=O)Me, or —OC(=O)OMe.

44. A method according to claim 33, wherein each of said ring substituents is independently: —F, —Cl, -Me, —OMe, —C(=O)OMe, —OC(=O)Me, or —OC(=O)OMe.

45. A method according to claim 34, wherein each of said ring substituents is independently: —F, —Cl, -Me, —OMe, —C(=O)OMe, —OC(=O)Me, or —OC(=O)OMe.

46. A method according to claim 30, wherein the anion is independently derived from one or more of: the following inorganic acids: hydrochloric, hydrobromic, hydroiodic, sulfuric, sulfurous, nitric, nitrous, phosphoric, and phosphorous; the following organic acids: acetic, propionic, succinic, gycolic, stearic, lactic, malic, tartaric, citric, ascorbic, maleic, hydroxymaleic, phenylacetic, glutamic, benzoic, salicylic, sulfanilic, 2-acetoxybenzoic, fumaric, toluenesulfonic, methanesulfonic, ethanesulfonic, ethane disulfonic, oxalic, isethionic, gluconic, and valeric; and the following polymeric acids: tannic acid and carboxymethyl cellulose.

47. A method according to claim 33, wherein the anion is independently derived from one or more of: the following inorganic acids: hydrochloric, hydrobromic, and hydroiodic; and the following organic acids: methanesulfonic, ethanesulfonic, isethionic, fumaric, and gluconic.

48. A method according to claim 45, wherein the anion is independently chloride, bromide, iodide, methylsulfate, ethylsulfate, isethionate, fumarate, or gluconate.

49. A method according to claim 45, wherein the anion is independently iodide or methylsulfate.

50. A method according to claim 30, wherein the compound is selected from the following compounds, and pharmaceutically acceptable salts and solvates thereof:

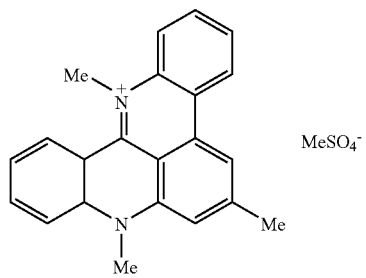

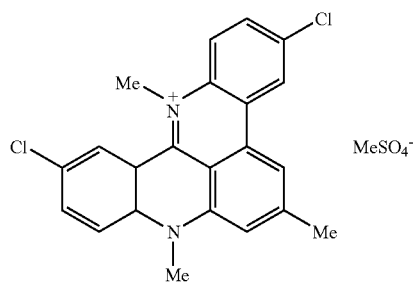

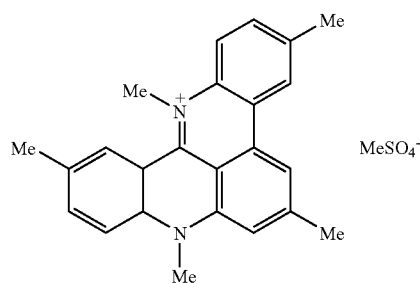

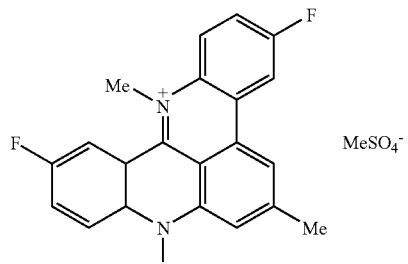

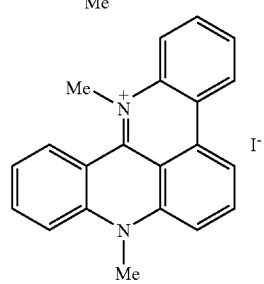

123
-continued
124
-continued
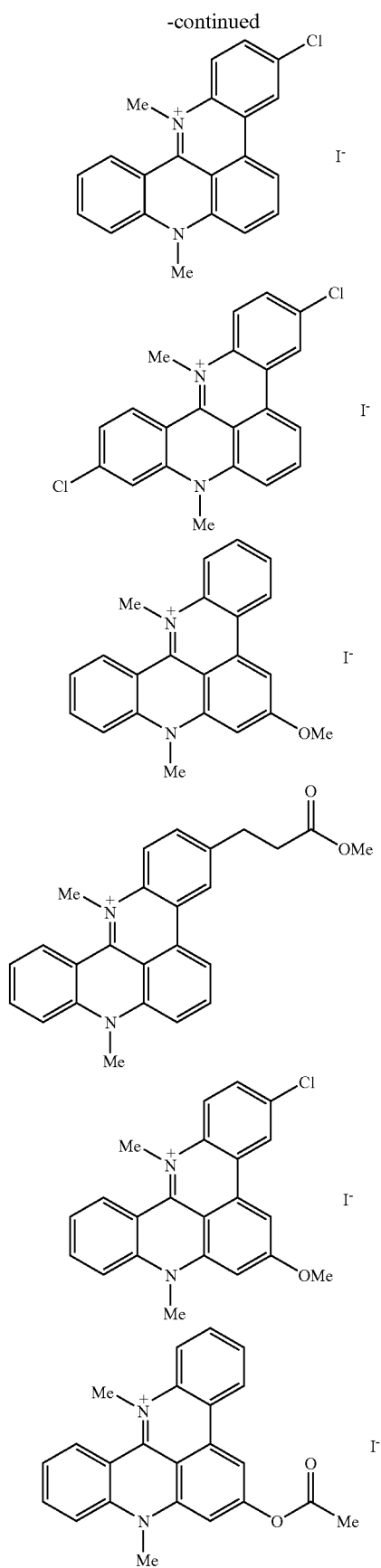
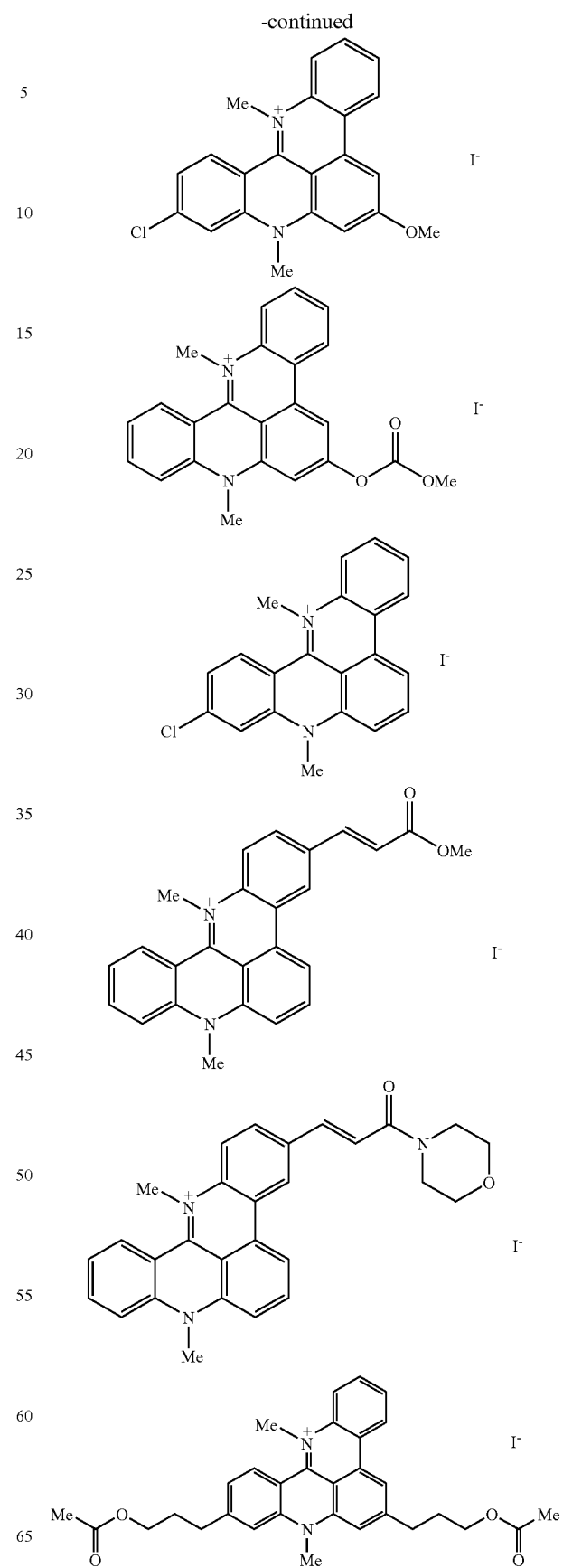

-continued

[Chemical structures shown]

51. A method of treating cancer in a subject comprising administering to said subject a therapeutically-effective amount of a compound selected from compounds of the following formula and pharmaceutically acceptable salts and solvates thereof:

[Chemical structure with substituents $R^{A1}$, $R^{A2}$, $R^{A3}$, $R^{A4}$, $R^{B5}$, $R^{B6}$, $R^{B7}$, $R^{C9}$, $R^{C10}$, $R^{C11}$, $R^{C12}$, $R^{N8}$, $R^{N13}$, $Q^-$]

wherein:
each one of $R^{A1}$, $R^{A2}$, $R^{A3}$, and $R^{A4}$ is independently —H or a ring substituent;
each one of $R^{B5}$, $R^{B6}$, and $R^{B7}$ is independently —H or a ring substituent;
each one of $R^{C9}$, $R^{C10}$, $R^{C11}$, and $R^{C12}$ is independently —H or a ring substituent;
$R^{N8}$ is independently a nitrogen substituent;
$R^{N13}$ is independently a nitrogen substituent; and,
Q is independently an anion; and,
wherein:
said ring substituents are independently selected from:
  halo;
  hydroxy;
  ether;
  formyl;
  acyl;
  carboxy;
  ester;
  acyloxy;
  oxycarbonyloxy;
  amido;
  acylamido;
  tetrazolyl;
  amino;
  nitro;
  cyano;
  azido;
  sulfhydryl;
  thioether;
  sulfonamido;
  unsubstituted $C_{1-7}$alkyl;
  $C_{1-7}$haloalkyl;
  $C_{1-7}$hydroxyalkyl;
  $C_{1-7}$carboxyalkyl;
  $C_{1-7}$acyloxyalkyl;
  $C_{1-7}$oxycarbonylalkyl;
  $C_{1-7}$oxycarbonyloxyalkyl;
  $C_{1-7}$aminoalkyl;
  $C_{1-7}$amidoalkyl;
  $C_{1-7}$acylamidoalkyl;
  $C_{1-7}$cyanoalkyl; and
  $C_{5-20}$aryl-$C_{1-7}$alkyl; and,
said nitrogen substituents are independently selected from:
  unsubstituted $C_{1-7}$alkyl;
  $C_{1-7}$haloalkyl;
  $C_{1-7}$hydroxyalkyl;
  $C_{1-7}$alkoxyalkyl;
  $C_{1-7}$carboxyalkyl;
  $C_{1-7}$aminoalkyl;

$C_{5-20}$aryl-$C_{1-7}$alkyl;
$C_{3-20}$heterocyclyl;
$C_{5-20}$aryl;
$C_{1-7}$alkyl-$C_{5-20}$aryl; and
$C_{5-20}$haloaryl;
and wherein:
  each alkyl group is aliphatic, and is saturated or partially unsaturated; and
  each aryl group is a carboaryl group or a heteroaryl group.

52. A method according to claim 51, wherein:
$R^{A1}$ and $R^{A4}$ are both —H;
$R^{B5}$ and $R^{B7}$ are both —H;
$R^{C9}$ and $R^{C12}$ are both —H;
and wherein the compound is selected from compounds of the following formula
and pharmaceutically acceptable salts and solvates thereof:

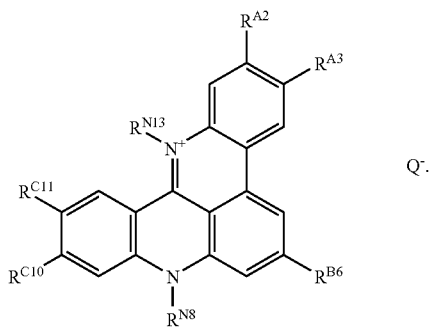

53. A method according to claim 52, wherein each of said nitrogen substituents, $R^{N8}$ and $R^{N13}$, is independently -Me, —$CF_3$, —$CHF_2$, —$CH_2F$, —$CH_2OH$, or —$CH_2NH_2$.

54. A method according to claim 52, wherein said nitrogen substituents, $R^{N8}$ and $R^{N13}$, are both -Me.

55. A method according to claim 52, wherein each of said ring substituents is independently: —F, —Cl, -Me, —OMe, —C(=O)OMe, —OC(=O)Me, or —OC(=O)OMe.

56. A method according to claim 53, wherein each of said ring substituents is independently: —F, —Cl, -Me, —OMe, —C(=O)OMe, —OC(=O)Me, or —OC(=O)OMe.

57. A method according to claim 54, wherein each of said ring substituents is independently: —F, —Cl, -Me, —OMe, —C(=O)OMe, —OC(=O)Me, or —OC(=O)OMe.

58. A method according to claim 51, wherein the compound is selected from the following compounds, and pharmaceutically acceptable salts and solvates thereof:

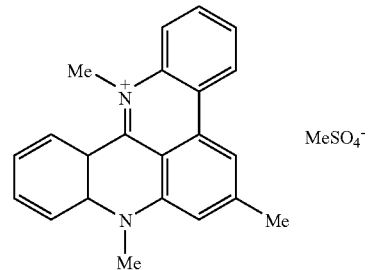

-continued

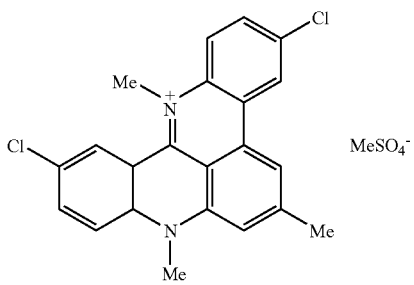

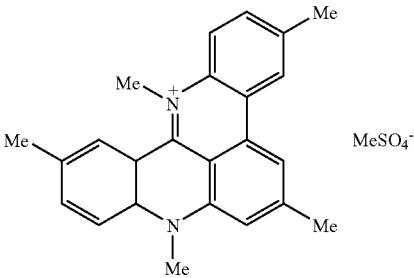

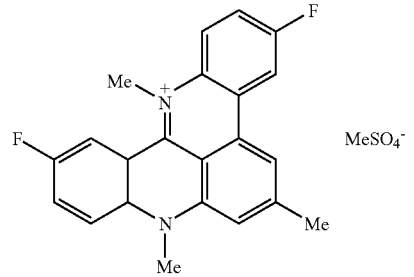

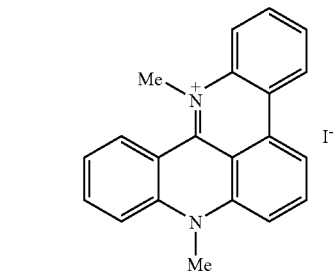

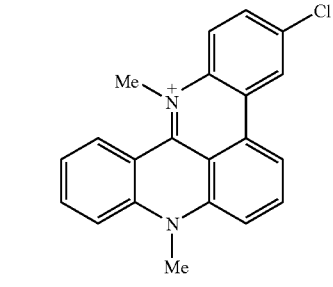

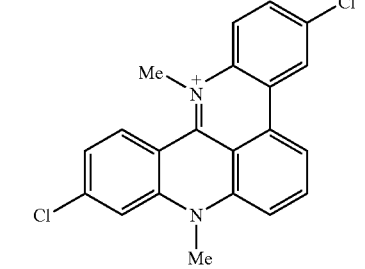

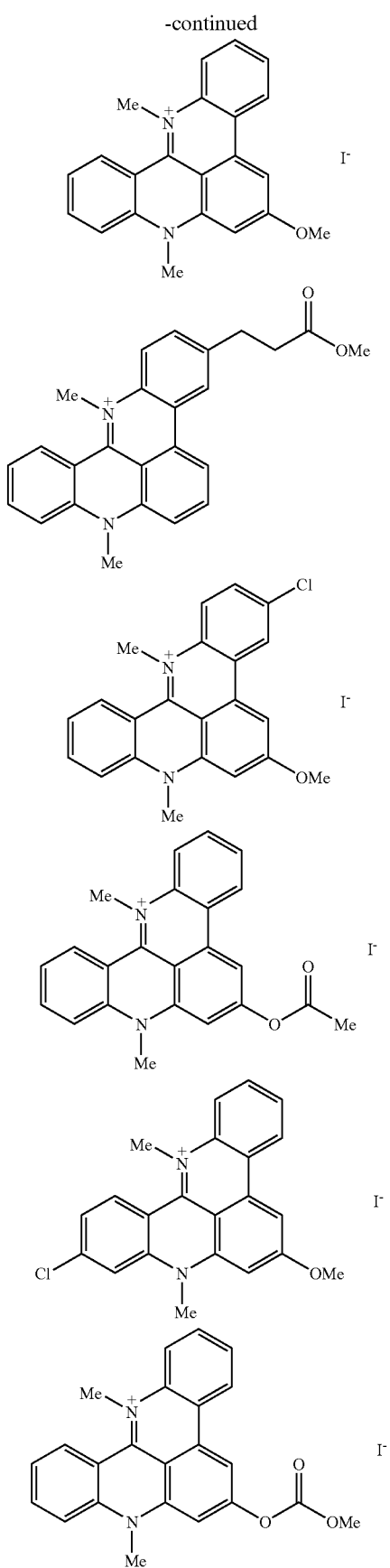

-continued
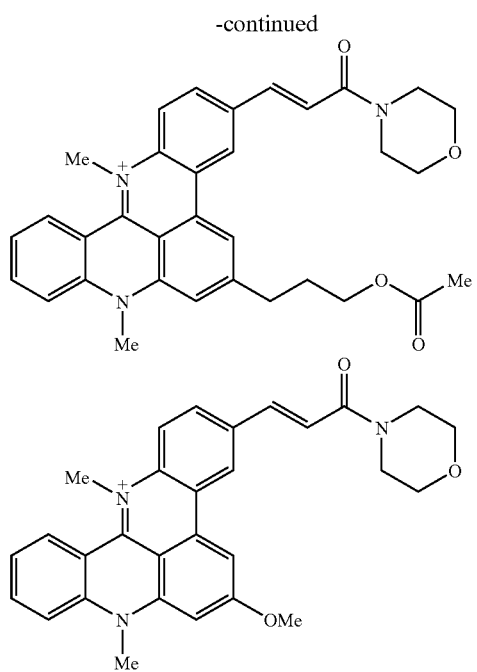
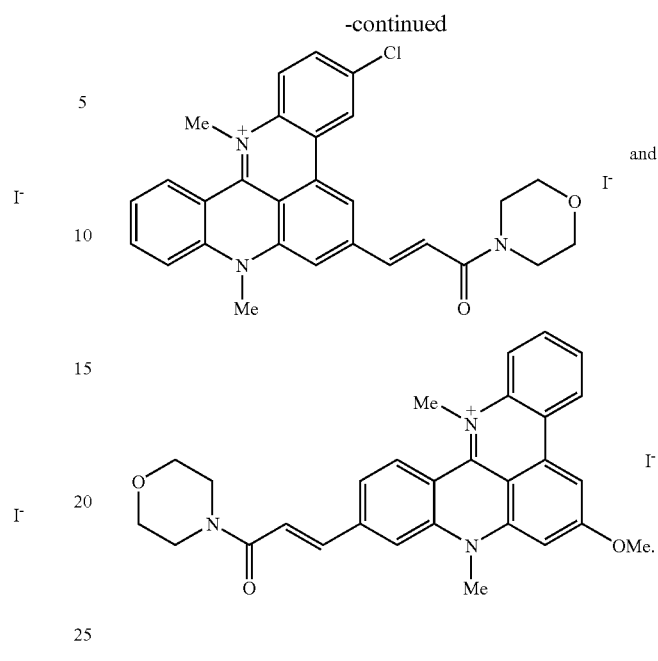
* * * * *

UNITED STATES PATENT AND TRADEMARK OFFICE
CERTIFICATE OF CORRECTION

PATENT NO. : 7,115,619 B2
APPLICATION NO. : 10/398767
DATED : October 3, 2006
INVENTOR(S) : M. Stevens et al.

It is certified that error appears in the above-identified patent and that said Letters Patent is hereby corrected as shown below:

In the Specifications:

In column 26, replace the formula "9 RHPS01" with the following formula:

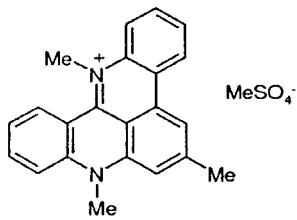

In column 26, replace the formula "10 RHPS02" with the following formula:

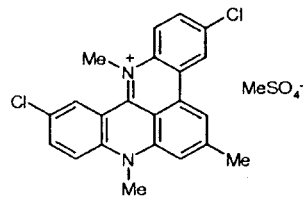

In column 26, replace the formula "11 RHPS03" with the following formula:

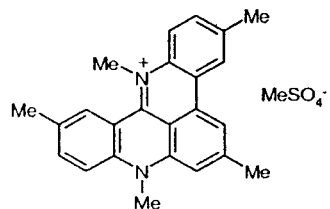

In column 27, replace the formula "12 RHPS04" with the following formula:

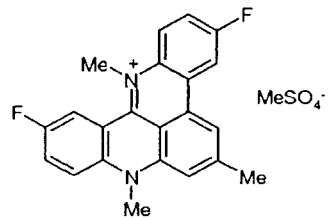

Signed and Sealed this
Eighteenth Day of June, 2013

Teresa Stanek Rea
*Acting Director of the United States Patent and Trademark Office*

In column 47, replace the formula in "Scheme 6" after the arrow with the following formula:
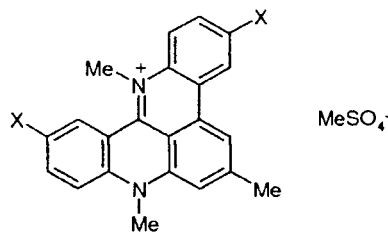
In the Claims:
Replace the first four formulas in column 113, lines 10-55 (claim 28, lines 4-7) with the following four formulas:
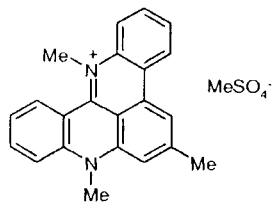
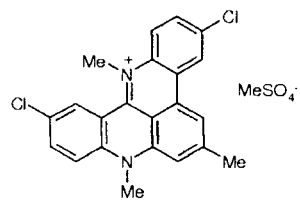
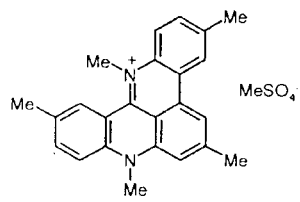
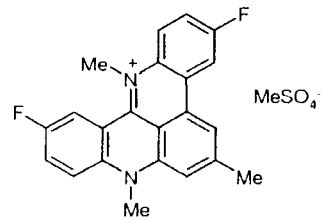

Replace the first four formulas in column 122, lines 10-55 (claim 50, lines 4-7) with the following four formulas:
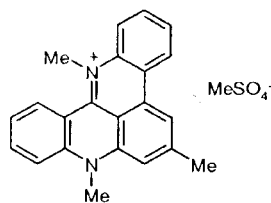
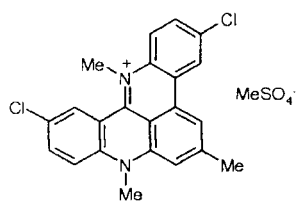
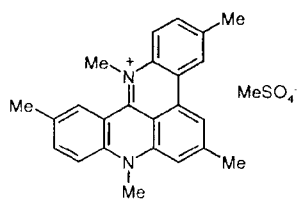
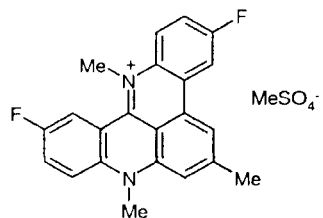

CERTIFICATE OF CORRECTION (continued)

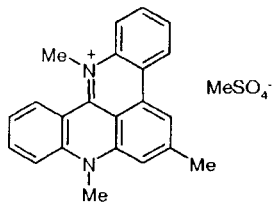

Replace the first four formulas of claim 58, spanning line 55 of column 127 to line 35 of column 128 (claim 58, lines 4-7) with the following four formulas: